US011021424B2

(12) United States Patent
Miller et al.

(10) Patent No.: US 11,021,424 B2
(45) Date of Patent: Jun. 1, 2021

(54) REDOX-ACTIVE THERAPEUTICS FOR TREATMENT OF MITOCHONDRIAL DISEASES AND OTHER CONDITIONS AND MODULATION OF ENERGY BIOMARKERS

(75) Inventors: Guy M. Miller, Monte Sereno, CA (US); Sidney M. Hecht, Charlottesville, VA (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 1352 days.

(21) Appl. No.: 12/777,179

(22) Filed: May 10, 2010

(65) Prior Publication Data
US 2010/0222436 A1 Sep. 2, 2010

Related U.S. Application Data

(62) Division of application No. 11/445,582, filed on Jun. 1, 2006, now Pat. No. 9,447,006.

(60) Provisional application No. 60/776,028, filed on Feb. 22, 2006, provisional application No. 60/701,815, filed on Jul. 21, 2005, provisional application No. 60/686,826, filed on Jun. 1, 2005.

(51) Int. Cl.
| | |
|---|---|
| *C07C 37/07* | (2006.01) |
| *A61K 31/355* | (2006.01) |
| *C07C 39/08* | (2006.01) |
| *C07C 39/19* | (2006.01) |
| *C07C 39/24* | (2006.01) |
| *C07C 46/00* | (2006.01) |
| *C07C 46/02* | (2006.01) |
| *C07C 46/08* | (2006.01) |
| *C07C 50/02* | (2006.01) |
| *C07C 50/06* | (2006.01) |
| *C07C 50/28* | (2006.01) |
| *A61P 25/00* | (2006.01) |

(52) U.S. Cl.
CPC ............ *C07C 37/07* (2013.01); *A61K 31/355* (2013.01); *A61P 25/00* (2018.01); *C07C 39/08* (2013.01); *C07C 39/19* (2013.01); *C07C 39/24* (2013.01); *C07C 39/245* (2013.01); *C07C 46/00* (2013.01); *C07C 46/02* (2013.01); *C07C 46/08* (2013.01); *C07C 50/02* (2013.01); *C07C 50/06* (2013.01); *C07C 50/28* (2013.01)

(58) Field of Classification Search
CPC ....... A61K 31/355; A61P 25/00; C07C 37/07; C07C 39/08; C07C 39/245
See application file for complete search history.

(56) References Cited

U.S. PATENT DOCUMENTS

| | | | |
|---|---|---|---|
| 2,398,418 A | 4/1946 | Fieser | |
| 2,856,414 A | 10/1958 | Robeson et al. | |
| 3,071,512 A | 1/1963 | Feldmann | |
| 3,406,188 A | 10/1968 | Fletcher | |
| 3,705,239 A | 12/1972 | Gregory | |
| T917,001 I4 | 12/1973 | Anderson, Jr. et al. | |
| 3,849,453 A | 11/1974 | Morrimoto et al. | |
| 3,896,153 A | 7/1975 | Sato et al. | |
| 3,909,376 A | 9/1975 | Degner | |
| 3,957,836 A | 5/1976 | Morimoto et al. | |
| 4,127,608 A | 11/1978 | Olson | |
| 4,153,614 A | 5/1979 | Barner et al. | |
| 4,185,154 A | 1/1980 | Olson et al. | |
| 4,201,726 A | 5/1980 | Olson et al. | |
| 4,201,879 A | 5/1980 | Barner et al. | |
| 4,234,490 A | 11/1980 | Barner et al. | |
| 4,243,598 A | 1/1981 | Olson et al. | |
| 4,310,465 A | 1/1982 | Olson et al. | |
| 4,388,312 A | 6/1983 | Terao et al. | |
| 4,393,075 A | 7/1983 | Terao et al. | |
| 4,436,753 A | 3/1984 | Imada et al. | |
| 4,491,594 A | 1/1985 | Ogawa et al. | |
| 4,495,104 A | 1/1985 | Imada et al. | |
| 4,559,177 A | 12/1985 | Okutani et al. | |
| 4,559,407 A | 12/1985 | Barner et al. | |
| 4,592,867 A | 6/1986 | Yu et al. | |
| 4,599,232 A | 7/1986 | Bertelli | |
| 4,617,317 A * | 10/1986 | Bennet | 514/458 |

(Continued)

FOREIGN PATENT DOCUMENTS

| | | |
|---|---|---|
| CA | 2430415 | 6/2002 |
| CN | 1441793 | 9/2003 |

(Continued)

OTHER PUBLICATIONS

Ansell et al 'The Pharmacology and Management of the Vitamin K Antagonists' Chest, 126(3), Supplement, p. 204S-233S, 2004.*
Viscomi et al. Emerging concepts in the therapy of mitochondrial disease. Biochimica et Biophysica Acta. 1847, 2015, 544-557.*
Rahman. Mitochondrial disease and epilepsy. (Developmental Medicine & Child Neurology, 2012, 54: 397-406).*
Adelwöhrer, C. et al. (2005, e-pub. Aug. 2, 2005). "Novel Tocopheryl Compounds XX. 1,3,8-Trioxaphenanthrenes Derived from γ-Tocopherol," *Tetrahedron* 61:9070-9074.

(Continued)

*Primary Examiner* — Anna Pagonakis
(74) *Attorney, Agent, or Firm* — Squire Patton Boggs (US) LLP

(57) ABSTRACT

Methods of treating or suppressing mitochondrial diseases, such as Friedreich's ataxia (FRDA), Leber's Hereditary Optic Neuropathy (LHON), mitochondrial myopathy, encephalopathy, lactacidosis, stroke (MELAS), or Kearns-Sayre Syndrome (KSS) are disclosed, as well as compounds useful in the methods of the invention, such as alpha-tocopherol quinone. Methods and compounds useful in treating other disorders are also disclosed. Energy biomarkers useful in assessing the metabolic state of a subject and the efficacy of treatment are also disclosed. Methods of modulating, normalizing, or enhancing energy biomarkers, as well as compounds useful for such methods, are also disclosed.

85 Claims, No Drawings

(56) References Cited

U.S. PATENT DOCUMENTS

| | | |
|---|---|---|
| 4,694,090 A | 9/1987 | Shiono et al. |
| 4,804,539 A | 2/1989 | Guo et al. |
| 4,814,346 A | 3/1989 | Albert et al. |
| 4,818,441 A | 4/1989 | Imada et al. |
| 4,831,265 A | 5/1989 | Watanabe et al. |
| 4,883,658 A | 11/1989 | Holly |
| 4,914,088 A | 4/1990 | Glonek et al. |
| 5,057,514 A | 10/1991 | Tatsuoka et al. |
| 5,059,627 A | 10/1991 | Goto et al. |
| 5,075,104 A | 12/1991 | Gressel et al. |
| 5,157,132 A | 10/1992 | Tan et al. |
| 5,179,092 A | 1/1993 | Tatsuoka et al. |
| 5,180,742 A | 1/1993 | Terao et al. |
| 5,190,618 A | 3/1993 | Top et al. |
| 5,210,239 A | 5/1993 | Abe et al. |
| 5,229,385 A | 7/1993 | Terao et al. |
| 5,278,151 A | 1/1994 | Korb et al. |
| 5,288,752 A | 2/1994 | Tatsuoka et al. |
| 5,292,768 A | 3/1994 | Tatsuoka et al. |
| 5,294,607 A | 3/1994 | Glonek et al. |
| 5,304,658 A | 4/1994 | Terao et al. |
| 5,318,993 A | 6/1994 | Pearce |
| 5,371,108 A | 12/1994 | Korb et al. |
| 5,547,827 A | 8/1996 | Chen et al. |
| 5,563,129 A | 10/1996 | Masuya et al. |
| 5,578,586 A | 11/1996 | Glonek et al. |
| 5,600,029 A | 2/1997 | Kaneko et al. |
| 5,801,159 A | 9/1998 | Miller et al. |
| 5,846,988 A | 12/1998 | Hellberg |
| 5,872,108 A | 2/1999 | Sandage, Jr. et al. |
| 5,874,461 A | 2/1999 | De Chaffoy de Courcelles et al. |
| 5,886,030 A | 3/1999 | Maniar |
| 5,969,133 A | 10/1999 | Ono et al. |
| 5,981,601 A | 11/1999 | Nagley et al. |
| 6,011,046 A | 1/2000 | Ohkawa et al. |
| 6,045,826 A | 4/2000 | Borowy-Borowski et al. |
| 6,048,891 A | 4/2000 | Wechter |
| 6,083,982 A | 7/2000 | Wechter et al. |
| 6,133,278 A | 10/2000 | Terao et al. |
| 6,133,322 A | 10/2000 | Rustin et al. |
| 6,136,859 A | 10/2000 | Henriksen |
| 6,150,402 A | 11/2000 | Wechter et al. |
| 6,187,811 B1 | 2/2001 | Lane |
| 6,232,060 B1 | 5/2001 | Miller et al. |
| 6,239,171 B1 | 5/2001 | Lane et al. |
| 6,271,266 B1 | 8/2001 | Miyamoto et al. |
| 6,297,281 B1 | 10/2001 | Chabrier de Lassauniere et al. |
| 6,300,377 B1 | 10/2001 | Chopra |
| 6,331,532 B1 | 12/2001 | Murphy et al. |
| 6,342,516 B1 | 1/2002 | Umeda et al. |
| 6,395,915 B1 | 5/2002 | Bellafiore et al. |
| 6,417,233 B1 | 7/2002 | Sears et al. |
| 6,426,362 B1 | 7/2002 | Miller et al. |
| 6,433,199 B1 | 8/2002 | Ono et al. |
| 6,472,378 B2 | 10/2002 | Von Borstel |
| 6,528,042 B1 | 3/2003 | Brown et al. |
| 6,545,184 B1 | 4/2003 | Lipshutz |
| 6,562,372 B1 | 5/2003 | Yokoi et al. |
| 6,608,196 B2 | 8/2003 | Wang et al. |
| 6,638,104 B2 | 10/2003 | Hashimoto et al. |
| 6,653,346 B1 | 11/2003 | Wang et al. |
| 6,656,358 B2 | 12/2003 | May et al. |
| 6,740,338 B1 | 5/2004 | Chopra |
| 6,764,768 B2 | 7/2004 | Mrksich et al. |
| 6,852,895 B2 | 2/2005 | Lipshutz et al. |
| 6,977,270 B2 | 12/2005 | Baldenius et al. |
| 7,034,054 B2 | 4/2006 | Miller et al. |
| 7,038,067 B2 | 5/2006 | Couladouros et al. |
| 7,078,541 B2 | 7/2006 | Boddupalli et al. |
| 7,118,688 B2 | 10/2006 | Mora-Gutierrez et al. |
| 7,119,117 B2 | 10/2006 | Beinlich et al. |
| 7,393,662 B2 | 7/2008 | Heavner et al. |
| 7,432,305 B2 | 10/2008 | Miller et al. |
| 7,470,798 B2 | 12/2008 | Wang et al. |
| 7,491,312 B2 | 2/2009 | Gilat et al. |
| 7,514,461 B2 | 4/2009 | Wang et al. |
| 7,718,176 B2 | 5/2010 | Heavner et al. |
| 7,875,607 B2 | 1/2011 | Wang et al. |
| 7,968,746 B2 | 6/2011 | Jankowski et al. |
| 8,044,097 B2 | 10/2011 | Wang et al. |
| 8,106,223 B2 | 1/2012 | Wesson et al. |
| 8,182,990 B2 | 5/2012 | Mashima et al. |
| 8,314,153 B2 | 11/2012 | Miller et al. |
| 8,394,392 B2 | 3/2013 | Imahashi et al. |
| 8,519,001 B2 | 8/2013 | Jankowski et al. |
| 8,575,369 B2 | 11/2013 | Wesson et al. |
| 8,653,144 B2 | 2/2014 | Miller et al. |
| 8,716,486 B2 | 5/2014 | Hinman et al. |
| 8,716,527 B2 | 5/2014 | Hinman et al. |
| 8,791,155 B2 | 7/2014 | Wang et al. |
| 9,162,957 B2 | 10/2015 | Mollard |
| 9,278,085 B2 | 3/2016 | Miller et al. |
| 9,296,712 B2 | 3/2016 | Hinman et al. |
| 2001/0044462 A1 | 11/2001 | Hensley et al. |
| 2002/0032171 A1 | 3/2002 | Chen et al. |
| 2002/0132845 A1 | 9/2002 | Miller et al. |
| 2002/0142083 A1 | 10/2002 | Jacobs et al. |
| 2002/0182196 A1 | 12/2002 | McCleary |
| 2003/0022818 A1 | 1/2003 | Miller et al. |
| 2003/0119054 A1 | 6/2003 | Mrksich et al. |
| 2003/0134028 A1 | 7/2003 | Lievense |
| 2003/0144219 A1 | 7/2003 | Phinney et al. |
| 2003/0158237 A1 | 8/2003 | Saragovi et al. |
| 2003/0206972 A1 | 11/2003 | Babish et al. |
| 2004/0029954 A1 | 2/2004 | Wechter |
| 2004/0043013 A1 | 3/2004 | McCleary |
| 2004/0043103 A1 | 3/2004 | McCleary |
| 2004/0058986 A1 | 3/2004 | Wechter |
| 2004/0058987 A1 | 3/2004 | Wechter |
| 2004/0063661 A1 | 4/2004 | Linnane |
| 2004/0152764 A1 | 8/2004 | Miller et al. |
| 2004/0156871 A1 | 8/2004 | Borowy-Borowski et al. |
| 2005/0043553 A1 | 2/2005 | Smith et al. |
| 2005/0049227 A1 | 3/2005 | Old et al. |
| 2005/0065099 A1 | 3/2005 | Walkinshaw et al. |
| 2005/0065150 A1 | 3/2005 | Wang et al. |
| 2005/0074447 A1 | 4/2005 | Papas et al. |
| 2005/0186518 A1 | 8/2005 | Maskasky et al. |
| 2005/0203066 A1 | 9/2005 | Bon Borstel |
| 2005/0222218 A1 | 10/2005 | Meier et al. |
| 2005/0234248 A1 | 10/2005 | Kossler et al. |
| 2005/0256186 A1 | 11/2005 | Morishige |
| 2006/0002885 A1 | 1/2006 | Milke et al. |
| 2006/0241174 A1 | 10/2006 | Mueller et al. |
| 2006/0281809 A1 | 12/2006 | Miller et al. |
| 2007/0066541 A1 | 3/2007 | Hughes et al. |
| 2007/0135335 A1 | 6/2007 | Collier et al. |
| 2007/0180544 A1 | 8/2007 | Taylor et al. |
| 2007/0225261 A1 | 9/2007 | Miller et al. |
| 2007/0248590 A1 | 9/2007 | Milne et al. |
| 2008/0093985 A1 | 4/2008 | Morishita et al. |
| 2008/0221050 A1 | 9/2008 | Mashima |
| 2009/0036542 A1 | 2/2009 | Luu et al. |
| 2009/0060981 A1 | 3/2009 | Chauhan |
| 2009/0162890 A1 | 6/2009 | Gilat et al. |
| 2009/0163529 A1 | 6/2009 | Gilat et al. |
| 2009/0291092 A1 | 11/2009 | Miller et al. |
| 2010/0010100 A1 | 1/2010 | Hinman et al. |
| 2010/0029706 A1 | 2/2010 | Miller et al. |
| 2010/0029784 A1 | 2/2010 | Hinman et al. |
| 2010/0056429 A1 | 3/2010 | Miller et al. |
| 2010/0093845 A1 | 4/2010 | Wong et al. |
| 2010/0222436 A1 | 9/2010 | Miller et al. |
| 2010/0249032 A1 | 9/2010 | Heavner et al. |
| 2010/0266591 A1 | 10/2010 | Bugelski et al. |
| 2010/0273892 A1 | 10/2010 | Miller et al. |
| 2010/0273894 A1 | 10/2010 | Miller |
| 2011/0046156 A1 | 2/2011 | Miller |
| 2011/0046219 A1 | 2/2011 | Hinman et al. |
| 2011/0124679 A1 | 5/2011 | Hinman et al. |
| 2011/0142834 A1 | 6/2011 | Miller |
| 2011/0172312 A1 | 7/2011 | Miller et al. |
| 2011/0207828 A1 | 8/2011 | Miller et al. |
| 2011/0218208 A1 | 9/2011 | Hinman et al. |

(56) References Cited

U.S. PATENT DOCUMENTS

| | | |
|---|---|---|
| 2011/0269776 A1 | 11/2011 | Miller |
| 2012/0088783 A1 | 4/2012 | Wang et al. |
| 2012/0101169 A1 | 4/2012 | Hawi |
| 2012/0122934 A1 | 5/2012 | Jankowski et al. |
| 2012/0122969 A1 | 5/2012 | Miller |
| 2012/0130093 A1 | 5/2012 | Wesson et al. |
| 2012/0136048 A1 | 5/2012 | Miller et al. |
| 2012/0295985 A1 | 11/2012 | Miller et al. |
| 2013/0053450 A1 | 2/2013 | Miller et al. |
| 2013/0109759 A1 | 5/2013 | Miller |
| 2013/0116336 A1 | 5/2013 | Shrader |
| 2013/0267538 A1 | 10/2013 | Walkinshaw et al. |
| 2013/0289034 A1 | 10/2013 | Jankowski et al. |
| 2013/0345312 A1 | 12/2013 | Jankowski et al. |
| 2014/0031432 A1 | 1/2014 | Jankowski et al. |
| 2014/0031433 A1 | 1/2014 | Jankowski et al. |
| 2014/0039065 A1 | 2/2014 | Miller |
| 2014/0243424 A1 | 8/2014 | Mollard et al. |
| 2014/0249160 A1 | 9/2014 | Miller |
| 2014/0275045 A1 | 9/2014 | Hinman et al. |
| 2014/0343166 A1 | 11/2014 | Miller et al. |
| 2015/0057363 A1 | 2/2015 | Miller et al. |
| 2015/0216820 A1 | 8/2015 | Miller et al. |
| 2015/0218079 A1 | 8/2015 | Shrader et al. |
| 2015/0297551 A1 | 10/2015 | Miller et al. |
| 2016/0024085 A1 | 1/2016 | Hinman et al. |
| 2018/0000749 A1 | 1/2018 | Mollard et al. |
| 2018/0002247 A1 | 1/2018 | Mollard et al. |
| 2018/0370892 A1 | 12/2018 | Hinman et al. |
| 2019/0241497 A1 | 8/2019 | Hinman et al. |

FOREIGN PATENT DOCUMENTS

| | | |
|---|---|---|
| DE | 38 18 696 C1 | 3/1989 |
| EP | 0025692 A1 | 3/1981 |
| EP | 0 065 368 | 11/1982 |
| EP | 0 107 806 A1 | 5/1984 |
| EP | 0 107 806 B1 | 5/1984 |
| EP | 0 134 198 A1 | 3/1985 |
| EP | 0 326 987 | 8/1989 |
| EP | 0 619 313 A1 | 10/1994 |
| EP | 0 629 400 A1 | 12/1994 |
| EP | 0 719 552 A2 | 7/1996 |
| EP | 0 719 552 A3 | 7/1996 |
| EP | 1 378 753 A1 | 1/2004 |
| EP | 1 378 753 B1 | 1/2004 |
| EP | 1 611 879 | 1/2006 |
| FR | 1.201.200 | 12/1959 |
| FR | 75.631 | 6/1961 |
| FR | 5.531 M | 12/1967 |
| FR | 1.536.576 | 8/1968 |
| JP | 40-9029 | 5/1965 |
| JP | 48-75564 | 10/1973 |
| JP | 49-88862 | 8/1974 |
| JP | 52-111576 A | 9/1977 |
| JP | 52-130922 | 11/1977 |
| JP | 56-140943 A | 11/1981 |
| JP | 57-050935 A | 3/1982 |
| JP | 58-018374 | 2/1983 |
| JP | 58-083698 A | 5/1983 |
| JP | 58-193689 A | 11/1983 |
| JP | 60-28919 A | 2/1985 |
| JP | 60-056902 A | 4/1985 |
| JP | 60-197621 | 10/1985 |
| JP | 61-040236 A | 2/1986 |
| JP | 63-063674 | 3/1988 |
| JP | 1-093554 A | 4/1989 |
| JP | 1 209445 A | 8/1989 |
| JP | 1-233278 | 9/1989 |
| JP | 5-11467 A | 1/1993 |
| JP | 8-92151 A | 4/1996 |
| JP | 2000-202297 A | 7/2000 |
| JP | 2003-64017 A | 3/2003 |
| JP | 2003-137716 A | 5/2003 |
| JP | 2007-529218 | 10/2007 |
| JP | 2008-542389 | 11/2008 |
| JP | 2009-527567 | 7/2009 |
| WO | WO-93/24650 A1 | 12/1993 |
| WO | WO 98/09653 | 3/1998 |
| WO | WO-98/34646 A2 | 8/1998 |
| WO | WO 99/25336 | 5/1999 |
| WO | WO 99/38860 | 8/1999 |
| WO | WO 00/35444 | 6/2000 |
| WO | WO-00/50043 A1 | 8/2000 |
| WO | WO 00/078296 | 12/2000 |
| WO | WO-00/78296 A2 | 12/2000 |
| WO | WO-00/78296 A3 | 12/2000 |
| WO | WO-01/52822 A1 | 7/2001 |
| WO | WO-01/92215 A2 | 12/2001 |
| WO | WO-01/92215 A3 | 12/2001 |
| WO | WO 02/06261 | 1/2002 |
| WO | WO-02/34259 A1 | 5/2002 |
| WO | WO-02/47680 A2 | 6/2002 |
| WO | WO-02/47680 A3 | 6/2002 |
| WO | WO 02/50054 | 6/2002 |
| WO | WO-02/067864 A2 | 9/2002 |
| WO | WO-02/067864 A3 | 9/2002 |
| WO | WO-03/064403 A1 | 8/2003 |
| WO | WO-2004/003565 A2 | 1/2004 |
| WO | WO-2004/003565 A3 | 1/2004 |
| WO | WO-2004/042353 A2 | 5/2004 |
| WO | WO-2004/042353 A3 | 5/2004 |
| WO | WO-2005/000357 A2 | 1/2005 |
| WO | WO-2005/000357 A3 | 1/2005 |
| WO | WO 2005/013911 | 2/2005 |
| WO | WO-2005/019232 A1 | 3/2005 |
| WO | WO-2005/032544 A1 | 4/2005 |
| WO | WO-2005/033092 A1 | 4/2005 |
| WO | WO-2005/033093 A1 | 4/2005 |
| WO | WO 2005/090602 | 9/2005 |
| WO | WO-2005/105159 A2 | 11/2005 |
| WO | WO-2005/105159 A3 | 11/2005 |
| WO | WO-2006/130775 A2 | 12/2006 |
| WO | WO-2006/130775 A3 | 12/2006 |
| WO | WO-2007/035496 A1 | 3/2007 |
| WO | WO-2007/095630 A2 | 8/2007 |
| WO | WO-2007/095630 A3 | 8/2007 |
| WO | WO-2007/100652 A2 | 9/2007 |
| WO | WO-2007/100652 A3 | 9/2007 |
| WO | WO 2008/157747 | 12/2008 |
| WO | WO 2009/023877 | 2/2009 |
| WO | WO 2009/111543 | 9/2009 |
| WO | WO-2010/030607 | 3/2010 |
| WO | WO-2011/041452 A2 | 4/2011 |
| WO | WO-2011/113018 A1 | 9/2011 |
| WO | WO 2011/137126 | 11/2011 |
| WO | WO-2012/019029 A2 | 2/2012 |
| WO | WO-2012/019029 A3 | 2/2012 |
| WO | WO-2012/019032 A1 | 2/2012 |
| WO | WO-2012/154613 A1 | 11/2012 |
| WO | WO-2012/170773 A1 | 12/2012 |
| WO | WO-2012/174286 A1 | 12/2012 |
| WO | WO-2013/006736 A1 | 1/2013 |
| WO | WO-2013/006737 A1 | 1/2013 |
| WO | WO-2013/013078 A1 | 1/2013 |
| WO | WO 2014/039682 | 3/2014 |
| WO | WO 2014/039862 | 3/2014 |
| WO | WO 2014/039917 | 3/2014 |
| WO | WO 2014/194292 | 12/2014 |
| WO | WO 2018/093957 | 5/2018 |

OTHER PUBLICATIONS

Asgill, J.O. et al. (Jan. 4, 1978). "Chromenylation of 2-Napthol and Alkylhydroquinones: Short Syntheses of (2RS,4'R,8'R)-α-Tocopherol (Vitamin E) and (2RS,4'R,8'R)-β-Tocopherol," *The Journal of the Chemical Society Chemical Communications* 1:59-60.

Asin-Cayuela, J. et al. (Jul. 30, 2004). "Fine-Tuning the Hydrophobicity of a Mitochondria-Targeted Antioxidant," *FEBS Letters* 571(1-3):9-16.

Babiroli, B. et al. (Jul. 1995). "Lipoic (Thioctic) Acid Increases Brain Energy Availability and Skeletal Muscle Performance as

(56) References Cited

OTHER PUBLICATIONS

Shown by In Vivo $^{31}$P-MRS in a Patient with Mitochondrial Cytopathy," *Journal of Neurology* 242(7):472-477.

Bentinger, M. et al. (May 23, 2008). "Polyisoprenoid Epoxides Stimulate the Biosynthesis of Coenzyme Q and Inhibit Cholesterol Synthesis," *The Journal of Biological Chemistry* 238(21):14645-14653.

Bentinger, M. et al. (2008). "Stimulation of Coenzyme Q Synthesis," *BioFactors* 32:99-111.

Boyer, P.D. (Feb. 19, 1951). "The Preparation of Reversible Oxidation Product of α-Tocopherol, α-Tocopheroxide and of Related Oxides," *Journal of the American Chemical Society* 73(2):733-740.

Brière, J-J. et al. (Apr. 16, 2004). "Quinone Analogues Regulate Mitochondrial Substrate Competitive Oxidation," *Biochemical and Biophysical Research Communications* 316(4):1138-1142.

Bridgelius-Flohe et al. (1999). "Vitamin E: Function and Metabolism," *The FASEB Journal* 13:1145-1155.

Butterfield, D.A. et al. (2002). "Vitamin E and Neurodegenerative Disorders Associated with Oxidative Stress," *Nutritional Neuroscience* 5(4):229-239.

Calviello, G. et al. (2003). "γ-Tocopheryl Quinone Induces Apoptosis in Cancer Cells Via Caspase-9 Activation and Cytochrome c Release," *Carcinogenesis* 24(3):427-433.

Caplus Accession No. 1967:18647, created May 12, 1984, 9 pages. (English Language Abstract Counterpart for Weichet, J. et al. (1996)).

Caplus Accession No. 1969:433438, created May 12, 1984, 1 page. (English Language Abstract Counterpart for FR 5.531).

Caplus Accession No. 1969:524242, created May 12, 1984, 3 pages. (English Language Abstract Counterpart for FR 1.536.576).

Caplus Accession No. 1989:553350, created Oct. 28, 1999, 4 pages. (English Language Abstract Counterpart for DE 38 18 696 C1).

Caplus Accession No. 2003:166979, created Mar. 5, 2003, 5 pages. (English Language Abstract Counterpart for JP 2003-64017).

Caplus Accession No. 2003:487787, created Jun. 27, 2003, 8 pages. (English Language Abstract Counterpart for Zwaiyed, F.R. et al. (2003)).

Chariot, P. et al. (Apr. 1994). "Determination of the Blood Lactate : Pyruvate Ratio as a Noninvasive Test for the Diagnosis of Zidovudine Myopathy," *Arthritis & Rheumatism* 37(4):583-586.

Chariot, P. et al. (Jul. 1994). "Optimal Handling of Blood Samples for Routine Measurement of Lactate and Pyruvate," *Archives of Pathology & Laboratory Medicine* 118(7):695-697.

Cichewicz, R.H. et al. (2004, e-pub. Oct. 23, 2004). "Redox Inactivation of Human 15-Liopsygenase by Marine-Derived Meroditerpenes and Synthetic Chromanes: Archetypes for a Unique Class of Selective and Recyclable Inhibitors," *Journal of the American Chemical Society* 126(45):14910-14920.

Cohen, N. et al. (1981). "Studies on the Total Synthesis of (2R,4'R,8'R)-α-Tocopherol (Vitamin E). Stereospecific Cyclizations Leading to Optically Active Chromans," *The Journal of Organic Chemistry* 46(12):2445-2450.

Cornwell, D.G. et al. (1998). "Cytotoxicity of Tocopherols and Their Quinones in Drug-Sensitive and Multidrug-Resistant Leukemia Cells," *Lipids* 33(3):295-301.

Cressman, H.W. et al. (1966). "One-Step Synthesis of Polyalkyl-2-lodo-p-Benzoquinones," *Journal of Organic Chemistry* 31(4):1297-1281.

Donato, S.D. et al. (2001). "The Complex Clinical and Genetic Classification of Inherited Ataxias. II. Autosomal Recessive Ataxias," *Neurol. Sci.* 22:219-228.

Dowd, P. et al. (Aug. 1995). "On the Mechanism of the Anticlotting Action of Vitamin E Quinone," *Proceedings of the National Academy of Science* 92:8171-8175.

Dürckheimer, W. et al. (Oct. 20, 1964). "The Chemistry of 9-Hydroxy-α-Tocopherone, a Quinone Hemiacetal," *Journal of the American Chemical Society* 86(20):4388-4393.

Echtay, K.S. et al. (Nov. 30, 2000). "Coenzyme Q is an Obligatory Cofactor for Uncoupling Protein Function," *Nature* 408:609-613.

Erhola, M. et al. (Jun. 9, 1997). "Biomarker Evidence of DNA Oxidation in Lung Cancer Patients: Association of Urinary 8-Hydroxy-2'-Deoxyguanosine Excretion with Radiotherapy, Chemotherapy, and Response to Treatment," *FEBS Letters* 409(2):287-291.

Eurasian Search Report with English translation of third citation, for Eurasian Patent Application No. 200702622, filed on Jun. 1, 2006, 3 pages.

European Search Report dated Jun. 10, 2009, for EP Patent Application No. 06784530.5, filed on Jun. 1, 2006, 7 pages.

Examination Report dated Feb. 4, 2010, for EP Patent Application No. 07751472.7, filed on Oct. 8, 2009, 4 pages.

Extended European Search Report dated Apr. 14, 2011, for EP Patent Application No. 10015055.6, filed on Feb. 22, 2007, 8 pages.

Extended European Search Report dated May 16, 2012, for EP Patent Application No. 12162555.2, filed on Jun. 1, 2006, 7 pages.

Fabrizi, G.M. et al. (Apr. 1996). "Autosomal Dominant Limb Girdle Myopathy with Ragged-Red Fibers and Cardiomyopathy: A Pedigree Study by In Vivo $^{31}$P-MR Spectroscopy Indicating a Multisystem Mitochondrial Defect," *Journal of the Neurological Sciences* 137(1):20-27.

Fieser, L.F. et al. (Sep. 1942). "Alkylation of Para Quinones with Acyl Peroxides," *Journal of the American Chemical Society* 64:2060-2065.

Final Office Action dated Oct. 20, 2009, for U.S. Appl. No. 10/941,126, filed Sep. 15, 2004, 12 pages.

Final Office Action dated Dec. 29, 2010, for U.S. Appl. No. 10/941,126, filed Sep. 15, 2004, 11 pages.

Final Office Action dated Jan. 6, 2011, for U.S. Appl. No. 11/445,582, filed Jun. 1, 2006, 7 pages.

Final Office Action dated Oct. 19, 2011, for U.S. Appl. No. 11/710,042, filed Feb. 22, 2007, 6 pages.

Fujishima, T. et al. (1996, e-pub. Sep. 23, 2006). "Synthesis of Vitamin E Analogues: Possible Active Forms of Vitamin E," *Arch. Pharm. Pharma. Med. Chem.* 329(1):27-34.

Gille, L. et al. (2001). "Effects of Tocopheryl Quinone on the Heart: Model Experiments with Xanthine Oxidase, Heart Mitochondria, and Isolated Perfused Rat Hearts," *Free Radical Biology and Medicine* 30(8):865-876.

Gille, L. et al. (2004). "Oxidized Vitamin E and Ubiquinone: Competition for Binding Sites of the Mitochondrial Cytochrome bc1 Complex?" *Annals of the New York Academy of Sciences* 1031:341-343.

Gille, L. et al. (2004). "Redox-Interaction of α-Tocopheryl Quinone with Isolated Mitochondrial Cytochrome bc1 Complex," *Biochemical Pharmacology* 68:373-381.

Gille, L. et al. (2010). "Tocopheryl Quinones and Mitochondria," *Mol. Nutr. Food Res.* 54:1-15.

Goodhue, C.T. et al. (May 1965). "Reactions of Vitamin E with Peroxides. II. Reaction of Benzoyl Peroxide with d-α-Tocopherol in Alcohols," *Biochemistry* 4(5):854-858.

Green, J. et al. (1966) "Bond Stabilisation in Tocopherols. Part I. The Claisen Rearrangement of Allyl Tocopheryl Ethers," *Journal of the Chemical Society C*, pp. 1422-1427.

Gu, L. et al. (1990). "Synthesis and Inhibitory Activity of Bromoquinone Derivatives," *Tetrahedron* 46(9):3199-3210.

Gu, L-Q. et al. (1990). "Effect of Substituents of the Benzoquinone Ring on Electron-Transfer Activities of Ubiquinone Derivatives," *Biochimica et Biophysica Acta* 1015(3):482-492.

Hagio, K. et al. (Apr. 1974). "Synthesis and Reactions of 4-Dimethylsulfuranylidene-2,3,-Dioxotetrahydrofuran Derivatives," *Bulletin of the Chemical Society of Japan* 47(4):909-916.

Han, J. (2006). "Advances in Characterization of Pharmaceutical Hydrates," *Trends in Bio/Pharmaceutical Industry* 3:25-29.

Hendlin, D. et al. (Apr. 1960) "The Activity of Coenzyme $Q_{10}$ and Its Analogues in the Succinoxidase System of Electron Transport Particles," *Journal of Biological Chemistry*, 235(4):1187-1191.

Hodgkiss, R.J. et al. (May 1989). "The Effect of α-tocopherol and α-tocopheryl Quinone on the Radiosensitivity of Thiol-Depleted Mammalian Cells," *International Journal of Radition Oncology, Biology, Physics* 16(5):1297-1300.

Honda, M. et al. (Jun. 2000). "Correlation of Urinary 8-Hydroxy-2'-Deoxyguanosine (8-OHdG), a Biomarker of Oxidative DNA

(56) References Cited

OTHER PUBLICATIONS

Damage, and Clinical Features of Hematological Disorders: A Pilot Study," *Leukemia Research* 24(6):461-468.

Hübscher, J.V. et al. (1990). "Total Synthesis of Naturally Occurring α-Tocopherol. Asymmetric Alkylation and Asymmetric Epoxidation as Means to Introduce (R)-Configuration at C(2) of the Chroman Moiety," *Helvetica Chimica Acta* 73(4-6):1068-1086 (English Translation of Abstract Only).

Infante, J.P. (1999). "A Function for the Vitamin E Metabolite α-Tocopherol Quinone as an Essential Enzyme Cofactor for the Mitochondrial Fatty Acid Desaturases," *The FEBS Letters* 446:1-5.

Inoue, S. et al. (1987). "Improved General Method of Ortho Alkylation of Phenols Using Alkyl Isopropyl Sulfide, Sulfryl Chloride, and Triethylamine. An Expedient Synthesis of Representative Oxygen Heterocycles and (2R,4'R,8'R)-α-Tocopherol," *Journal of Organic Chemistry* 52:5495-5497.

International Search Report dated Feb. 8, 2007, for PCT Patent Application No. PCT/US2006/036052 filed on Sep. 15, 2006, 5 pages.

International Search Report dated Mar. 14, 2007, for PCT Patent Application No. PCT/US2006/021295 filed Jan. 6, 2006, 10 pages.

International Search Report dated May 30, 2008, for PCT Patent Application No. PCT/US2007/004713, filed on Feb. 22, 2007, 7 pages.

James, A.M. et al. (Jun. 3, 2005). "Interactions of Mitochondria-Targeted and Untargeted Ubiquinones with the Mitochondrial Respiratory Chain and Reactive Oxygen Species," *The Journal of Biological Chemistry* 280(22):21295-21312.

Jauslin, M.L. et al. (2002). "A Cellular Model for Friedreich Ataxia Reveals Small-Molecule Glutathione Peroxidase Mimetics as Novel Treatment Strategy," *Human Molecular Genetics* 11(24):3055-3063.

Jauslin, M.L. et al. (Oct. 2003, e-pub. Aug. 15, 2003). "Mitochondria-Targeted Antioxidants Protect Friedreich Ataxia Fibroblasts from Endogenous Oxidative Stress more Effectively than Untargeted Antioxidants," *The FASEB Journal* 17(13):1972-1974.

Kamat, J.P. et al. (1995). "Tocotrienols from Pal Oil as Potent Inhibitors of Lipid Preoxidation and Protein Oxidation in Rat Brain Mitochondria," *Neurosci. Lett.* 195:179-182. (14.00).

Kaufmann, P. et al. (Apr. 27, 2004). "Cerebral Lactic Acidosis Correlates with Neurological Impairment in MELAS," *Neurology* 62(8):1297-1302.

Kelso, G.F. et al. (Feb. 16, 2001)"Selective Targeting of a Redox-Active Ubiquinone to Mitochondria Within Cells," *The Journal of Biological Chemistry* 276(7):4588-4596.

Kim, J.Y. et al. (May 2004). "Urinary 8-Hydroxy-2'-Deoxyguanosine as a Biomarker of Oxidative DNA Damage in Workers Exposed to Fine Particulates," *Environmental Health Perspectives* 112(6):666-671.

Kumadaki, I. et al. (1989). "Trifluoromethylation of Tocopherols," *Synthetic Communications* 19(1&2):173-177.

Kunitsa, N.I., et al. (Nov., 1993). "Effects of Tocopherol and its Analogs on in vivo Lipid Peroxidation and Electron Transport in Rat Liver Mitochondria," *Biochemistry (Moscow) An International Journal* 58(11):1256-1259.

Larisch, B. et al. (Jul. 1996). "Reactions of Dehydroascorbic Acid with Primary Aliphatic Amines Including $N^\alpha$ -Acetyllysine," Journal of Agricultural and Food Chemistry 44(7):1630-1634.

Lenaz, G. et al. (2000). "Mitochondrial Bioenergetics in Aging," *Biochimica et Biophysica Acta* 1459:397-404.

Lipshutz, B.H. et al. (Feb. 12, 1998). "An Expeditious Route to $CoQ_n$, Vitamins $K_1$ and $K_2$, and Related Allylated para-Quinones Utilizing Ni(0) Catalysis," *Tetrahedron* 54(7):1241-1253.

Lodi, R. et al. (2001). "Antioxidant Treatment Improves In Vivo Cardiac and Skeletal Muscle Bioenergetics in Patients with Friedreich's Ataxia," *Annals of Neurology* 49:590-596.

Lynch, D.R. et al. (May 2002). "Near Infrared Muscle Spectroscopy in Patients with Friedreich's Ataxia," *Muscle & Nerve* 25(5):664-673.

Mackenzie, J.B. et al. (1950). "The Biological Activity of α-Tocopherylhydroquinone and α-Tocopherylquinone," *Journal of Biological Chemistry* 183(2):655-662.

Maloney, D.J. et al. (2005, e-pub. Aug. 20, 2005). "A Stereocontrolled Synthesis of δ-trans-Tocotrienoloic Acid," *Organic Letters* 7(19):4297-4300.

Marpat Accession No. 138:187513, 2 pages. (English Language Abstract Counterpart for JP 2003-64017).

Matthews, P.M. et al. (Apr. 1991). "In Vivo Magnetic Resonance Spectroscopy of Brain and Muscle in a Type of Mitochondrial Encephalomyopathy (MERRF)," *Annals of Neurology* 29(4):435-438.

Mazzini, F. et al. (2005, e-pub. Nov. 30, 2004). "Easy Route to Labeled and Unlabeled R,R,R,-γ-Tocopherol by Aryl Demethylation of α-Homologues," *Tetrahedron* 61:813-817.

Monte, W. T. et al. (May/Jun. 2001). "An Efficient Process for the Synthesis of γ-Arylbutanals via Copper-Mediated Grignard Coupling," *Organic Process Research & Development* 5(3):267-269.

Moore, A.N.J. et al. (1997). "60 -Tocopheryl Quinone is Converted into Vitamin E in Man," *Free Radical Biology & Medicine* 22(5):931-934.

Mukai, K. et al. (1989). "Synthesis and Kinetic Study of Antioxidant Activity of New Tocopherol (Vitamin E) Compounds," *The Journal of Organic Chemistry* 54(3):552-556.

Mukai, K. et al. (1989). "Synthesis and Stopped-Flow Investigation of Antioxidant Activity of Tocopherols. Finding of New Tocopherol Derivatives Having the Highest Antioxidant Activity Among Phenolic Antioxidants," *The Journal of Organic Chemistry* 54(3):557-560.

Mukai, K. et al. (1991). "Structure-Activity Relationship in the Quenching Reaction of Singlet Oxygen by Tocopherol (Vitamin E) Derivatives and Related Phenols. Finding of Linear Correlation Between the Rates of Quenching of Singlet Oxygen and Scavenging of Peroxyl and Phenoxyl Radicals in Solution," *The Journal of Organic Chemistry* 56(13):4188-4192.

Munnich, A. et al. (1992). "Clinical Aspects of Mitochondrial Disorders," *Journal of Inherited Metabolic Disease* 15(4):448-455.

Myagkov, I.V. (Sep.-Oct. 1985). "Monomolecular Films of Octadecyl-Substituted Quinone and Hydroquinone and Their Charge-Transfer Complexes," *Colloid Journal of the USSR* 47(5):833-836.

Non-Final Office Action dated Aug. 20, 2008, for U.S. Appl. No. 10/941,126, filed Sep. 15, 2004, 7 pages.

Non-Final Office Action dated Mar. 31, 2009, for U.S. Appl. No. 10/941,126, filed Sep. 15, 2004, 14 pages.

Non-Final Office Action dated Mar. 17, 2010, for U.S. Appl. No. 10/941,126, filed Sep. 15, 2004, 6 pages.

Non-Final Office Action dated Jun. 23, 2010, for U.S. Appl. No. 11/445,582, filed Jun. 1, 2006, 12 pages.

Non-Final Office Action dated Jun. 30, 2010, for U.S. Appl. No. 10/941,126, filed Sep. 15, 2004, 8 pages.

Non-Final Office Action dated Jan. 21, 2011, for U.S. Appl. No. 11/710,042, filed Feb. 22, 2007, 6 pages.

Non-Final Office Action dated Aug. 9, 2011, or U.S. Appl. No. 10/941,126, filed Sep. 15, 2004, 10 pages.

Omura, K. (1989). "Iodine Oxidation of α-Tocopherol and Its Model Compound in Alkaline Methanol: Unexpected Isomerization of the Product Quinone Monoketals," *The Journal of Organic Chemistry* 54(8):1987-1990.

Packer, L. et al. (2001). "Symposium: Molecular Mechanisms of Protective Effects of vitamin E in Atherosclerosis, Molecular Aspects of α-Tocotrienol Antioxidant Action and Cell Signalling," *The Journal of Nutrition* 131:369S-373S.

Patani, G.A. et al. (1996). "Bioisosterism: A Rational Approach in Drug Design," *Chem. Rev.* 96:3147-3176.

Pelter, A. et al. (1993). "Phenolic Oxidations with Phenyliodonium Diacetate," *Journal of the Chemical Society, Perkin Transactions* 1 16:1891-1896.

Pelter, A. et al. (1997). "The Synthesis of 8a-Methoxy-2H,6H-Chromen-6-ones and Corresponding 2H-Chromenes by a Unique Process Utilising Phenolic Oxidation," *Tetrahedron* 53(11):3879-3916.

(56) References Cited

OTHER PUBLICATIONS

Pileni, M-P. et al. (Apr. 15, 1980). "Zinc-Porphyrin Sensitized Reduction of Simple and Functional Quinones in Vesicle Systems," *Chemical Physics Letters* 71(2):317-321.

Pileni, M.P. et al. (1980). "Zinc Porphyrin Sensitized Reduction of Simple and Functional Quinones in Micellar Systems," *Journal of Physical Chemistry* 84(14):1822-1825.

Pilger, A. et al. (Sep. 2001). "Longitudinal Study of Urinary 8-Hydroxy-2'-Deoxyguanosine Excretion in Healthy Adults," *Free Radical Research* 35(3):273-280.

Piña, I.L. et al. (Mar. 4, 2003). "Exercise and Heart Failure: A Statement From the American Heart Association Committee on Exercise, Rehabilitation, and Prevention," *Circulation* 107(8):1210-1225.

Rolfe, P. (2000). "In Vivo Near-Infrared Spectroscopy," *Annual Review of Biomedical Engineering* 2:715-754.

Shi, J-L. et al. (1996). "Hydrophobic Acceleration of Electron Transfer Processes," *Journal of Organic Chemistry* 61(14):4698-4702.

Shiraishi, M. et al. (Sep. 1989). "Quinones. 4. Novel Eicosanoid Antagonists: Synthesis and Pharmacological Evaluation," *Journal of Medicinal Chemistry* 32(9):2214-2221.

Siegel, D. et al. (1997). "The Reduction of α-Tocopherolquinone by Human NAD(P)H: Quinone Oxidoreductase: The Role of α-Tocopherolhydroquinone as a Cellular Antioxidant," *Molecular Pharmacology* 53:300-305.

Silbert, L.S. et al. (Jun. 2, 1959). "Peroxides. VI. Preparation of t-Butyl Peresters and Diacyl Peroxides of Aliphatic Monobasic Acids," *Journal of the American Chemical Society* 81(10): 2364-2367.

Soll, H-J. et al. (Aug. 1-6, 1983). "Inhibitor Binding and Displacement in Plastoquinone Depleted Chloroplasts," *Advances in Photosynthesis Research, Proceedings of the International Congress of Photosynthesis*, Brussels, Belgium 4:5-8.

Spoyalov, A.P. et al. (1992). "ENDOR and ESEEM Studies of Ion Radicals of Artificial Dimethoxy- or Halogen-1,4-benzoquinones with an Alkyl Side Chain of Differing Length," *Journal of the Chemical Society, Perkin Transactions* 2, pp. 1519-1524.

Staniek, K. et al. (Nov. 1, 2005). "The Protection of Bioenergetic Functions in Mitochondria by New Synthetic Chromanols," *Biochemical Pharmacology* 70(9):1361-1370.

Stella, V.J. et al. (2007). "Prodrugs: Challenges and Rewards, Part I," *Biotechnology: Pharmaceutical Aspects* 1(1):24.

STN Accession No. 1985:621368, last visited Jan. 23, 2007, 1 page.
STN Accession No. 1992:58878, last visited Jan. 23, 2007, 1 page.
STN Accession No. 1993:21870, last visited Jan. 23, 2007, 2 pages.

Strangman, G. et al. (Oct. 1, 2002). "Non-Invasive Neuroimaging Using Near-Infrared Light," *Biological Psychiatry* 52(7):679-693.

Taivassalo, T. et al. (Jan. 2002, e-pub. Nov. 15, 2001). "Venous Oxygen Levels During Aerobic Forearm Exercise: An Index of Impaired Oxidative Metabolism in Mitochondrial Myopathy," *Annals of Neurology*. 51(1):38-44.

Taivassalo, T. et al. (Feb. 2003). "The Spectrum of Exercise Tolerance in Mitochondrial Myopathies: A Study of 40 Patients," *Brain* 126(Pt2)413-423.

Thomas, A.D. et al. (Aug. 8, 1986). "Repetitive Diels-Alder Reactions for the Growth of Linear Polyacenequinoid Derivatives," *Journal of Organic Chemistry* 51(22):4160-4169.

Timochko, M.F. et al. (1998). "Metabolic Aspects of Oxygen Homeostasis Formation Under Extreme Conditions," with English translation of paragraph 5 on p. 7, L'vov, located at <http://posrednik.ru/tren/tim_sv.htm>, last visited on Sep. 29, 2008, 52 pages.

Trumpower, B.L. (Jul. 15, 1990). "The Protonmotive Q Cycle. Energy Transduction by Coupling of Proton Translocation to Electron Transfer by Cytochrome $bc_1$ Complex," *The Journal of Biological Chemistry* 265(20):11409-11412.

Ueda, K. et al. (Feb. 1997). "Evaluation of Changes in Hepatic Energy Metabolism during Exercise by Ketone Body Ration in Humans," *Journal of Cardiology* 29(2):95-102 (English Translation of Abstract Only).

Van Beekvelt, M.C.P. et al. (Oct. 1999). "Quantivative Near-Infared Spectroscopy Discriminates Between Mitochondrial Myopathies and Normal Muscle," *Annals of Neurology* 46(4):667-670.

Vatassery, G. et al. (Apr. 5, 2004). "Iron Uncouples Oxidative Phosphorylation in Brain Mitochondria Isolated From Vitamin E-Deficient Rats," *Biochimica et Biophysica Acta* 1688(3):265-273.

Vippagunta, S.R. et al. (2001). "Crystalline Solids," *Advanced Drug Delivery Reviews* 48:3-26.

Walter, L. et al. (Sep. 22, 2000). "Three Classes of Ubiquinone Analogs Regulate the Mitochondrial Permeability Transition Pore Through a Common Site," *The Journal of Biological Chemistry* 275(38):29521-29527.

Warner, S.A. et al. (May 1, 1983). "Synthesis and Metabolism of α-Tocopherol Quinone in Normal and Diabetic Mouse Liver," *Federation Proceedings, American Society of Biological Chemists*, $74^{th}$ *Annual Meeting*, San Francisco, CA, Jun. 5-9, 1983, 42(7):1919, Abstract No. 944.

Weichet, J. et al. (1996). "Vitamin K and Vitamin E Series. XVIII. Synthesis of New Analogs of Vitamin E and Their Derivatives," *Collection of Czeckoslov. Chem. Commun.* 31:4598-4609.

Written Opinion dated Feb. 8, 2007, for PCT Patent Application No. PCT/US2006/036052 filed on Sep. 15, 2006, 10 pages.

Written Opinion dated Mar. 14, 2007, for PCT Patent Application No. PCT/US2006/021295 filed on Jan. 6, 2006, 10 pages.

Written Opinion dated May 30, 2008, for PCT Patent Application No. PCT/US2007/004713, filed on Feb. 22, 2007, 10 pages.

Yamauchi, R. et al. (1990). "Reaction Products of γ-Tochopherol with an Alkylperoxyl Radical in Benzene," *Agricultural and Biological Chemistry* 54(10):2703-2709.

Yamauchi, R. et al. (1990). "Reaction of δ-Tocopherol with an Alkylperoxyl Radical," *Agricultural and Biological Chemistry* 54(11):2993-2999.

Yamauchi, R. et al. (1996). "Oxidation of α-Tocopherol during the Peroxidation of Dilinoleoylphosphatidylcholine in Liposomes," *Bioscience, Biotechnology, and Biochemistry* 60(4):616-620.

Zheng, A. et al. (1999). "A Redox-Sensitive Resin Linker for the Solid Phase Synthesis of C-Terminal Modified Peptides," *Journal of Organic Chemistry* 64:156-161.

Zwaiyed, F.R. et al. (2003). "Vitamin E and its Derivative Antihypoxic Effectivity in Rats Under Modeling of Hypoxic Conditions of Different Origin," *Ukrainskii Biokhimicheskii Zhurnal* 75(2):67-71.

Zwaiyed, F.R. et al. (2003). "Antihypoxic Effect of Vitamin E and a Derivative Thereof in a Rat Model of Hypoxic States of Different Origins," *Ukrainskii Biokhimicheskii Zhurnal* 75(2):67-71. (English translation).

Chow, C.K. et al. (Sep. 1967). "The Metabolism of $C^{14}$-α-Tocopheryl Quinone and $C^{14}$-α-Tocopheryl Hydroquinone," *Lipids* 2(5):390-396.

Anonymous (Feb. 2010). "List of Publications Noting Mitochondrial Involvement in Diseases," 3 Pages.

Anonymous. (2006). "Mitochondrial Dysfunction Contribution to Bipolar Disorder Confirmed Using Model Mice," Press Release from Riken Brain Science Institute located at http://web.archive.org/web/20120303I6199/http://www.riken.jp/engn/r-world/infor/pressrelease/press/2006/060418/index.html, last visited Feb. 10, 2015, 5 pages.

Anonymous. (2011). "Mitochondrial Myopathy," located at http://www.ninds.nih.gov/disorders/mitochondrial_myopathy/mitochondrial_myopathy.html, last visited Feb. 10, 2015, 2 pages.

Bertamini, M. et al. (2002). "Mitochondrial Oxidative Metabolism in Motor Neuron Degeneration (mnd) Mouse Central Nervous System," *European Journal of Neuroscience* 16(12):2291-2296.

Brigelius-Flohe et al., Vitamin E: function and metabolism, FASEB J. Jul. 1999: 13(10):1145-55.

Calabresi et al., "Section IX Chemotherapy of Neoplastic Diseases—Introduction," Goodman & Gilman's The Pharmacological Basis of Therapeutics 10th ed., 2001, Hardman 2001, 1381-1388 (pp. 1381, 1383-1385, and 1388 provided).

Canter, J.A. et al. (May 2008). "Mitochondrial DNA Polymorphism A4917G Is Independently Associated with Age-Related Macular Degeneration," *PloS One* 3(5):e2091, 4 pages.

Final Office Action dated Jul. 3, 2013, for U.S. Appl. No. 12/777,179, filed May 10, 2010, 5 pages.

(56) References Cited

OTHER PUBLICATIONS

Gellerich, F.N. et al. (e-pub. Jul. 7, 2008). "Impaired Regulation of Brain Mitochondria by Extramitochondrial $Ca^{2+}$ in Transgenic Huntington Disease Rats," *Journal of Biological Chemistry* located at http://www.jbc.org.cgi/doi/10.1074/jbc.M709555200, last visited Feb. 10, 2015, 23 pages.

Gerbitz, K-D. et al. (Feb. 1996). "Mitochondria and Diabetes: Genetic, Biochemical, and Clinical Implications of the Cellular Energy Circuit," *Diabetes* 45(2):113-136.

Hauptmann, S. et al. (2009, e-pub. Mar. 4, 2008). "Mitochondrial Dysfunction: An Early Event in Alzheimer Pathology Accumulates With Age in AD Transgenic Mice," *Neurobiology of Aging* 30:1574-1586.

Karry, R. et al. (2004). "Mitochondrial Complex I Subunits Expression Is Altered in Schizophrenia: A Postmortem Study," *Biological Psychiatry* 55(7):676-684.

Keeney, P.M. et al. (May 10, 2006). "Parkinson's Disease Brain Mitochondrial Complex I Has Oxidatively Damaged Subunits and Is Functionally Impaired and Misassembled," *The Journal of Neuroscience* 26(19):5256-5264.

Khan, S.Z. (2006). "Mitochondrial Complex-1 in Parkinson's Disease," Neurology India located at http://www.neurologyindia.com/article.asp?issn=0028-3886;year=2006;volume=54;is . . . , last visited Feb. 10, 2015.

Klivenyi et al., Alpha-Tocopherol/lipid ratio in blood is decreased in patients with Leber's hereditary optic neuropathy and asymptomatic carriers of the 11778 mtDNA mutation. J. Neurol Neurosurg Psychiatry. Mar. 2001; 70(3):359-62.

Kunz, W.S. et al. (2004). "The Role of Mitochondria in Epilepsy: Implications for Neurodegenerative Diseases," *Toxicology Mechanisms and Methods* 14:19-23.

Kunz, W.S. et al. (Nov. 2000). "Mitochondrial Complex I Deficiency in the Epileptic Focus of Patients with Temporal Lobe Epilepsy," *Annals of Neurology* 48(5):766-773.

Lamson, D.W. (2002). "Mitochondrial Factors in the Pathogenesis of Diabetes: A Hypothesis for Treatment—Mitochondial Factors/Diabetes," *Alternative Medicine Review* 7(2):94-111.

Lowell, B. (Jan. 21, 2005). "Mitochondrial Dysfunction and Type 2 Diabetes," *Science* 307(5708):384-387.

Lustbader, J.W. et al. (Apr. 16, 2004). "ABAD Directly Links Aβ to Mitochondrial Toxicity in Alzheimer's Disease," *Science* 304(5669):448-452.

Mann, V.M. et al. (1992). "Brain, Skeletal Muscle and Platelet Homogenate Mitochondrial Function in Parkinson's Disease," *Brain* 115:333-342.

Niaudet, P. et al. (1996). "Renal Involvement in Mitochondrial Cytopathies," *Pediatric Nephrol.* 10(3):368-373.

Non-Final Office Action dated Oct. 26, 2012, for U.S. Appl. No. 12/777,179, filed May 10, 2010, 5 pages.

Oliveira, J.M.A. et al. (2007). "Mitochondrial Dysfunction in Huntington's Disease: The Bioenergetics of Isolated and in situ Mitochondria from Transgenic Mice," *Journal of Neurochemistry* 101(1):241-249.

Van Haaften, R.I.M. et al. (Mar. 15, 2001). "No Reduction of α-Tocopherol Quinone by Glutathione in Rat Liver Microsomes," *Biochemical Pharmacology* 61(6):715-719.

Wang, J-F. (Dec. 2007). "Defects of Mitochondrial Electron Transport Chain in Bipolar Disorder: Implications for Mood-Stabilizxing Treatment," *The Canadian Journal of Psychiatry* 52(12):753-762.

Wrobel, S. (Apr. 7, 2008). "Mitochondria Play Role in Pathogenesis of Alzheimer's Disease and Estrogen-Induced Neuroprotection," *Experimental Biology* located at http://www.medicalnewstoday.com/releases/102971.php, last visited Feb. 10, 2015, two pages.

Yang, S.-G. et al. (Dec. 2010, e-pub. Oct. 7, 2010). "Alpha-Tocopherol Quinone Inhibits Beta-Amyloid Aggregation and Cytotoxicity, Disaggregates Preformed Fibrils and Decreases the Production of Reactive Oxygen Species, NO and Inflammatory Cytokines," *Neurochemistry International* 57(8):914-922.

Alexander, C. et al. (Oct. 2000). "OPA1, Encoding a Dynamin-Related GTPase, is Mutated in Autosomal Dominant Optic Atrophy Linked to Chromosome 3q28," *Nature Genetics* 26(2):211-215.

Armstrong, J.S. et al. (Dec. 5, 2003). "The Coenzyme Q10 Analog Decylubiquinone Inhibits the Redox-Activated Mitochondrial Permeability Transition," *The Journal of Biological Chemistry* 278(49):49079-49084.

Biousse, et al. (Feb. 2003). "Neuro-Ophthalmology of Mitochondrial Diseases," *Current Opinion in Neurology* 16(1):35-43.

Bremner, F.D. (2004). "Pupil Assessment in Optic Nerve Disorders," *Eye* 18:1175-1181.

Brown, M.D. et al. (Jul. 1992). "Leber's Hereditary Optic Neuropathy: A Model for Mitochondrial Neurodegenerative Diseases," *The FASEB Journal* 6:2791-2799.

Catlin, J.C. et al. (Jun. 19, 1968). "New Hydroquinones, Apparent Inhibitors of Coenzyme Q Enzyme Systems", Journal of the American Chemical Society, pp. 3572-3574, XP55065560, located at URL:http://pubs.acs.org/doi/pdf/10.1021/ja01015a054, last visited Jun. 6, 2013.

Carelli, V. (2002). "Optic Nerve Degeneration and Mitochondrial Dysfunction: Genetic and Acquired Optic Neuropathies," *Neurochemistry International* 40:573-584.

Carelli, V. et al. (2009, e-pub. Mar. 5, 2009). "Retinal Ganglion Cell Neurodegeneration in Mitochondrial Inherited Disorders," *Biochimica et Biophysica Acta* 1787:518-528.

Csaky, K.G. (Mar./Apr. 2007). "New Developments in the Transscleral Delivery of Ophthalmic Agents," *Retina Today*, pp. 32-35.

Delettre, C. et al. (Oct. 2000). "Nuclear Gene OPA1, Encoding a Mitochondrial Dynamin-Related Protein, is Mutated in Dominant Optic Atrophy," *Nature Genetics* 26(2):207-210.

Extended European Search Report dated Jun. 17, 2013, for EP Patent Application No. 13163798.5, filed on Feb. 22, 2007, 11pages.

Extended European Search Report dated Jun. 25, 2013, for EP Patent Application No. 13163805.8, filed on Feb. 22, 2007, 13pages.

Extended European Search Report dated Oct. 11, 2013, for EP Patent Application No. 11775506.6, filed on Apr. 26, 2011, 7 pages.

Final Office Action dated Oct. 24, 2014, for U.S. Appl. No. 13/643,542, filed Nov. 26, 2012, 6 pages.

Final Office Action dated Feb. 25, 2015, for U.S. Appl. No. 11/445,582, filed Jun. 1, 2006, 12 pages.

Ghate, D. et al. (May 2007). "Pharmacokinetics of Intraocular Drug Delivery by Periocular Injections Using Ocular Fluorophotometry," *Investigative Ophthalmology and Visual Science* 48(5):2230-2237.

Gouw, L.G. et al. (May 1995). "Retinal Degeneration Characterizes a Spinocerebellar Ataxia Mapping to Chromosome 3p," *Nature Genetics* 10:89-93.

Grönlund, M.A. et al. (2010). "Ophthalmological Findings in Children and Young Adults with Genetically Verified Mitochondrial Disease," Br. J. Ophthalmol. 94:121-127.

Gu, L. et al. (1991). "Synthesis, Oxidation-Reduction Potentials and Biological Activity of 1,4-Benzoquinone Derivatives," Youji Huaxue 11(5):481-487. (EnglishTranslation of Abstract Only).

Gubskii, Y.I. et al. (2008). "Antioxidant and Membranotropic Effects of Monochromanes and Trimethylphenol Derivatives in Vitro," Ukrains'kii Biokhimichnii Zhurnal 80(6):79-85, Chemical Abstract Only, Caplus Abstract No. 2009:267923.

Gupta, S.N. et al. (Jan. 15, 2008, e-pub. Aug. 27, 2007). "Spinocerebellar Ataxia Type 7 Mimicking Kearns-Sayre Syndrome: A Clinical Diagnosis is Desirable," Journal of Neurological Sciences 264:173-176.

Haas, R.H. et al. (May 2008). "The In-Depth Evaluation of Suspected Mitochondrial Disease: The Mitochondrial Medicine Society's Committee on Diagnosis," Mol. Genet. Metab. 94(1):16-37, 32 pages.

Huang, C-C. et al. (Mar. 2002). "Rapid Visual Recovery After Coenzyme Q10 Treatment of Leber Hereditary Optic Neuropathy," *The Journal of Neuro-Opthalmology* 22(1):66-67.

Hudson, G. et al. (Jul. 2008). "Leber Hereditary Optic Neuropathy," Expert Opinion on Medical Diagnostics 2(7):789-799.

International Preliminary Report on Patentability dated Nov. 1, 2011, for PCT Patent Application No. PCT/US2010/032621, filed on Apr. 27, 2010, 6 pages.

(56) References Cited

OTHER PUBLICATIONS

International Preliminary Report on Patentability dated Nov. 1, 2011, for PCT Patent Application No. PCT/US2010/032624, filed on Apr. 27, 2010, 7pages.
International Preliminary Report on Patentability dated Oct. 30, 2012 for PCT Patent Application No. PCT/US2011/033983 filed on Apr. 26, 2011, 6 pages.
International Search Report dated Jul. 8, 2010, for PCT Patent Application No. PCT/US2010/032624, filed on Apr. 27, 2010, 4 pages.
International Search Report dated Jul. 19, 2010, for PCT Patent Application No. PCT/US2010/032621, filed on Apr. 27, 2010, 4 pages.
International Search Report dated Jul. 13, 2011, for PCT Patent Application No. PCT/US11/33983, filed on Apr. 26, 2011, 2 pages.
Jarrett, S.G. et al. (2008). "Mitochondrial DNA Damage and Its Potential Role in Retinal Degeneration," Progress in Retinal and Eye Research 27:596-607.
Jung, M E et al (Aug. 27, 1999). "First Enantioselective Total Synthesis of the Endogenous Natriuretic Agent LLU-Alpha", Tetrahedron Letters, 40(25):6339-6342, XP004173857, ISSN: 0040-4039, DOI: 10.1016/S0040-4039(99)01204-6.
Kajiwara, M. et al. (1980). "Studies on Tocopherols II1. Convenient Synthesis of Tocopherols," Heterocycles 14(12):1995-1998.
Kirkman, M.A. (Jul. 2009). "Quality of Life in Patients with Leber Hereditary Optic Neuropathy," Investigative Ophthalmology & Visual Science 50(7):3112-3115.
Kosmorsky, G. et al. (Feb. 1991). "Neuro-Ophthalmologic Manifestations of Mitochondrial DNA Disorders: Chronic Progressive External Ophthalmoplegia, Kearns-Sayre Syndrome, and Leber's Hereditary Optic Neuropathy," Neurologic Clinics 9(1):147-161.
Kovalenko, V.N. et al. (1979). "Vitamin E Activity of Vitamin E Derivatives in Experimental Encephalomalacia in Chicks," Ukrainskii Biokhimicheskii Zhurnal 51(6):665-668, Chemical Abstract Only, Caplus Abstract No. 1980:74772, 1 page.
Kwong, J.Q. et al. (2006). "The Role of Mitochondria in Inherited Neurodegenerative Diseases," Journal of Neurochemistry 97:1659-1675.
Lynch,. et al. (2012; e-pub. Jun. 28, 2012). "A0001 in Friedreich Ataxia: Biochem. Characterization and Effects in a Clin. Trial," Mov. Disord. 27(8):1026-1033.
Makovetskii, V.P. et al. (1987). "Synthesis, Properties, and Detoxication Activity of α-tocopherol Analogs and Derivatives," Khimiko-Farmatsevticheskii Zhurnal 21(12):1441-1446, Chemical Abstract Only, Caplus Abstract No. 1988:142850, 2 pages.
Man, P.Y.W. et al. (2002). "Leber Hereditary Optic Neuropathy," J. Med. Genet. 39:162-169.
Mayer, H. et al. (1967). "Über die Chemie des Vitamins E. 8. Mitteilung [1]. Die Stereochemie von Natürlichem γ-Tocotrienol (Plastochromanol-3), Plastochromanol-8 und Plastochromanol-81)," Helvetica Chimica Acta 50(5):1376-1393, No. 139. (English Summary on pp. 1392-1393 and Chemical Abstract Caplus Abstract No. 1967:473698 is also included.).
Nishigaki, Y. et al. (2003). "A Novel Mitochondrial tRNALeu(UUR) Mutation in a Patient with Features of MERRF and Kearns-Sayre Syndrome," Neuromuscular Disorders 13:334-340.
Non-Final Office Action dated Aug. 6, 2014, for U.S. Appl. No. 11/445,582, filed Jun. 1, 2006, 12 pages.
Olichon, A. et al. (2006, e-pub. Apr. 20, 2006). "Mitochondrial Dynamics and Disease, OPA1," Biochimica et Biophysica Acta 1763:500-509.
Orbis. (2003). "Chronic Progressive External Opthalmoplegia," located at http://telemedicine.orbis.org/bins/volume_page.asp?cid=1-2896-5258-5381&print=true, last visited on Jun. 10, 2014, 1 page.
Pearce, B.C. et al. (1992). "Hypocholesterolemic Activity of Synthetic and Natural Tocotrienols," Journal of Medicinal Chemistry 35(20):3595-3606.
Pelak, V.S. et al. (Sep. 2004). "Neuro-Ophthalmic Manifestations of Neurodegenerative Disease," Ophthalmology Clinics of North America 17(3):311-320.
Raghava, S. et al. (2004). "Periocular Routes for Retinal Drug Delivery," Expert Opin. Drug Deliv. 1(1):99-114.
Richards, R.M.E. (2004). "Ophthalmic Products," Chapter 26 in Pharmaceutical Practice, Third Edition, Winfield, A.J.et al. eds., Churchill Livingstone, pp. 264-279.
Russo, R. et al. (2008). "Rational Basis for the Development of Coenzyme Q10 as a Neurotherapeutic Agent for Retinal Protection," Progress in Brain Research 173:575-582.
Schudel, P. et al. (1963). "Über die Chemie des Vitamins E. 5. Mitteilung. Die Synthese von rac. all-trans-ζ1-und-ε-Tocopherol, Helvetica Chimica Acta 46(7):2517-2526. (English summary on p. 2526.).
Scott, J.W. et al. (1976). "Syntheses of (2R,4'R,8'R)-α-Tocopherol and (2R,3'E,7'E)-α-Tocotrienol," Helvetica Chimica Acta 59:290-306, Nr. 34.
Tabrizi, S.J. et al. (Jul. 1998). "Primary and Secondary Deficiencies of the Mitochondrial Respiratory Chain," The Neurologist 4(4):169-179.
Tanito, M. et al. (May 2004). "Distribution of Tocopherols and Tocotrienols to Rat Ocular Tissues After Topical Ophthalmic Administration," Lipids 39(5):469-474.
Urano, S. et al. (1983). "Synthesis of dl-α-Tocopherol and dl-α-Tocotrienol," Chem. Pharm. Bull. 31(12):4341-4345.
Wakakura, M. et al. (2009). "Initial Temporal Field Defect in Leber Hereditary Optic Neuropathy," Jpn. J. Ophthalmol. 53:603-607.
Weichet, J. et al.(Jan. 19, 1966). "New Substituted Benzohydroquinones", Chemical Abstracts Service, Columbus, Ohio, US; Database CA, XP002698443, retrieved from STN Database accession No. 1968:95542.
Witting, P. K. et al.: (Jan. 1, 1996). "A Rapid and Simple Screeing Test for Potential Inhibitors of Tocopherol-Mediated Peroxidation of LDL Lipids", Journal of Lipid Research, American Society for Biochemistry and Molecular Biology, Inc, US, 27(4): 853-867, XP001095707, ISSN: 0022-2275.
Written Opinion dated Jul. 8, 2010, for PCT Patent Application No. PCT/US2010/032624, filed on Apr. 27, 2010, 6 pages.
Written Opinion dated Jul. 19, 2010, for PCT Patent Application No. PCT/US2010/032621, filed on Apr. 27, 2010, 5 pages.
Written Opinion dated Jul. 13, 2011, for PCT Patent Application No. PCT/US11/33983, filed on Apr. 26, 2011, 5 pages.
Yen, M-Y. et al. (2006). "Leber's Hereditary Optic Neuropathy: A Multifactorial Disease," Progress in Retinal and Eye Research 25:381-396.
Yu-Wai-Man, P. et al. (2009, e-pub. Nov. 17, 2008). "Inherited Mitochondrial Optic Neuropathies", J. Med. Genet. 46:145-158.
Zanna, C. et al. (2008). "OPA1 Mutations Associated with Dominant Optic Atrophy Impair Oxidative Phosphorylation and Mitochondrial Fusion," Brain 131(2):352-367.
Beers, M.H. ed. et al. (1999). "Cerebrovascular Disease," Chapter 174 in the Merck Manual of Diagnosis and Therapy, 17th Edition, Merck Research Laboratories, Whitehouse Station, NJ, pp. 1417-1424.
Bernas T. et al. (2002). "Mitochondrial and Nonmitochondrial Reduction of MTT: Interaction of MTT With TMRE, JC-1, and NAO Mitochondrial Fluorescent Probes," Cytometry 47:236-242.
Berridge M. et al. (2005). "Tetrazolium dyes as tools in cell biology: New insights into their cellular reduction," Biotechnology Annual Review 11:127-152.
Bilenko, M.V. et al. (Sep. 1983). "Use of Antioxidants to Prevent Damage During Acute Ischemia and Reperfusion of the Kidneys," Byulleten'Eksperimental'noi Biologii i Meditsiny 96(9):8-11. (Abstract only.).
Buranrat B. et al. (2012). "NQO1 Expression Correlates with Cholangiocarcinoma Prognosis," Asian Pacific J. Cancer Prev. 13:131-136.
Choi, D.W. (Oct. 1988). "Glutamate Neurotoxicity and Diseases of the Nervous System," Neuron. 1(8):623-634.
Christen, S. et al. (Apr. 1997). "γ-Tocopherol Traps Mutagenic Electrophiles Such as NOX and Complements α-Tocopherol: Physiological Implications,"Proc. Natl. Acad. Sci. USA 94(7):3217-3222.

(56) References Cited

OTHER PUBLICATIONS

Dearling, J.L.J. et al. (Mar. 2002, e-pub. Sep. 8, 2001). "Copper Bis(Thiosemicarbazone) Complexes as Hypoxia Imaging Agents: Structure-Activity Relationships," J. Biol. Inorg. Chem. 7(3):249-259.
Diener, H.C. et al. (Jan. 1996). "Lubeluzole in Acute Ischemic Stroke. A Double-Blind, Placebo-Controlled Phase II Trial," Stroke 27(1):76-81.
Duong, T.Q. (Jul. 2004). "Applications of Diffusion/Perfusion Magnetic Resonance Imaging in Experimental and Clinical Aspects of Stroke," Curr. Atheroscler Rep. 6(4):267-273.
Fahey J.W. et al. (2004). "The "Prochaska" Microtiter Plate Bioassay for Inducers of NQO1," Chapter 14 in Methods in Enzymology, Quinones and Quinone Enzymes, Part B, Sies H, ed., Elsevier Academic Press, San Diego, CA, pp. 243-258.
Flynn, C.J. et al. (1989). "Ischemia and Hypoxia," Chapter 40 in Basic Neurochemistry, 4th Edition, Siegel, G.J. ed. et al., Raven Press, New York, NY, pp. 783-795.
Fryer, M.J. (1998). "Vitamin E Status and Neurodegenerative Disease," Nutritional Neuroscience 1(5):327-351.
Fujibayashi, Y. et al. (Jul. 1997). "Copper-62-ATSM: A New Hypoxia Imaging Agent with High Membrane Permeability and Low Redox Potential," The Journal of Nuclear Medicine 38(7):1155-1160.
Fukuzawa, K. et al. (Jul. 1982). "Antioxidant Activities of Tocopherols on Fe2+-ascorbate-Induced Lipid Peroxidation in Lecithin Liposomes," Lipids 17(7):511-513.
Garn, H. et al. (1994). "An improved MTT assay using the electron-coupling agent menadione," Journal of Immunological Methods 168:253-256.
Goldberg, M.P. et al. (Nov. 1990). Intracellular Free Calcium Increases in Cultured Cortical Neurons Deprived of Oxygen and Glucose, Stroke 21(11-Suppl III):III-75-III-77.
Gonzalez, M.J. (1990). "Serum Concentrations and Cellular Uptake of Vitamin E," Medical Hypotheses 32:107-110.
Grau, A. et al. (1998). "Dissimilar Protection of Tocopherol Isomers Against Membrane Hydrolysis by Phospholipase A2," Chemistry and Physics of Lipids 91:109-118.
Grotta, J.C. et al. (1988). "Efficacy and Mechanism of Action of a Calcium Channel Blocker After Global Cerebral Ischemia in Rats," Stroke 19:447-454.
Guy, W. (1976). "CGI Clinical Global Impressions," in Early Clinical Drug Evaluation Unit (ECDEU) Assessment Manual for Psychopharmacology, U.S. Department of Health, Education, and Welfare, pp. 217-222.
Hawkins, R.D. et al. (1993). "Learning to Modulate Transmitter Release: Themes and Variations in Synaptic Plasticity," Annual Review of Neuroscience 16:625-665.
Iizuka, T. et al. (2005). "Pathogenesis of Stroke-Like Episodes in MELAS: Analysis of Neurovascular Cellular Mechanisms," Current Neurovascular Research 2(1):29-45.
Ikawa, M. et al. (2009, e-pub. Jan. 30, 2009). "PET Imaging of Redox and Energy States in Stroke-Like Episodes of MELAS," Mitochondrion 9:144-148.
Ito, H. et al. (2008). "Serial Brain Imaging Analysis of Stroke-Like Episodes in MELAS," Brain & Development 30:483-488.
Jiang, Q. et al. (Oct. 10, 2000). γ-Tocopherol and its Major Metabolite, in Contrast to α-Tocopherol, Inhibit Cyclooxygenase Activity in Macrophages and Epithelial Cells, Proceedings of the National Academy of Sciences 97(21):11494-11499.
Jones, J.W. et al. (1977). "10% Soybean Oil Emulsion as a Myocardial Energy Substrate After Ischemic Arrest," Surgical Forum 28:284-285.
Jung, M.Y. et al. (Sep. 1, 1990). "Effects of A-, Y-, and—Tocopherols on Oxidative Stability of Soybean Oil," Journal of Food Science 55(5):1464-1465.
Kanno, T. et al. (1996). "Inhibition of Neutrophil-Superoxide Generation by α-Tocopherol and Coenzyme Q," Free Radical Research 24(4):281-289.
Kapinya K. et al. (2003). "Role of NAD(P)H:quinone oxidoresuctase in the progression of neuronal cell death in vitro and following cerebral ischaemia in vivo," Journal of Neurochemistry 84:1028-1039.
Kariya, S. et al. (2005, e-pub. Mar. 10, 2005). "Humanin Detected in Skeletal Muscles of MELAS Patients: A Possible New Therapeutic Agent," Acta Neuropathol. 109:367-372.
Khanna, S. et al. (2005, e-published Sep. 15, 2005). "Neuroprotective Properties of the Natural Vitamin E α-Tocotrienol," Stroke 36:e144-e152.
Khanna, S. et al. (2014, e-published Nov. 19, 2014). "Excessive α-tocopherol exacerbates microglial activation and brain injury caused by acute ischemic stroke," The FASB Journal vol. 29, pp. 1-9.
Kim, S-O. et al. (Mar. 8, 2004). "KR-31378 Protects Neurons from Ischemia-Reperfusion Brain Injury by Attenuating Lipid Peroxidation and Glutathione Loss," European Journal of Pharmacology 487(1-3):81-91.
Kinouchi, H. et al. (Dec. 1991). "Attenuation of Focal Cerebral Ischemic Injury in Transgenic Mice Overexpressing CuZn Superoxide Dismutase," Proc. Natl. Acad. Sci. USA 88:11158-11162.
Kobayashi, M.S. et al. (2000). "Antioxidants and Herbal Extracts Protech HT-4 Neuronal Cells Against Glutamate-Induced Cytotoxicity," Free Radical Research 32(2):115-124.
Lee, P.I. (1992). "Diffusion-Controlled Matrix Systems," Chapter 3 in Treatise on Controlled Dug Delivery, Kydonieus, A. ed., Marcel Dekker, Inc., New York, NY, pp. 155-197.
Lewis, J.S. et al. (Apr. 2001). "Tumor Uptake of Copper-Diacetyl-Bis(N4-Methylthiosemicarbazone): Effect of Changes in Tissue Oxygenation," The Journal of Nuclear Medicine 42(4):655-661.
Li, H. et al., "CoQ10 fails to protect brain against focal and global ischemia in rats." Brain Res. Sep. 15, 2000; 877(1):7-11.
Macmanus, J.P. et al. (1993). "Global Ischemia Can Cause DNA Fragmentation Indicative of Apoptosis in Rat Brain," Neuroscience Letters 164:89-92.
Mishima, Tanaka T. et al. (2003) "Vitamin E isoforms alpha-tocotrienol and gamma-tocopherol prevent cerebral infarction in mice" Neurosci Lett; 337 (1) 56-60 DOI: http://www.ncbi.nlm.nih.gov/pubmed/12524170.
Molinari, G.F. (1986). "Experimental Models of Ischemic Stroke," Chapter 5 in Stroke, Pathophysiology, Diagnosis, and Management, vol. 1, Barnett, H.J.M. ed. et al., Churchill Livingstone Inc., pp. 57-73.
Neuzil, J. et al. (Oct. 1998). "α-Tocopherol in Atherogenesis: Do We Know Its Real Role?" Cardiovascular Drugs and Therapy 12(5):421-423.
Obata, A. et al. (2001). "Retention Mechanism of Hypoxia Selective Nuclear Imaging/Radiotherapeutic Agent Cu-diacetyl-bis(N4-Methylthiosemicarbazone) (Cu-ATSM) in Tumor Cells," Annals of Nuclear Medicine 15(6):499-504.
Obón J.M. et al. (1999). "Enzymatic cycling assay for D-carnitine determination," Anal Biochem. 274(1):34-9.
Ogawa et al. (Jul. 2008). Free Radical Research, vol. 42(7), pp. 674-687.
Pagliacci, M.C. et al. (1993). "Genistein Inhibits Tumor Cell Growth in vitro but Enhances Mitochondrial Reduction of Tetrazolium Salts: A Further Pitfall in the Use of the MTT Assay for Evaluating Cell Growth and Survival," Eur J. Cancer 29A(11): 1573-1577.
Paranich, A.V. et al. (1991). "Age-Related Tocopherol Content of Normal and Ischemic Heart and Liver of Rats," Fiziologicheskii Zhurnal (Kiev, 1978-1993) 37(5):16-19. (English Abstract only.).
Park, L.C.H. et al. (2000). "Metabolic Impairment Elicits Brain Cell Type—Selective Changes in Oxidative Stress and Cell Death in Culture," Journal of Neurochemistry 74(1)114-124.
Pulsinelli, W.A. (2000). "Ischemic Cerebrovascular Disease," Chapter 470 and "Hemorrhagic Cerebrovascular Disease," Chapter 471 in Cecil Textbook of Medicine, 21st Edition, Goldman, L. ed. et al., W.B. Saunders Company: Philadelphia, PA, pp. 2099-2115.
Prochaska H.J. et al. (1988). "Direct measurement of NAD(P)H:quinone reductase from cells cultured in microtiter wells: a screening assay for anticarcinogenic enzyme inducers," Anal. Biochem. 169:328-36.

(56) References Cited

OTHER PUBLICATIONS

Qureshi, A.A. et al. (2001). "Novel Tocotrienols of Rice Bran Inhibit Atherosclerotic Lesions in C57BL/6 ApoE-Deficient Mice," Journal of Nutrition 131:2606-2618.
Ricciarelli, R. et al. (1998). "α-Tocopherol Specifically Inactivates Cellular Protein Kinase C α by Changing Its Phosphorylation State," Biochem. J. 334:243-249.
Riss T. et al (2013). "Cell viability Assays," Assays Guidance Manual, 28 pages.
Saldeen, T. et al. (Oct. 1999). "Differential Effects of α- and γ-Tocopherol on Low-Density Lipoprotein Oxidation, Superoxide Activity, Platelet Aggregation and Arterial Thrombogenesis," Journal of the American College of Cardiology 34(4):1208-1215.
Sen, C.K. et al. (2007). "Tocotrienols in Health and Disease: The Other Half of the Natural Vitamin E Family," Mol. Aspects Med. 28(5-6):692-728.
Sen, C.K. et al. (Apr. 28, 2000). "Molecular Basis of Vitamin E Action. Tocotrienol Potently Inhibits Glutamate-Induced pp60c-Src Kinase Activation and Death of HT4 Neuronal Cells," The Journal of Biological Chemistry 275(17):13049-13055.
Siesjö, B.K. (1981). "Cell Damage in the Brain: A Speculative Synthesis," Journal of Cerebral Blood Flow and Metabolism 1(2):155-185.
Silbert, L. et al. (1996). "The "S" in MELAS," Journal of Stroke and Cerebrovascular Diseases 6(2):67-71.
Strohschein, S. et al., (Jan. 1, 1998). "Shape Selectivity of C30 Phases for RP-HPLC Separation of Tocopherol Isomers and Correlation with MAS NMR Data from Suspended Stationary Phases," Analytical Chemistry 70(1):13-18.
Testa!, F.D. et al. (2010). "Inherited Metabolic Disorders and Stroke Part 1," Arch. Neurol. 67(1):19-24.
Theriault, A. et al. (Jul. 1999). "Tocotrienol: A Review of Its Therapeutic Potential," Clinical Biochemistry 32(5):309-319.
Thom S.M. et al. (1993). "Factors affecting the selection and use of tetrazolium salts as cytochemical indicators of microbial viability and activity," J. Appl. Bacteriol 74(4):433-43.
Tietjen, G.E. (1996). "Stroke in MELAS," Journal of Stroke and Cerebrovascular Diseases 6(2):59-60.
Tsuchiya, K. et al. (1999). "MELAS with Prominent White Matter Gliosis and Atrophy of the Cerebellar Granular Layer: A Clinical, Genetic, and Pathological Study," Acta Neuropathol. 97:520-524.
Watson, B.D. et al. (1989). "Ischemic Injury in the Brain. Role of Oxygen Radical-Mediated Processes," Annals. New York Academy of Sciences 559:269-281.
Wechter, W.J. et al. (Jun. 1996). "A New Endogenous Natriuretic Factor: LLU-α," Proc. Natl. Acad. Sci. USA 93:6002-6007.
International Preliminary Report on Patentability dated Feb. 28, 2012, for PCT Patent Application No. PCT/US2010/046503, filed on Aug. 24, 2010, one page.
International Search Report dated Nov. 9, 2010, for PCT Patent Application No. PCT/US2010/046503, filed on Aug. 24, 2010, four pages.
Written Opinion dated Nov. 9, 2010, for PCT Patent Application No. PCT/US2010/046503, filed on Aug. 24, 2010, four pages.
Jaiswal, A.K. (2000). "Characterization and Partial Purification of Microsomal NAD(P)H:Quinone Oxidoreductases," Archives of Biochemistry and Biophysics 375(1):62-68.
Yim, S. et al. (2005), "A Continuous Spectrophotometric Assay for NADPH-cytochrome P450 Reductase Activity Using 3-(4,5-Dimethylthiazol-2-yl)-2,5-diphenyltetrazolium Bromide," Journal of Biochemistry and Molecular Biology 38(3):366-369.
1957:81330 Caplus, We"Studies in the vitamin K and E series, III, Analogs of a-tocopherol with unbranched sidechains", 1 page.
202843-61-6 Registry, Mar. 19, 1998, 2,5-Cydohexadiene-1,4-dione, 2,3,5-trimethyl-6-[(2E)-3-methyl-2-nonen-1-yl], 1 page.
925-41-5 Registry, Nov. 16, 1984, 1,4-Benzenediol, 2,3,5-trimethyl-6-(3-methyl-2-nonadeceri-1-yl), 1 page.
Anderson et al. "No evidence for altered muscle mitochondrial function Anderson in Parkinson's disease", Journal of Neurology, Neurosurgery, and Psychiatry, 1993, vol. 56, pp. 477-480.
Anonymous, "Leigh Syndrome", NORD, located at http://rarediseases.org/rare-diseases/leigh-syndrome, the site was last visited on May 12, 2016, 14 pages.
Anonymous, ICD-10 Version:2015, "Other specified degenerative diseases of nervous system" located at http://apps.who.int/classifications/icd10/browse/2015/en#/G31.8, the site was last visited on May 12, 2016, 1 page.
Anonymous, Leigh syndrome—Genetics Home Reference, "Other Names for This Condition" located at https://ghr.nlm.nih.gov/condition/leigh-syndrome, the site was last visited on May 12, 2016, 8 pages.
Finsterer, "Leigh and Leigh-Like Syndrome in Children and Adults", Pediatric Neurology, 2008, vol. 39, No. 4, pp. 223-235.
Kabbe et al., (1978), "Eine Neue Synthese von 3,4-Dehydro-α-Tocotrienol und Vitamin-E", Synthesis 888-889 (Translation of Abstract only: Chemical Abstract Caplus Abstract No. 1979: 168774, 5 pages).
Non-Final Office Action dated Feb. 7, 2014, for U.S. Appl. No. 13/643,542, filed Nov. 26, 2012, 9 pages.
Sakamoto et al. "Role of the Isoprenyl Tail of Ubiquinone in Reaction with Respiratory Enzymes: Studies with Bovine Heart Mitochondrial Complex I and Escherichia coli bo-Type Ubiquinol Oxidase", Biochemistry, 1998, vol. 37, pp. 15106-15113.
Sue et al. "Mitochondria! Respiratory Chain Diseases and Mutations in Nuclear DNA: A Promising Start?", Brain Pathology, 2000, vol. 10, pp. 442-450.
Bertalan L. et al. (2000). "Recovery of fatty oil from the Transylvanian black current by means of supercritical and conventional extractions", Olaj, Szappn, Kozmetika, vol. 49, pp. 40-45, with English translation.
Blankenberg et al., "Brain uptake of Tc99m-HMPAO correlates with clinical response to the novel redox modulating agent EPI-743 in patients with mitochondrial disease," Molecular Genetics and Metabolism, 2012, vol. 107, pp. 690-699.
Blankenberg et al., "Clinical and radiological evidence for EPI-743 neuroprotection in mitochondrial disease," Annals of Neurology, 2011, vol. 70 (Supl 15), p. S148, abstract DD-54.
Delettre et al. "OPA1 (Kjer Type) Dominant Optic Atrophy: A Novel Mitochondrial Disease," Molecular Genetics and Metabolism, vol. 75, pp. 97-107 (2001).
Enns et al., "Initial experience in the treatment of inherited mitochondrial disease with EPI-743," Molecular Genetics and Metabolism, 2012, vol. 105, pp. 91-102.
Gonzalez (1990), "Serum Concentrations and Cellular Uptake of Vitamin E," Medical Hypotheses 32:107-110.
Kleijnen et al. "Niacin and vitamin B6 in mental functioning: A review of controlled trials in humans" Biol. Psychiatry, 1991, vol. 29, pp. 931-941.
Liepkalns et al. "Regulation of Cell Division in a Human Glioma Cell Clone by Arachidonic Acid and a-Tocopherolquinone," Cancer Letters, 15 (1982) 173-178.
Martinelli et al., "EPI-743 reduces seizure frequency in RARS2 defect syndrome," J Inherit Metab Dis, 2013, vol. 36 (Suppl 2):S91-S342; p. S110, abstract O-029.
Martinelli et al., "EPI-743 reverses the progression of the pediatric mitochondrial disease—Genetically defined Leigh Syndrome," Molecular Genetics and Metabolism, 2012, vol. 107, pp. 383-388.
Maso et al. "Leigh's Syndrome in an Adult," Journal of Neurology, 1984, vol. 231, pp. 253-257.
Mukai et al, "Stopped-flow kinetic study of vitamin E regeneration reaction with biological hydroquinones (reduced forms of ubiquinone, vitamin K, and tocopherolquinone) in solution", J Biol Chem, Nov. 5, 1992, vol. 267, No. 31, pp. 22277-22281.
Pearce et al. (1994), "Inhibitors of Cholesterol Biosynthesis. 2. Hypocholesterolemic and Antioxidant Activities of Benzopyran and Tetrahydronaphthalene Analogues of the Tocotrienols," Journal of Medicinal Chemistry 37(4):526-541.
Sadun et al., "Effect of EPI-743 on the Clinical Course of the Mitochondrial Disease Leber Hereditary Optic Neuropathy," Archives of Neurology, Mar. 2012, vol. 69, No. 3, pp. 331-338.
Silbert et al. (1996), "The "S" in MELAS," Journal of Stroke and Cerebrovascular Diseases 6(2):67-71.

(56) References Cited

OTHER PUBLICATIONS

Tiranti et al. "Mutations of SURF-1 in Leigh Disease Associated with Cytochrome c Oxidase Deficiency," *Am J. Hum. Genet.*, 1998, vol. 63, pp. 1609-1621.

Anonymous Ischemic Strokes (Clots), 2 pages, downloaded from: http://www.strokeassociation.org/STROKEORG/AboutStroke/TypesofStroke/IschemicClot . . . Apr. 4, 2018.

Fernando Scaglia, "MELAS Syndrome", NORD (National Organization for Rare Disorders), 14 pages, downloaded from https://rarediseases.org/rare-diseases/melas-syndrome . . . Apr. 4, 2018.

Kolb SJ et al., "Distinguishing ischemic stroke from the stroke-like lesions of MELAS using apparent diffusion coefficient mapping", J Neurol Sci., Dec. 15, 2003, vol. 216, No. 1, pp. 11-5; abstract only—1 page.

Ooiwa et al., "Cerebral Blood Flow in Mitochondrial Myopathy, Encephalopathy, Lactic Acidosis, and Strokelike Episodes", Stroke, vol. 24, No. 2, Feb. 1993, pp. 304-309; doi: 10.1161/01.STR.24.2.304.

Oppenheim et al., "Can diffusion weighted magnetic resonance imaging help differentiate stroke from stroke-like events in MELAS?", J Neurol Neurosurg Psychiatry, 2000, vol. 69, pp. 248-250; doi: 10.1136/jnnp.69.2.248.

Kasper et al., "Harrison's Principles of Internal Medicine", Sixteenth Edition, 2005, ISBN 007-1391404 (set)—ISBN 0-07-139141-X (v. 1)—ISBN 0-07-139142-8 (v. 2)—ISBN 0-07-140235-7 (combo); 6 pages.

Patel, "Mitochondrial Dysfunction and Oxidative Stress: Cause and Consequence of Epileptic Seizures", Free Radical Biology & Medicine, doi:10.1016/j.freeradbiomed.2004.08.021, 2004, pp. 1951-1962.

Napolitano et al., "Long-term treatment with idebenone and riboflavin in a patient with MELAS", Neurol Sci (2000) 21:S981-S982.

Rasool, N. et al., "A Benzoquinone and a Coumestan From Psoralea Plicata", Phytochemistry, 1991, vol. 30, No. 8, pp. 2800-2803.

Rötig et al., "Molecular insights into Friedreich's ataxia and antioxidant-based therapies", Trends in Molecular Medicine, vol. 8, No. 5, May 2002, pp. 221-224.

Taylor et al., "Mitochondrial DNA Mutations in Human Disease", Nature Reviews/Genetics, vol. 6, May 2005, pp. 389-402.

Van Haaften, R. I. M. et al., "Inhibition of human glutathione S-transferase P1-1 by tocopherols and α-tocopherol derivatives", Biochimica et Biophysica Acta, 2001, vol. 1548, pp. 23-28.

\* cited by examiner

REDOX-ACTIVE THERAPEUTICS FOR TREATMENT OF MITOCHONDRIAL DISEASES AND OTHER CONDITIONS AND MODULATION OF ENERGY BIOMARKERS

CROSS REFERENCE TO RELATED APPLICATIONS

This application is a divisional patent application of U.S. patent application Ser. No. 11/445,582, filed Jun. 1, 2006, which claims the priority benefit of U.S. Provisional Application No. 60/686,826, filed on Jun. 1, 2005, U.S. Provisional Application No. 60/701,815, filed Jul. 21, 2005, and U.S. Provisional Application No. 60/776,028, filed Feb. 22, 2006. The entire contents of those applications are hereby incorporated by reference herein.

TECHNICAL FIELD

The application discloses compositions and methods useful for treatment or suppression of diseases due to mitochondrial disorders, such as Friedreich's ataxia, Leber's Hereditary Optic Neuropathy, Kearns-Sayre Syndrome, and mitochondrial myopathy, encephalopathy, lactacidosis, stroke, and for modulating energy biomarkers in a subject.

BACKGROUND

Mitochondria are organelles in eukaryotic cells, popularly referred to as the "powerhouse" of the cell. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Kreb's cycle), which generates reduced nicotinamide adenine dinucleotide ($NADH+H^+$) from oxidized nicotinamide adenine dinucleotide ($NAD^+$), and oxidative phosphorylation, during which $NADH+H^+$ is oxidized back to $NAD^+$. (The citric acid cycle also reduces flavin adenine dinucleotide, or FAD, to $FADH_2$; $FADH_2$ also participates in oxidative phosphorylation.)

The electrons released by oxidation of $NADH+H^+$ are shuttled down a series of protein complexes (Complex I, Complex II, Complex III, and Complex IV) known as the respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

The citric acid cycle and oxidative phosphorylation are preceded by glycolysis, in which a molecule of glucose is broken down into two molecules of pyruvate, with net generation of two molecules of ATP per molecule of glucose. The pyruvate molecules then enter the mitochondria, where they are completely oxidized to $CO_2$ and $H_2O$ via oxidative phosphorylation (the overall process is known as aerobic respiration). The complete oxidation of the two pyruvate molecules to carbon dioxide and water yields about at least 28-29 molecules of ATP, in addition to the 2 molecules of ATP generated by transforming glucose into two pyruvate molecules. If oxygen is not available, the pyruvate molecule does not enter the mitochondria, but rather is converted to lactate, in the process of anaerobic respiration.

The overall net yield per molecule of glucose is thus approximately at least 30-31 ATP molecules. ATP is used to power, directly or indirectly, almost every other biochemical reaction in the cell. Thus, the extra (approximately) at least 28 or 29 molecules of ATP contributed by oxidative phosphorylation during aerobic respiration are critical to the proper functioning of the cell. Lack of oxygen prevents aerobic respiration and will result in eventual death of almost all aerobic organisms; a few organisms, such as yeast, are able to survive using either aerobic or anaerobic respiration.

When cells in an organism are temporarily deprived of oxygen, anaerobic respiration is utilized until oxygen again becomes available or the cell dies. The pyruvate generated during glycolysis is converted to lactate during anaerobic respiration. The buildup of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Genetic defects in the proteins making up the respiratory chain lead to severe disease states. One such disease is Friedreich's ataxia (FRDA or FA). Friedreich's ataxia is an autosomal recessive neurodegenerative and cardiodegenerative disorder caused by decreased levels of the protein frataxin. Frataxin is important for the assembly of iron-sulfur clusters in mitochondrial respiratory-chain complexes. Estimates of the prevalence of FRDA in the United States range from 1 in every 22,000-29,000 people (see World-Wide-Web address.nlm.nih.gov/medlineplus/ency/article/001411.htm) to 1 in 50,000 people (World-Wide-Web address.umc-cares.org/health_info/ADAM/Articles/0014-11.asp). The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

Another disease linked to mitochondrial dysfunction is Leber's Hereditary Optic Neuropathy (LHON). The disease is characterized by blindness which occurs on average between 27 and 34 years of age (World-Wide-Web address .ncbi.nlm.nih.gov/entrez/dispomim.cgi?id=535000); blindness can develop in both eyes simultaneously, or sequentially (one eye will develop blindness, followed by the other eye two months later on average). Other symptoms may also occur, such as cardiac abnormalities and neurological complications.

Yet another devastating syndrome resulting from mitochondrial defects is mitochondrial myopathy, encephalopathy, lactacidosis, and stroke (MELAS). The disease can manifest itself in infants, children, or young adults. Strokes, accompanied by vomiting and seizures, are one of the most serious symptoms; it is postulated that the metabolic impairment of mitochondria in certain areas of the brain is responsible for cell death and neurological lesions, rather than the impairment of blood flow as occurs in ischemic stroke. Other severe complications, including neurological symptoms, are often present, and elevated levels of lactic acid in the blood occur.

Another mitochondrial disease is Kearns-Sayre Syndrome (KSS). KSS is characterized by a triad of features including: (1) typical onset in persons younger than age 20 years; (2) chronic, progressive, external opthalmoplegia; and (3) pigmentary degeneration of the retina. In addition, KSS may include cardiac conduction defects, cerebellar ataxia, and raised cerebrospinal fluid (CSF) protein levels (e.g., >100 mg/dL). Additional features associated with KSS may include myopathy, dystonia, endocrine abnormalities (e.g., diabetes, growth retardation or short stature, and hypoparathyroidism), bilateral sensorineural deafness, dementia, cataracts, and proximal renal tubular acidosis. Thus, KSS may affect many organ systems.

The four diseases above appear to be caused by defects in complex I of the respiratory chain. Electron transfer from complex I to the remainder of the respiratory chain is mediated by the compound coenzyme Q (also known as ubiquinone). Oxidized coenzyme Q ($CoQ^{ox}$ or ubiquinone) is reduced by complex I to reduced coenzyme Q ($CoQ^{red}$ or ubiquinol). The reduced coenzyme Q then transfers its electrons to complex III of the respiratory chain (skipping over complex II), where it is re-oxidized to $CoQ^{ox}$ (ubiquinone). $CoQ^{ox}$ can then participate in further iterations of electron transfer.

Very few treatments are available for patients suffering from these diseases. Recently, the compound idebenone has been proposed for treatment of Friedreich's ataxia. While the clinical effects of idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Patent Application Publication No. 2005/0043553); clinical results for MitoQ have not yet been reported. For KSS, administration of coenzyme Q10 (CoQ10) and vitamin supplements have shown only transient beneficial effects in individual cases.

Accordingly, there is a serious and unmet need for effective treatments of mitochondrial disorders, such as Friedreich's ataxia, Leber's hereditary optic neuropathy, MELAS, and Kearns-Sayre Syndrome.

The ability to adjust biological production of energy has applications beyond the diseases described above. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. For example, if an individual is undergoing an extremely strenuous undertaking, it can be desirable to raise the level of ATP in that individual.

DISCLOSURE OF THE INVENTION

In one embodiment, the invention embraces compounds of formula

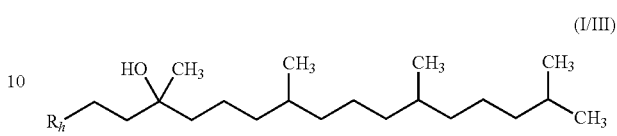

(I/III)

where $R_h$ is selected from the group consisting of:

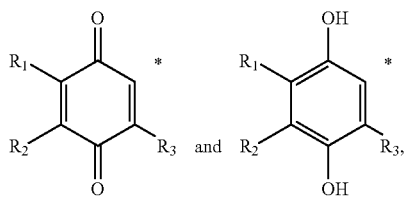

where the * indicates the point of attachment of $R_h$ to the remainder of the molecule;

where $R_1$, $R_2$, and $R_3$ are independently selected from —$C_1$-$C_4$ alkyl, —$C_1$-$C_4$ haloalkyl, —CN, —F, —Cl, —Br, and —I, with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula VIII as described above.

In another embodiment, the invention embraces compounds of formula I:

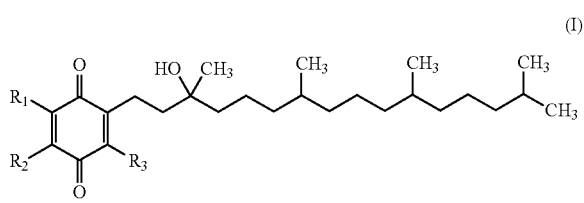

(I)

where $R_1$, $R_2$, and $R_3$ are independently selected from —$C_1$-$C_4$ alkyl, —$C_1$-$C_4$ haloalkyl, —CN, —F, —Cl, —Br, and —I, with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula Ia:

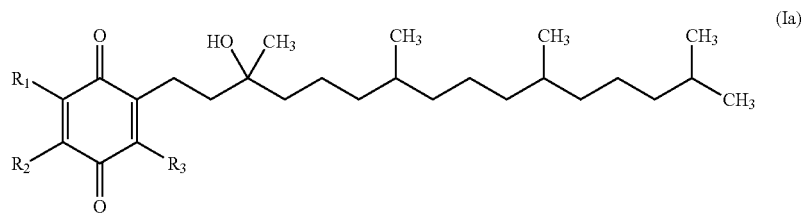

(Ia)

where $R_1$, $R_2$, and $R_3$ are independently selected from —$C_1$-$C_4$ alkyl, with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula Ia, where $R_1$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment; where $R_2$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment; and where $R_3$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment; with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula Ia where $R_1$, $R_2$, and $R_3$ are independently selected from methyl, ethyl, n-propyl, and n-butyl, with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula Ia where $R_1$, $R_2$, and $R_3$ are independently selected from $C_2$-$C_4$ alkyl; and all salts, stereoisomers, mixtures of stereoisomers, prodrugs, metabolites, solvates, and hydrates thereof.

In another embodiment, the invention embraces compounds of formula Ia where $R_1$, $R_2$, and $R_3$ are independently selected from $C_2$-$C_4$ n-alkyl; and all salts, stereoisomers, mixtures of stereoisomers, prodrugs, metabolites, solvates, and hydrates thereof.

In another embodiment, the invention embraces compounds of formula Ia, where $R_1$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment; where $R_2$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment; and where $R_3$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment; and all salts, stereoisomers, mixtures of stereoisomers, prodrugs, metabolites, solvates, and hydrates thereof.

In another embodiment, the invention embraces compounds of formula Ia wherein any one of $R_1$, $R_2$, and $R_3$ is methyl and the remaining groups are independently selected from $C_2$-$C_4$ alkyl; and all salts, stereoisomers, mixtures of stereoisomers, prodrugs, metabolites, solvates, and hydrates thereof. The $C_2$-$C_4$ alkyl groups are independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of the $C_2$-$C_4$ alkyl group to the remainder of the molecule can be at any location on the alkyl fragments.

In another embodiment, the invention embraces compounds of formula Ia wherein any two of $R_1$, $R_2$, and $R_3$ are methyl and the remaining group is independently selected from $C_2$-$C_4$ alkyl; and all salts, stereoisomers, mixtures of stereoisomers, prodrugs, metabolites, solvates, and hydrates thereof. The $C_2$-$C_4$ alkyl group is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of the $C_2$-$C_4$ alkyl group to the remainder of the molecule can be at any location on the alkyl fragment.

In another embodiment, the invention embraces compounds of the formula Ib:

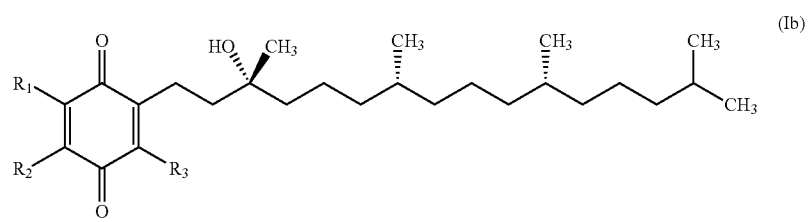

(Ib)

where $R_1$, $R_2$, and $R_3$ are as defined above for formula I, formula Ia, and all embodiments of formula Ia.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula I, formula Ia, or formula Ib, or of the embodiments of formula I, formula Ia, or formula Ib, as described above.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula II:

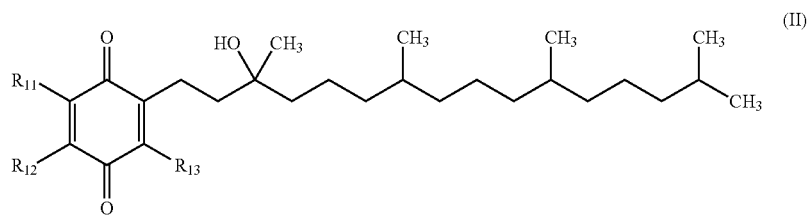

where $R_{11}$, $R_{12}$, and $R_{13}$ are independently selected from H, —$C_1$-$C_4$ alkyl, —$C_1$-$C_4$ haloalkyl, —CN, —F, —Cl, —Br, and —I, with the proviso that if any of $R_{11}$, $R_{12}$, or $R_{13}$ is H, then at least one of the other two substituents is neither H nor methyl; and all salts, stereoisomers, mixtures of stereoisomers, prodrugs, metabolites, solvates, and hydrates thereof. In one embodiment, $R_{11}$, $R_{12}$, and $R_{13}$ are all methyl. In another embodiment, at least one of $R_{11}$, $R_{12}$, and $R_{13}$ is not methyl.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of alpha-tocopherol quinone.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula IIa:

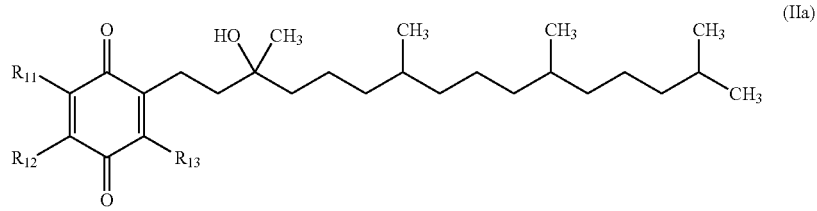

where $R_{11}$ is independently selected from H, methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_{11}$ to the remainder of the molecule can be at any location on the alkyl fragment; where $R_{12}$ is independently selected from H, methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_{12}$ to the remainder of the molecule can be at any location on the alkyl fragment; and where $R_{13}$ is independently selected from H, methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_{13}$ to the remainder of the molecule can be at any location on the alkyl fragment; with the proviso that if any of $R_{11}$, $R_{12}$, or $R_{13}$ is H, then at least one of the other two substituents is neither H nor methyl; and all salts, stereoisomers, mixtures of stereoisomers, prodrugs, metabolites, solvates, and hydrates thereof. In one embodiment, $R_{11}$, $R_{12}$, and $R_{13}$ are all methyl. In another embodiment, at least one of $R_{11}$, $R_{12}$, and $R_{13}$ is not methyl.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula IIa where $R_{11}$, $R_{12}$, and $R_{13}$ are independently selected from H, methyl, ethyl, n-propyl, and n-butyl; with the proviso that if any of $R_{11}$, $R_{12}$, or $R_{13}$ is H, then at least one of the other two substituents is neither H nor methyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula IIa where $R_{11}$, $R_{12}$, and $R_{13}$ are independently selected from —$C_1$-$C_4$ alkyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula IIa where $R_{11}$, $R_{12}$, and $R_{13}$ are independently selected from —$C_1$-$C_4$ n-alkyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula IIb:

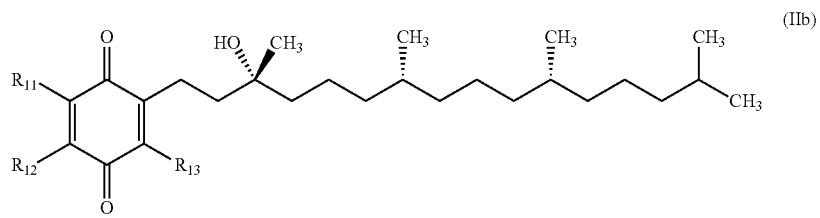

(IIb)

where $R_{11}$, $R_{12}$, and $R_{13}$ are as described above for formula II or formula IIa. In one embodiment, $R_{11}$, $R_{12}$, and $R_{13}$ are all methyl. In another embodiment, at least one of $R_{11}$, $R_{12}$, and $R_{13}$ is not methyl.

In another embodiment, the invention embraces compounds of formula III:

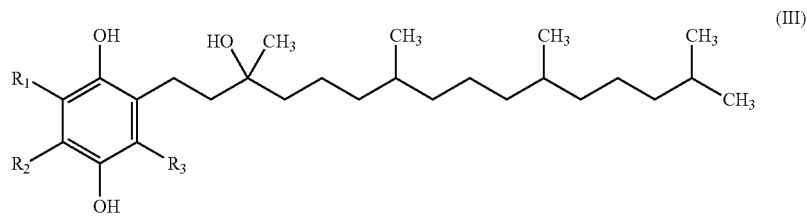

(III)

where $R_1$, $R_2$, and $R_3$ are independently selected from —$C_1$-$C_4$ alkyl, —$C_1$-$C_4$ haloalkyl, —CN, —F, —Cl, —Br, and —I, with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula IIIa:

where $R_1$, $R_2$, and $R_3$ are independently selected from —$C_1$-$C_4$ alkyl, with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula IIIa, where $R_1$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment; where $R_2$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment; and where $R_3$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment; with the proviso that at least one of $R_1$, $R_2$, and $R_3$ is not methyl;

and all salts, stereoisomers, mixtures of stereoisomers, prodrugs, metabolites, solvates, and hydrates thereof.

In another embodiment, the invention embraces compounds of formula IIIa where $R_1$, $R_2$, and $R_3$ are independently selected from methyl, ethyl, n-propyl, and n-butyl, with the proviso that at least one of $R_1$, $R_2$, and $R_3$ is not methyl; and all salts, stereoisomers, mixtures of stereoisomers, prodrugs, metabolites, solvates, and hydrates thereof.

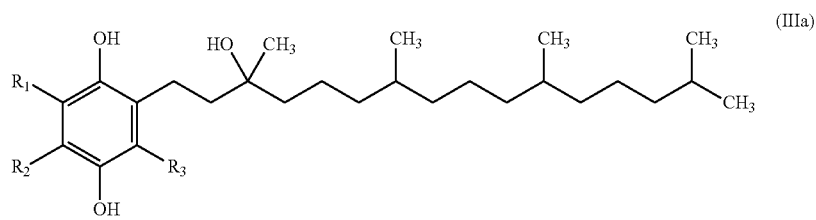

(IIIa)

In another embodiment, the invention embraces compounds of formula IIIa where $R_1$, $R_2$, and $R_3$ are independently selected from $C_2$-$C_4$ alkyl; and all salts, stereoisomers, mixtures of stereoisomers, prodrugs, metabolites, solvates, and hydrates thereof.

In another embodiment, the invention embraces compounds of formula IIIa where $R_1$, $R_2$, and $R_3$ are independently selected from $C_2$-$C_4$ n-alkyl; and all salts, stereoisomers, mixtures of stereoisomers, prodrugs, metabolites, solvates, and hydrates thereof.

In another embodiment, the invention embraces compounds of formula IIIa, where $R_1$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment; where $R_2$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment; and where $R_3$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment; and all salts, stereoisomers, mixtures of stereoisomers, prodrugs, metabolites, solvates, and hydrates thereof.

In another embodiment, the invention embraces compounds of formula IIIa wherein any one of $R_1$, $R_2$, and $R_3$ is methyl and the remaining groups are independently selected from $C_2$-$C_4$ alkyl; and all salts, stereoisomers, mixtures of stereoisomers, prodrugs, metabolites, solvates, and hydrates thereof. The $C_2$-$C_4$ alkyl groups are independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of the $C_2$-$C_4$ alkyl group to the remainder of the molecule can be at any location on the alkyl fragments.

In another embodiment, the invention embraces compounds of formula IIIa wherein any two of $R_1$, $R_2$, and $R_3$ are methyl and the remaining group is independently selected from $C_2$-$C_4$ alkyl; and all salts, stereoisomers, mixtures of stereoisomers, prodrugs, metabolites, solvates, and hydrates thereof. The $C_2$-$C_4$ alkyl group is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of the $C_2$-$C_4$ alkyl group to the remainder of the molecule can be at any location on the alkyl fragment.

In another embodiment, the invention embraces compounds of the formula IIIb:

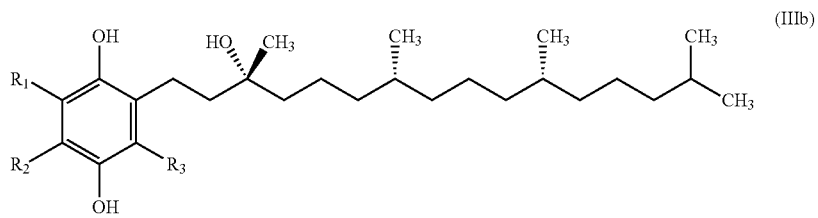

where $R_1$, $R_2$, and $R_3$ are as defined above for formula III, formula IIIa, and all embodiments of formula IIIa.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula III, formula IIIa, or formula IIIb, or of the embodiments of formula III, formula IIIa, or formula IIIb, as described above.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula IV:

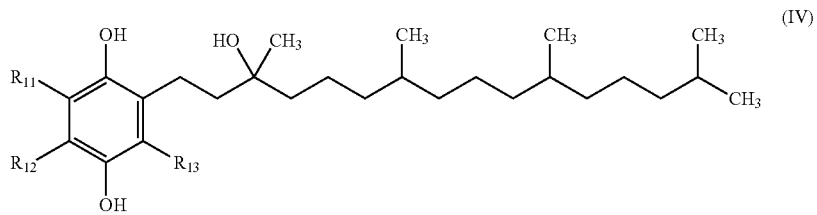

where $R_{11}$, $R_{12}$, and $R_{13}$ are independently selected from H, —$C_1$-$C_4$ alkyl, —$C_1$-$C_4$ haloalkyl, —CN, —F, —Cl, —Br, and —I, with the proviso that if any of $R_{11}$, $R_{12}$, or $R_{13}$ is H, then at least one of the other two substituents is neither H nor methyl; and all salts, stereoisomers, mixtures of stereoisomers, prodrugs, metabolites, solvates, and hydrates thereof. In one embodiment, $R_{11}$, $R_{12}$, and $R_{13}$ are all methyl. In another embodiment, at least one of $R_{11}$, $R_{12}$, and $R_{13}$ is not methyl.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula IVa:

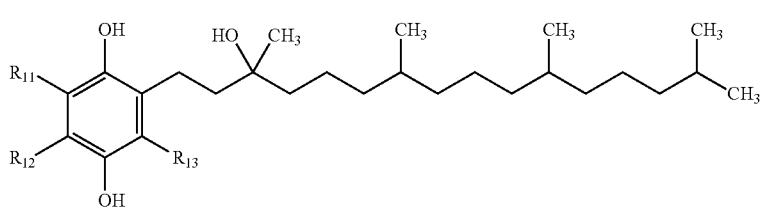

(IVa)

where $R_{11}$ is independently selected from H, methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_{11}$ to the remainder of the molecule can be at any location on the alkyl fragment; where $R_{12}$ is independently selected from H, methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_{12}$ to the remainder of the molecule can be at any location on the alkyl fragment; and where $R_{13}$ is independently selected from H, methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_{13}$ to the remainder of the molecule can be at any location on the alkyl fragment; with the proviso that if any of $R_{11}$, $R_{12}$, or $R_{13}$ is H, then at least one of the other two substituents is neither H nor methyl; and all salts, stereoisomers, mixtures of stereoisomers, prodrugs, metabolites, solvates, and hydrates thereof. In one embodiment, $R_{11}$, $R_{12}$, and $R_{13}$ are all methyl. In another embodiment, at least one of $R_{11}$, $R_{12}$, and $R_{13}$ is not methyl.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula IVa where $R_{11}$, $R_{12}$, and $R_{13}$ are independently selected from H, methyl, ethyl, n-propyl, and n-butyl; with the proviso that if any of $R_{11}$, $R_{12}$, or $R_{13}$ is H, then at least one of the other two substituents is neither H nor methyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula IVa where $R_{11}$, $R_{12}$, and $R_{13}$ are independently selected from —$C_1$-$C_4$ alkyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula IVa where $R_{11}$, $R_{12}$, and $R_{13}$ are independently selected from —$C_1$-$C_4$ n-alkyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula IVb:

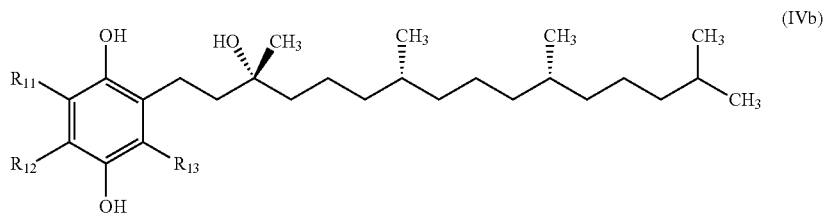

(IVb)

where $R_{11}$, $R_{12}$, and $R_{13}$ are as described above for formula IV or formula IVa. In one embodiment, $R_{11}$, $R_{12}$, and $R_{13}$ are all methyl. In another embodiment, at least one of $R_{11}$, $R_{12}$, and $R_{13}$ is not methyl.

In another embodiment, the invention embraces compounds of the formula V:

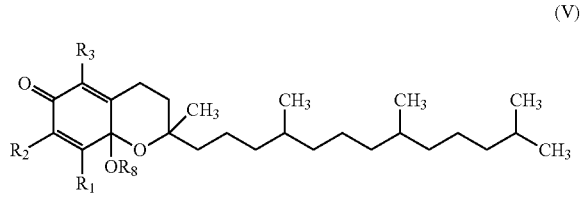

(V)

where $R_1$, $R_2$, and $R_3$ are independently selected from —$C_1$-$C_4$ alkyl, —$C_1$-$C_4$ haloalkyl, —CN, —F, —Cl, —Br, and —I, with the proviso that at least one of $R_1$, $R_2$, and $R_3$ is not methyl; $R_8$ is independently selected from H and —$C_1$-$C_6$ alkyl optionally substituted with —$OR_9$ or —N($R_9$)$_2$, where each $R_9$ is independently selected from H and —$C_1$-$C_6$ alkyl; and all salts, stereoisomers, mixtures of stereoisomers, prodrugs, metabolites, solvates, and hydrates thereof. In another embodiment, $R_8$ is independently selected from H and —$C_1$-$C_6$ alkyl optionally substituted with —$OR_9$.

In another embodiment, the invention embraces compounds of formula Va:

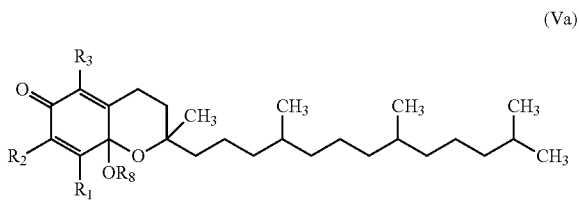

(Va)

where $R_1$, $R_2$, and $R_3$ are independently selected from —$C_1$-$C_4$ alkyl, with the proviso that at least one of $R_1$, $R_2$, and $R_3$ is not methyl; $R_8$ is independently selected from H and —$C_1$-$C_6$ alkyl optionally substituted with —$OR_9$ or —$N(R_9)_2$, where each $R_9$ is independently selected from H and —$C_1$-$C_6$ alkyl; and all salts, stereoisomers, mixtures of stereoisomers, prodrugs, metabolites, solvates, and hydrates thereof. In another embodiment, $R_8$ is independently selected from H and —$C_1$-$C_6$ alkyl optionally substituted with —$OR_9$.

In another embodiment, the invention embraces compounds of formula Va, where $R_1$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment; where $R_2$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment; and where $R_3$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment; with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula Va where $R_1$, $R_2$, and $R_3$ are independently selected from methyl, ethyl, n-propyl, and n-butyl, with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula Va where $R_1$, $R_2$, and $R_3$ are independently selected from methyl, ethyl, n-propyl, and n-butyl, with the proviso that when $R_1$, $R_2$, and $R_3$ are all methyl, then $R_8$ is $C_5$ alkyl or $C_6$ alkyl optionally substituted with —$OR_9$ or —$N(R_9)_2$; and all salts, stereoisomers, mixtures of stereoisomers, prodrugs, metabolites, solvates, and hydrates thereof. In another embodiment, $R_8$ is independently selected from $C_5$ alkyl or $C_6$ alkyl optionally substituted with —$OR_9$.

In another embodiment, the invention embraces compounds of formula Va where $R_1$, $R_2$, and $R_3$ are independently selected from $C_2$-$C_4$ alkyl; and all salts, stereoisomers, mixtures of stereoisomers, prodrugs, metabolites, solvates, and hydrates thereof.

In another embodiment, the invention embraces compounds of formula Va where $R_1$, $R_2$, and $R_3$ are independently selected from $C_2$-$C_4$ n-alkyl; and all salts, stereoisomers, mixtures of stereoisomers, prodrugs, metabolites, solvates, and hydrates thereof.

In another embodiment, the invention embraces compounds of formula Va, where $R_1$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment; where $R_2$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment; and where $R_3$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment; and all salts, stereoisomers, mixtures of stereoisomers, prodrugs, metabolites, solvates, and hydrates thereof.

In another embodiment, the invention embraces compounds of formula Va wherein any one of $R_1$, $R_2$, and $R_3$ is methyl and the remaining groups are independently selected from $C_2$-$C_4$ alkyl; and all salts, stereoisomers, mixtures of stereoisomers, prodrugs, metabolites, solvates, and hydrates thereof. The $C_2$-$C_4$ alkyl groups are independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of the $C_2$-$C_4$ alkyl group to the remainder of the molecule can be at any location on the alkyl fragments.

In another embodiment, the invention embraces compounds of formula Va wherein any two of $R_1$, $R_2$, and $R_3$ are methyl and the remaining group is independently selected from $C_2$-$C_4$ alkyl; and all salts, stereoisomers, mixtures of stereoisomers, prodrugs, metabolites, solvates, and hydrates thereof. The $C_2$-$C_4$ alkyl group is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of the $C_2$-$C_4$ alkyl group to the remainder of the molecule can be at any location on the alkyl fragment.

In another embodiment, the invention embraces compounds of the formula Vb:

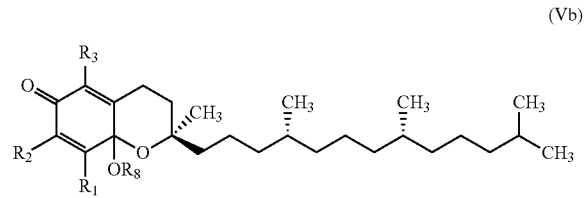

(Vb)

where $R_1$, $R_2$, $R_3$, and $R_8$ are as defined above for formula V, formula Va, and all embodiments of formula Va.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula V, formula Va, or formula Vb, or of any of the embodiments of formula V, formula Va, or formula Vb, as described above.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula VI:

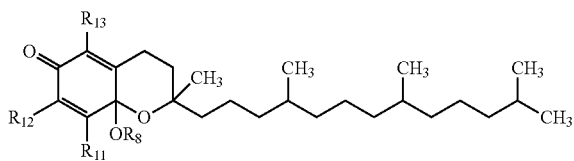

(VI)

where $R_{11}$, $R_{12}$, and $R_{13}$ are independently selected from H, —$C_1$-$C_4$ alkyl, —$C_1$-$C_4$ haloalkyl, —CN, —F, —Cl, —Br, and —I; $R_8$ is independently selected from H and —$C_1$-$C_6$ alkyl optionally substituted with —$OR_9$ or —$N(R_9)_2$, where each $R_9$ is independently selected from H and —$C_1$-$C_6$ alkyl; and all salts, stereoisomers, mixtures of stereoisomers, prodrugs, metabolites, solvates, and hydrates thereof. In one embodiment, $R_{11}$, $R_{12}$, and $R_{13}$ are all methyl. In another embodiment, at least one of $R_{11}$, $R_{12}$, and $R_{13}$ is not methyl. In another embodiment, $R_8$ is independently selected from H and —$C_1$-$C_6$ alkyl optionally substituted with —$OR_9$. In another embodiment, the proviso is added that if any of $R_{11}$, $R_{12}$, or $R_{13}$ is H, then at least one of the other two substituents is neither H nor methyl.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula VIa:

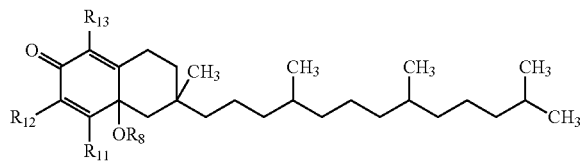

(VIa)

where $R_{11}$ is independently selected from H, methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_{11}$ to the remainder of the molecule can be at any location on the alkyl fragment; where $R_{12}$ is independently selected from H, methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_{12}$ to the remainder of the molecule can be at any location on the alkyl fragment; and where $R_{13}$ is independently selected from H, methyl, ethyl, n-propyl, isopropyl, cyclo-propyl, n-butyl, isobutyl, sec-butyl, t-butyl, cyclobutyl, cyclopropyl-methyl, and methyl-cyclopropane, where the point of attachment of $R_{13}$ to the remainder of the molecule can be at any location on the alkyl fragment; $R_8$ is independently selected from H and —$C_1$-$C_6$ alkyl optionally substituted with —$OR_9$ or —$N(R_9)_2$, where each $R_9$ is independently selected from H and —$C_1$-$C_6$ alkyl; and all salts, stereoisomers, mixtures of stereoisomers, prodrugs, metabolites, solvates, and hydrates thereof. In one embodiment, $R_{11}$, $R_{12}$, and $R_{13}$ are all methyl. In another embodiment, at least one of $R_{11}$, $R_{12}$, and $R_{13}$ is not methyl. In another embodiment, $R_8$ is independently selected from H and —$C_1$-$C_6$ alkyl optionally substituted with —$OR_9$. In another embodiment, the proviso is added that if any of $R_{11}$, $R_{12}$, or $R_{13}$ is H, then at least one of the other two substituents is neither H nor methyl.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula VIa where $R_{11}$, $R_{12}$, and $R_{13}$ are independently selected from H, methyl, ethyl, n-propyl, and n-butyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula VIa where $R_{11}$, $R_{12}$, and $R_{13}$ are independently selected from —$C_1$-$C_4$ alkyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula VIa where $R_{11}$, $R_{12}$, and $R_{13}$ are independently selected from —$C_1$-$C_4$ n-alkyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula VIb:

(VIb)

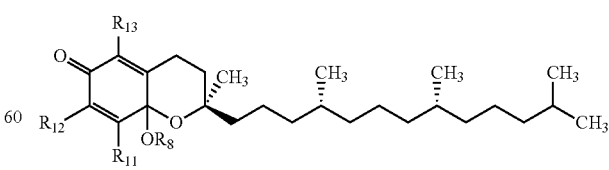

where $R_{11}$, $R_{12}$, and $R_{13}$ are as described above for formula VI or formula VIa. In one embodiment, $R_{11}$, $R_{12}$, and $R_{13}$ are all methyl. In another embodiment, at least one of $R_{11}$, $R_{12}$, and $R_{13}$ is not methyl.

In another embodiment, the invention embraces compounds of formula VII-O, formula VII-R, formula VIII-O, formula VIII-R, formula IX-O, or formula IX-R:

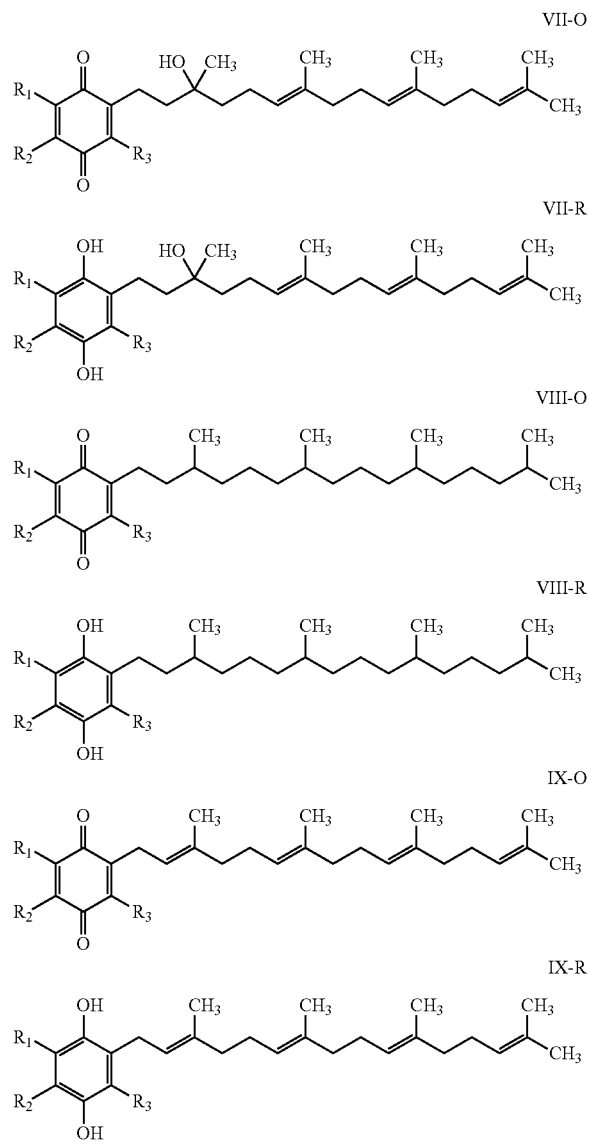

where $R_1$, $R_2$, and $R_3$ are independently selected from —$C_1$-$C_4$ alkyl, with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula VII-O, formula VII-R, formula VIII-O, formula VIII-R, formula IX-O, or formula IX-R, where $R_1$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment; where $R_2$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment; and where $R_3$ is independently selected from methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment; with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula VII-O, formula VII-R, formula VIII-O, formula VIII-R, formula IX-O, or formula IX-R where $R_1$, $R_2$, and $R_3$ are independently selected from methyl, ethyl, n-propyl, and n-butyl, with the proviso that at least one of $R_1$, $R_2$, and $R_3$ is not methyl; and all salts, stereoisomers, mixtures of stereoisomers, prodrugs, metabolites, solvates, and hydrates thereof.

In another embodiment, the invention embraces compounds of formula VII-O, formula VII-R, formula VIII-O, formula VIII-R, formula IX-O, or formula IX-R where $R_1$, $R_2$, and $R_3$ are independently selected from $C_2$-$C_4$ alkyl; and all salts, stereoisomers, mixtures of stereoisomers, prodrugs, metabolites, solvates, and hydrates thereof.

In another embodiment, the invention embraces compounds of formula VII-O, formula VII-R, formula VIII-O, formula VIII-R, formula IX-O, or formula IX-R where $R_1$, $R_2$, and $R_3$ are independently selected from $C_2$-$C_4$ n-alkyl; and all salts, stereoisomers, mixtures of stereoisomers, prodrugs, metabolites, solvates, and hydrates thereof.

In another embodiment, the invention embraces compounds of formula VII-O, formula VII-R, formula VIII-O, formula VIII-R, formula IX-O, or formula IX-R, where $R_1$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_1$ to the remainder of the molecule can be at any location on the alkyl fragment; where $R_2$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_2$ to the remainder of the molecule can be at any location on the alkyl fragment; and where $R_3$ is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_3$ to the remainder of the molecule can be at any location on the alkyl fragment; and all salts, stereoisomers, mixtures of stereoisomers, prodrugs, metabolites, solvates, and hydrates thereof.

In another embodiment, the invention embraces compounds of formula VII-O, formula VII-R, formula VIII-O, formula VIII-R, formula IX-O, or formula IX-R wherein any one of $R_1$, $R_2$, and $R_3$ is methyl and the remaining groups are independently selected from $C_2$-$C_4$ alkyl; and all salts, stereoisomers, mixtures of stereoisomers, prodrugs, metabolites, solvates, and hydrates thereof. The $C_2$-$C_4$ alkyl groups are independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of the $C_2$-$C_4$ alkyl group to the remainder of the molecule can be at any location on the alkyl fragments.

In another embodiment, the invention embraces compounds of formula VII-O, formula VII-R, formula VIII-O, formula VIII-R, formula IX-O, or formula IX-R wherein any two of $R_1$, $R_2$, and $R_3$ are methyl and the remaining group is independently selected from $C_2$-$C_4$ alkyl; and all salts, stereoisomers, mixtures of stereoisomers, prodrugs, metabolites, solvates, and hydrates thereof. The $C_2$-$C_4$ alkyl group is independently selected from ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of the $C_2$-$C_4$ alkyl group to the remainder of the molecule can be at any location on the alkyl fragment.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula X-O, formula X-R, formula XI-0, formula XI-R, formula XII-O, or formula XII-R:

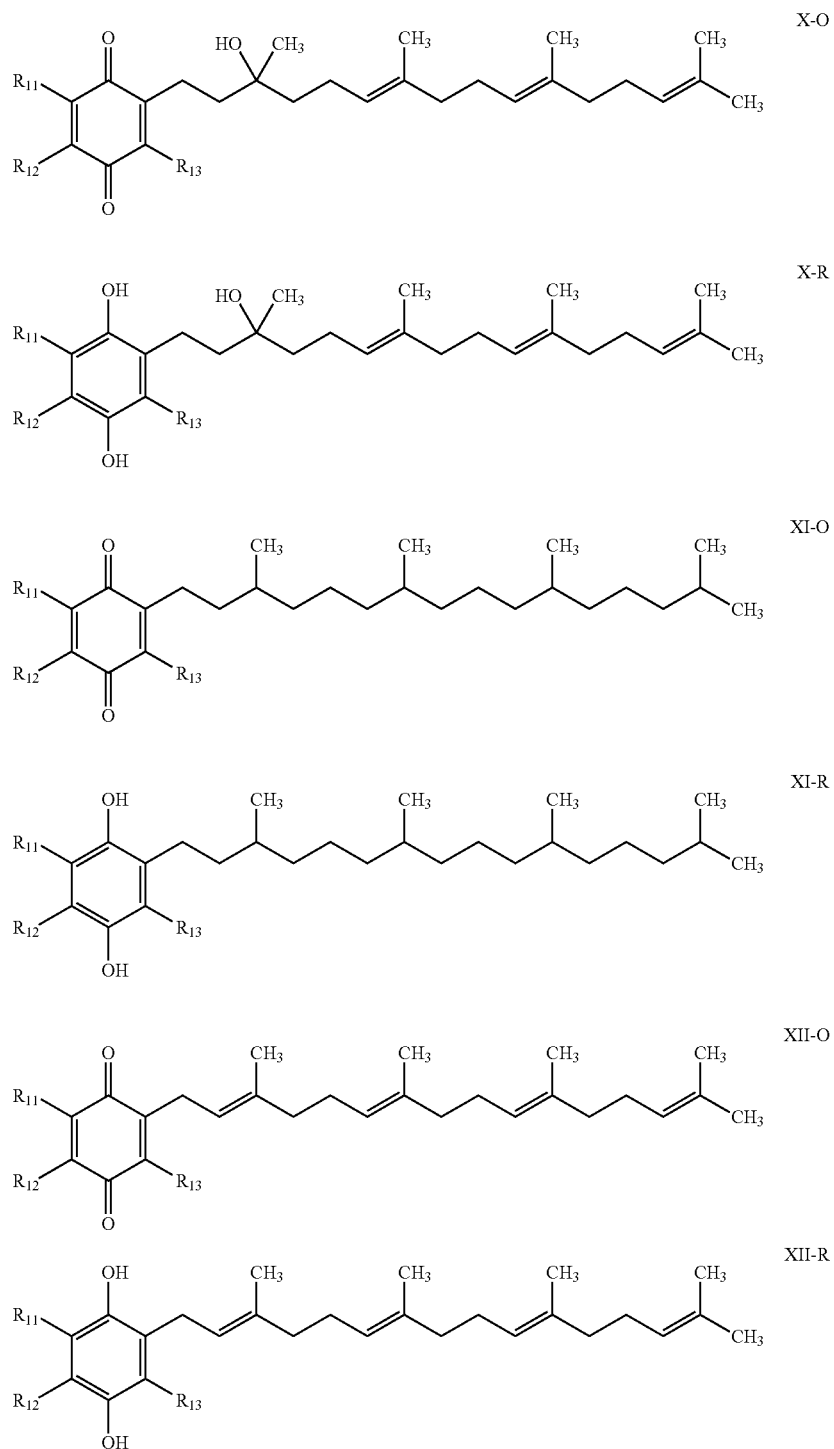

where $R_{11}$, $R_{12}$, and $R_{13}$ are independently selected from H, —$C_1$-$C_4$ alkyl, —$C_1$-$C_4$ haloalkyl, —CN, —F, —Cl, —Br, and —I, with the proviso that if any of $R_{11}$, $R_{12}$, or $R_{13}$ is H, then at least one of the other two substituents is neither H nor methyl; and all salts, stereoisomers, mixtures of stereoisomers, prodrugs, metabolites, solvates, and hydrates thereof. In one embodiment, $R_{11}$, $R_{12}$, and $R_{13}$ are all methyl. In another embodiment, at least one of $R_{11}$, $R_{12}$, and $R_{13}$ is not methyl.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula X-O, formula X-R, formula XI-O, formula XI-R, formula XII-O, or formula XII-R:

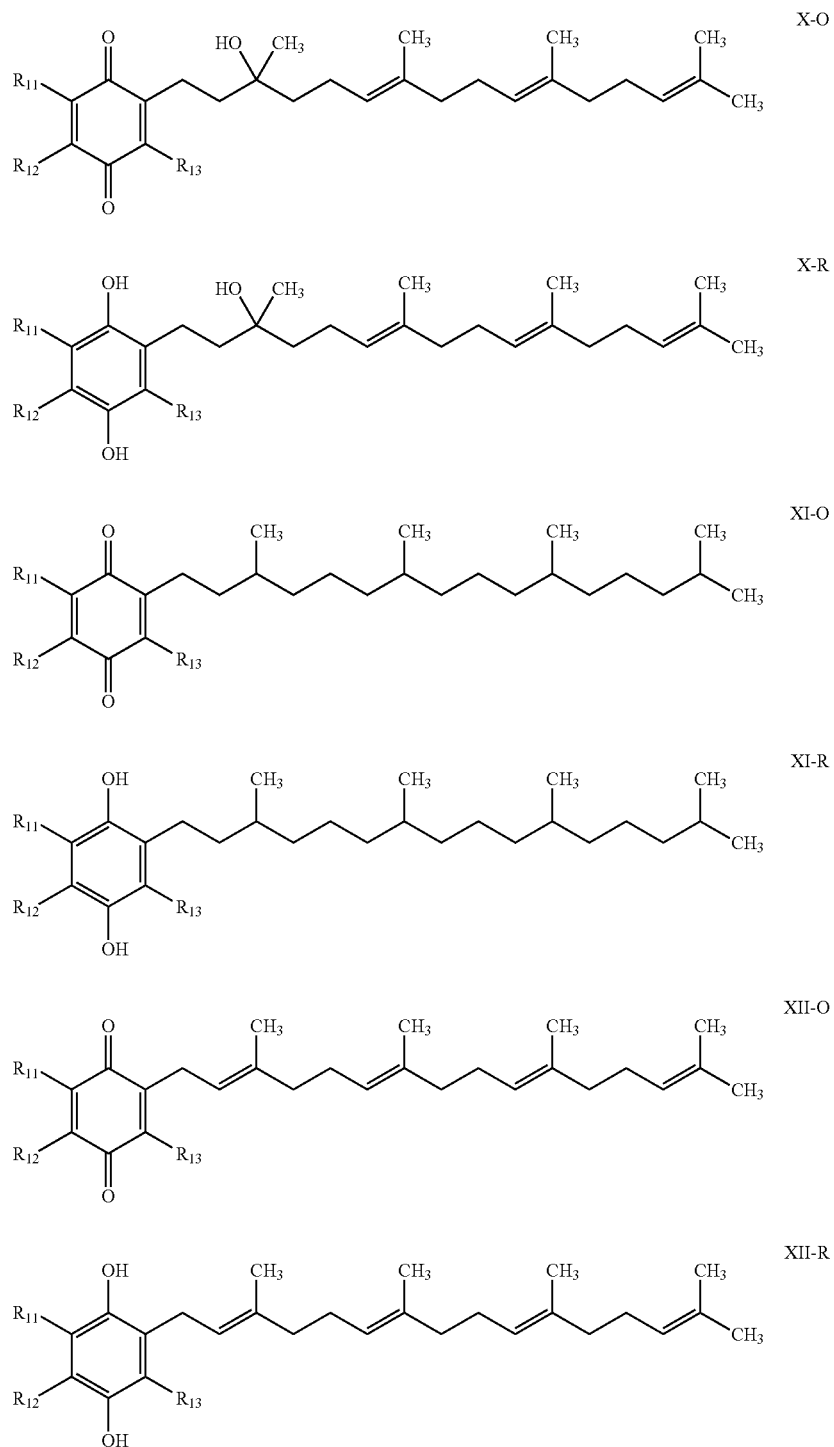

where $R_{11}$ is independently selected from H, methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_{11}$ to the remainder of the molecule can be at any location on the alkyl fragment; where $R_{12}$ is independently selected from H, methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_{12}$ to the remainder of the molecule can be at any location on the alkyl fragment; and where $R_{13}$ is independently selected from H, methyl, ethyl, n-propyl, isopropyl, cyclopropyl, n-butyl, isobutyl, sec-butyl, t-butyl, cyclobutyl, cyclopropyl-methyl, and methyl-cyclopropane, where the point of attachment of $R_{13}$ to the remainder of the molecule can be at any location on the alkyl fragment; with the proviso that if any of $R_{11}$, $R_{12}$, or $R_{13}$ is H, then at least one of the other two substituents is neither H nor methyl; and all salts, stereoisomers, mixtures of stereoisomers, prodrugs, metabolites, solvates, and hydrates thereof. In one embodiment, $R_{11}$, $R_{12}$, and $R_{13}$ are all methyl. In another embodiment, at least one of $R_{11}$, $R_{12}$, and $R_{13}$ is not methyl.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula X-O, formula X-R, formula XI-O, formula XI-R, formula XII-O, or formula XII-R where $R_{11}$, $R_{12}$, and $R_{13}$ are independently selected from methyl, ethyl, n-propyl, and n-butyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula X-O, formula X-R, formula XI-O, formula XI-R, formula XII-O, or formula XII-R where $R_{11}$, $R_{12}$, and $R_{13}$ are independently selected from —$C_1$-$C_4$ alkyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula X-O, formula X-R, formula XI-O, formula XI-R, formula XII-O, or formula XII-R where $R_{11}$, $R_{12}$, and $R_{13}$ are independently selected from —$C_1$-$C_4$ n-alkyl; and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formulas VII-i, VIII-i, or IX-i, and all salts, stereoisomers, mixtures of stereoisomers, prodrugs, metabolites, solvates, and hydrates thereof. Compound VII-i is:

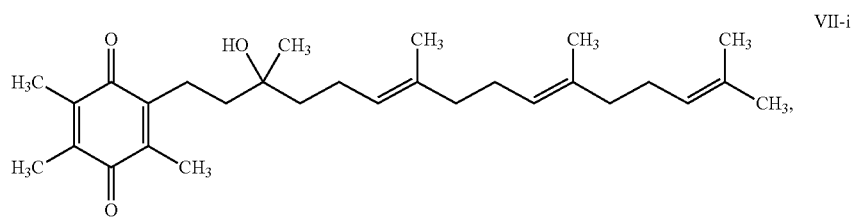 [SMILES: CC(C)=CCC/C(C)=C/CC/C(C)=C/CCC(C)(O)CCC1=C(C)C(=O)C(C)=C(C)C1=O]

VII-i which is α-tocotrienolquinone (alternatively named as 2-(3-hydroxy-3,7,11,15-tetramethyl-6,10,14-hexadecatrienyl)-3,5,6-trimethyl-2,5-cyclohexadiene-1,4-dione or 2-(3-hydroxy-3,7,11,15-tetramethyl-6,10,14-hexadecatrienyl)-3,5,6-trimethyl-p-benzoquinone, CAS Registry number 14101-66-7). Compound VIII-i is:

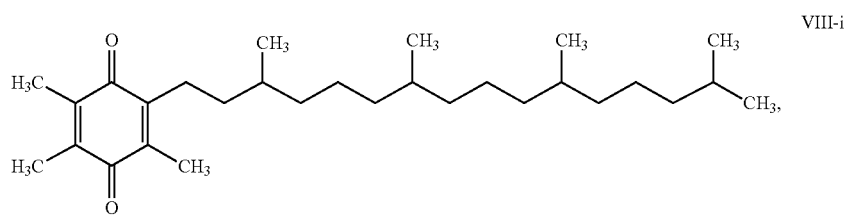 [SMILES: CC1=C(C)C(=O)C(CCC(C)CCCC(C)CCCC(C)CCCC(C)C)=C(C)C1=O]

VIII-i which, is 2,3,5-trimethyl-6-(3,7,11,15-tetramethylhexadecyl)-2,5-cyclohexadiene-1,4-dione (alternatively named 6-(3,7,11,15-tetramethylcetyl)-p-pseudocumoquinone, CAS Registry number 75917-94-1). Compound IX-i is:

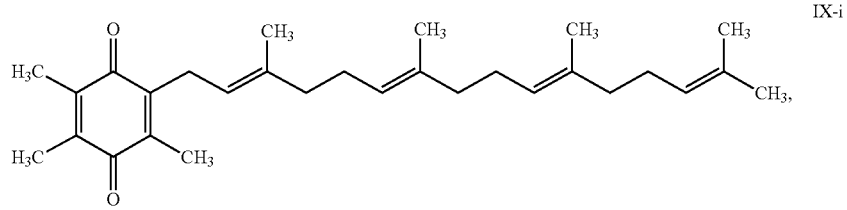 [SMILES: CC(C)=CCC/C(C)=C/CC/C(C)=C/CC/C(C)=C/CC1=C(C)C(=O)C(C)=C(C)C1=O]

which is 2,3,5-trimethyl-6-(3,7,11,15-tetramethyl-2,6,10,14-hexadecatetraenyl)-2,5-cyclohexadiene-1,4-dione (alternatively named trimethyl(3,7,11,15-tetramethyl-2,6,10,14-hexadecatetraenyl)-p-benzoquinone, CAS Registry Number 65647-38-3).

In other embodiments, including any of the foregoing embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Disease; Kearns-Sayre Syndrome (KSS); Friedreich's Ataxia (FA); other myopathies; cardiomyopathy; encephalomyopathy; renal tubular acidosis; neurodegenerative diseases; Parkinson's disease; Alzheimer's disease; amyotrophic lateral sclerosis (ALS); motor neuron diseases; other neurological diseases; epilepsy; genetic diseases; Huntington's Disease; mood disorders; schizophrenia; bipolar disorder; age-associated diseases; macular degeneration; diabetes; and cancer.

In another embodiment, including any of the foregoing embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Disease; Kearns-Sayre Syndrome (KSS); and Friedreich's Ataxia (FA).

In another embodiment of the invention, including any of the foregoing embodiments, the mitochondrial disorder is Friedreich's ataxia (FRDA). In another embodiment of the invention, the mitochondrial disorder is Leber's Hereditary Optic Neuropathy (LHON). In another embodiment of the invention, the mitochondrial disorder is mitochondrial myopathy, encephalopathy, lactacidosis, stroke (MELAS). In another embodiment of the invention, the mitochondrial disorder is Kearns-Sayre Syndrome (KSS). In another embodiment of the invention, the mitochondrial disorder is Myoclonic Epilepsy with Ragged Red Fibers (MERRF). In another embodiment of the invention, the mitochondrial disorder is Parkinson's disease.

In another embodiment of the invention, including any of the foregoing embodiments, the compounds described herein are administered to subjects suffering from a mitochondrial disorder to modulate one or more of various energy biomarkers, including, but not limited to, lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH(NADH+H$^+$) or NADPH(NADPH+H$^+$) levels; NAD or NADP levels; ATP levels; reduced coenzyme Q (CoQ$^{red}$) levels; oxidized coenzyme Q (CoQ$^{ox}$) levels; total coenzyme Q (Coq$^{tot}$) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), respiratory quotient (VCO2/VO2), and to modulate exercise intolerance (or conversely, modulate exercise tolerance) and to modulate anaerobic threshold. Energy biomarkers can be measured in whole blood, plasma, cerebrospinal fluid, cerebroventricular fluid, arterial blood, venous blood, or any other body fluid, body gas, or other biological sample useful for such measurement. In one embodiment, the levels are modulated to a value within about 2 standard deviations of the value in a healthy subject. In another embodiment, the levels are modulated to a value within about 1 standard deviation of the value in a healthy subject. In another embodiment, the levels in a subject are changed by at least about 10% above or below the level in the subject prior to modulation. In another embodiment, the levels are changed by at least about 20% above or below the level in the subject prior to modulation. In another embodiment, the levels are changed by at least about 30% above or below the level in the subject prior to modulation. In another embodiment, the levels are changed by at least about 40% above or below the level in the subject prior to modulation. In another embodiment, the levels are changed by at least about 50% above or below the level in the subject prior to modulation. In another embodiment, the levels are changed by at least about 75% above or below the level in the subject prior to modulation. In another embodiment, the levels are changed by at least about 100% above or at least about 90% below the level in the subject prior to modulation.

In another embodiment, including any of the foregoing embodiments, the subject or subjects in which a method of treating or suppressing a mitochondrial disorder, modulating one or more energy biomarkers, normalizing one or more energy biomarkers, or enhancing one or more energy biomarkers is performed is/are selected from the group consisting of subjects undergoing strenuous or prolonged physical activity; subjects with chronic energy problems; subjects with chronic respiratory problems; pregnant females; pregnant females in labor; neonates; premature neonates; subjects exposed to extreme environments; subjects exposed to hot environments; subjects exposed to cold environments; subjects exposed to environments with lower-than-average oxygen content; subjects exposed to environments with higher-than-average carbon dioxide content; subjects exposed to environments with higher-than-average levels of air pollution; airline travelers; flight attendants; subjects at elevated altitudes; subjects living in cities with lower-thanaverage air quality; subjects working in enclosed environments where air quality is degraded; subjects with lung diseases; subjects with lower-than-average lung capacity; tubercular patients; lung cancer patients; emphysema patients; cystic fibrosis patients; subjects recovering from surgery; subjects recovering from illness; elderly subjects; elderly subjects experiencing decreased energy; subjects suffering from chronic fatigue; subjects suffering from chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

In another embodiment, the invention embraces one or more compounds of formula I, Ia, Ib, II, IIa, IIb, III, IIIa, IIIb, IV, IVa, IVb, V, Va, Vb, VI, VIa, VIb, VII-O, VIII-R, VIII-R, IX-O, IX-R, X-O, X-R, XI-O, XI-R, XII-O, and/or XII-R, in combination with a pharmaceutically acceptable excipient, carrier, or vehicle.

In another embodiment, the invention embraces the use of one or more compounds of formula I, Ia, Ib, II, ha, IIb, III, IIIa, IIIb, IV, IVa, IVb, V, Va, Vb, VI, VIa, VIb, VII-O, VII-R, VIII-O, VIII-R, IX-O, IX-R, X-O, X-R, XI-O, XI-R, XII-O, and/or XII-R in therapy. In another embodiment, the invention embraces the use of one or more compounds of formula I, Ia, Ib, II, IIa, IIb, III, Ma, IIIb, IV, IVa, IVb, V, Va, Vb, VI, VIa, VIb, VII-O, VII-R, VIII-O, VIII-R, IX-O, IX-R, X-O, X-R, XI-O, XI-R, XII-O, and/or XII-R in the therapy of mitochondrial disease. In another embodiment, the invention embraces the use of one or more compounds of formula I, Ia, Ib, II, IIa, IIb, III, IIIa, IIIb, IV, IVa, IVb, V, Va, Vb, VI, VIa, VIb, VII-O, VII-R, VIII-O, VIII-R, IX-O, IX-R, X-O, X-R, XI-O, XI-R, XII-O, and/or XII-R in the manufacture of a medicament for use in therapy of mitochondrial disease.

For all of the compounds and methods described above, the quinone form can also be used in its reduced (hydroquinone) form when desired. Likewise, the hydroquinone form can also be used in its oxidized (quinone) form when desired.

MODES FOR CARRYING OUT THE INVENTION

The invention embraces compounds useful in treating or suppressing mitochondrial disorders, and methods of using such compounds for modulation of energy biomarkers. The redox active therapeutics for treatment or suppression of mitochondrial diseases and associated aspects of the invention are described in more detail herein.

By "subject," "individual," or "patient" is meant an individual organism, preferably a vertebrate, more preferably a mammal, most preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. Because many of the mitochondrial disorders are inherited, genetic screening can be used to identify patients at risk of the disease. The compounds and methods of the invention can then be administered to asymptomatic patients at risk of developing the clinical symptoms of the disease, in order to suppress the appearance of any adverse symptoms. "Therapeutic use" of the compounds discussed herein is defined as using one or more of the compounds discussed herein to treat or suppress a disease, as defined above. An "effective amount" of a compound is an amount of the compound sufficient to modulate, normalize, or enhance one or more energy biomarkers (where modulation, normalization, and enhancement are defined below). A "therapeutically effective amount" of a compound is an amount of the compound, which, when administered to a subject, is sufficient to reduce or eliminate either a disease or one or more symptoms of a disease, or to retard the progression of a disease or of one or more symptoms of a disease, or to reduce the severity of a disease or of one or more symptoms of a disease, or to suppress the clinical manifestation of a disease, or to suppress the manifestation of adverse symptoms of a disease. A therapeutically effective amount can be given in one or more administrations. An "effective amount" of a compound embraces both a therapeutically effective amount, as well as an amount effective to modulate, normalize, or enhance one or more energy biomarkers in a subject.

"Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and enhancement as defined below.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. That is, to normalize an energy biomarker which is depressed in a disease state means to increase the level of the energy biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. For example, in a situation where significant energy demands are placed on a subject, it may be desirable to increase the level of ATP in that subject to a level above the normal level of ATP in that subject. Enhancement can also be of beneficial effect in a subject suffering from a disease or pathology such as a mitochondrial disease, in that normalizing an energy biomarker may not achieve the optimum outcome for the subject; in such cases, enhancement of one or more energy biomarkers can be beneficial, for example, higher-than-normal levels of ATP, or lower-than-normal levels of lactic acid (lactate) can be beneficial to such a subject.

By modulating, normalizing, or enhancing the energy biomarker Coenzyme Q is meant modulating, normalizing, or enhancing the variant or variants of Coenzyme Q which is predominant in the species of interest. For example, the variant of Coenzyme Q which predominates in humans is Coenzyme Q10. If a species or subject has more than one variant of Coenzyme Q present in significant amounts (i.e., present in amounts which, when modulated, normalized, or enhanced, can have a beneficial effect on the species or subject), modulating, normalizing, or enhancing Coenzyme Q can refer to modulating, normalizing or enhancing any or all variants of Coenzyme Q present in the species or subject.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts. Salts of acidic compounds with amino acids, such as lysine salts, can also be prepared.

The invention also includes all stereoisomers of the compounds, including diastereomers and enantiomers. The invention also includes mixtures of stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds which are themselves relatively inactive, but which convert into the active compound when introduced into the subject in which they are used, by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, Design of Prodrugs, New York: Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New. York Academy of Sciences, v. 507), New York: N.Y. Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

The various compounds of the invention, particularly compounds V, Va, Vb, VI, VIa, and VIb, as well as their various embodiments, can be administered either as therapeutic agents in and of themselves, or as prodrugs which will convert to other therapeutically effective or effective substances in the body.

Metabolites of the compounds are also embraced by the invention. However, metabolites of substances which occur naturally in subjects, such as metabolites of alpha-tocopherol quinone, are excluded from the claimed compounds of the invention.

"$C_1$-$C_4$ alkyl" is intended to embrace methyl (Me), ethyl (Et), propyl (Pr), n-propyl (nPr), isopropyl (iPr), butyl (Bu), n-butyl (nBu), isobutyl (iBu), sec-butyl (sBu), t-butyl (tBu), cyclopropyl (cyclPr), cyclobutyl (cyclBu), cyclopropyl-methyl (cyclPr-Me) and methyl-cyclopropane (Me-cyclPr), where the $C_1$-$C_4$ alkyl groups can be attached via any valence on the $C_1$-$C_4$ alkyl groups.

"Halogen" or "halo" substituents designates fluoro (—F), chloro (—Cl), bromo (—Br), and iodo (—I).

"$C_1$-$C_4$ haloalkyl" is intended to embrace any $C_1$-$C_4$ alkyl substituent having at least one halogen substituent; the halogen can be attached via any valence on the $C_1$-$C_4$ alkyl group. One subset of $C_1$-$C_4$ haloalkyl is —$CF_3$, —$CCl_3$, —$CBr_3$, and —$CI_3$. Another subset of $C_1$-$C_4$ haloalkyl is the subset with exactly one halogen substituent. Another subset of $C_1$-$C_4$ haloalkyl is the subset of $C_1$-$C_4$ perhaloalkyl; that is, $C_1$-$C_4$ alkyl with all available valences replaced by halogens. Another subset of $C_1$-$C_4$ haloalkyl is the subset of $C_1$-$C_4$ perfluoroalkyl; that is, $C_1$-$C_4$ alkyl with all available valences replaced by fluorines. Another subset of $C_1$-$C_4$ haloalkyl is the subset of $C_1$-$C_4$ perchloroalkyl; that is, $C_1$-$C_4$ alkyl with all available valences replaced by chlorines.

One compound of interest, which can be used in any of the methods of the invention, is α-tocopherol quinone. The structure of alpha-tocopherol quinone (D-α-tocopherol quinone; alpha-tocopherylquinone; 2-[(3R,7R,11R)-3-hydroxy-3,7,11,15-tetramethylhexadecyl]-3,5,6-trimethyl-2,5-cyclohexadiene-1,4-dione, CAS Registry number 7559-04-8) is:

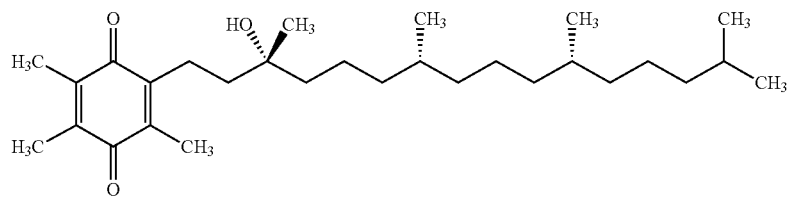 [SMILES: CC1=C(C)C(=O)C(CC[C@](C)(O)CCC[C@H](C)CCC[C@H](C)CCCC(C)C)=C(C)C1=O]

An alternate name for alpha-tocopherol quinone is alpha-tocopherylquinone. This compound corresponds to the compound of formula IIb where $R_{11}$, $R_{12}$, and $R_{13}$ are all methyl. In human cell culture models of FRDA, alpha-tocopherol quinone possesses an $EC_{50}$ $10^5$-fold lower (i.e., 100,000 times more potent) than idebenone, the current therapeutic agent of choice for FRDA patients; see Example 2. In this same cell culture model, alpha-tocopherol quinone has an $EC_{50}$ $10^4$-fold lower (i.e., 10,000 times more potent) than alpha-D-tocopherol, (2R)-3,4-dihydro-2,5,7,8-tetramethyl-2-[(4R,8R)-4,8,12-trimethyltridecyl]-2H-1-benzopyran-6-ol, a common form of vitamin E.

Another group of compounds of interest are represented by formula IIm:

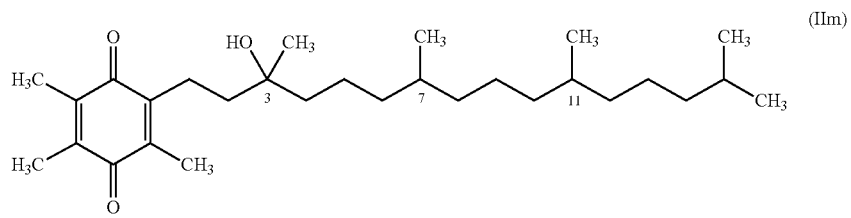 [SMILES: CC1=C(C)C(=O)C(CCC(C)(O)CCCC(C)CCCC(C)CCCC(C)C)=C(C)C1=O]

where the lack of indication of stereochemistry indicates that this structure is intended to represent all eight possible stereoisomers, as there are 2 different orientations possible at the 3, 7, and 11 positions as indicated in the drawing of formula IIm. Formula Um corresponds to formula II where $R_{11}$, $R_{12}$, and $R_{13}$ are all methyl. The eight stereoisomers embraced by this structure drawing include: [(3R,7R,11R)-3-hydroxy-3,7,11,15-tetramethylhexadecyl]-3,5,6-trimethyl-2,5-cyclohexadiene-1,4-dione); the 3R, 7R,11S-compound; the 3R, 7S,11R-compound; the 3S,7R,11R-compound; the 3R,7S,11S-compound; the 3S,7R,11S-compound; the 3S,7S,11R-compound; and the 3S,7S,11S-compound.

Synthesis of Compounds of Formula I and Formula II

The compounds of formula I and formula II can be readily synthesized by a variety of methods. The synthesis of alpha-tocopherol quinone is detailed in several references, e.g., U.S. Pat. No. 3,406,188 (GB 1,059,155) and U.S. Pat. No. 4,310,465. The synthesis of benzoquinone-type compounds is disclosed in U.S. Pat. Nos. 5,229,385 and 4,393,075.

In several of the following methods, an oxidizing agent is used. Suitable oxidizing agents which can be used in the synthetic methods include, but are not limited to, ceric ammonium nitrate (CAN), $FeCl_3$, 2,3-dichloro-5,6-dicyano-1,4-benzoquinone (DDQ), or atmospheric oxygen (i.e., air oxidation).

Several methods can be used to make the compounds of Formulas I, Ia, Ib, II, IIa, IIb, III, IIIa, IIIb, IV, IVa, and IVb. One such method utilizes an oxysulfonium rearrangement as follows:

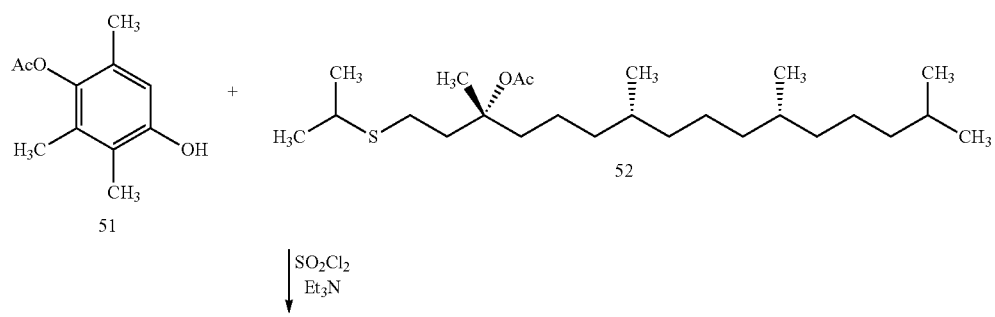

-continued

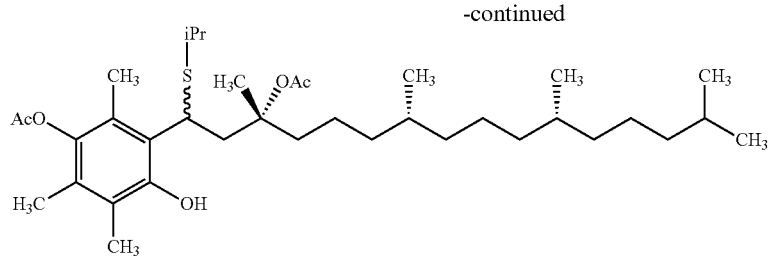

53

1) Raney Ni, EtOH
2) LiAlH$_4$, Et$_2$O

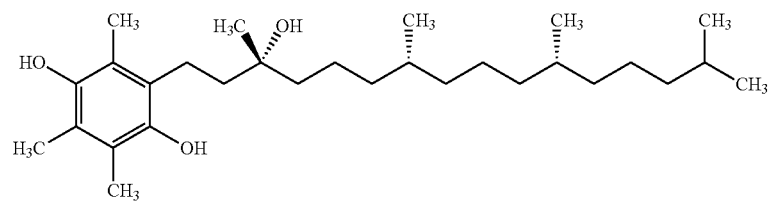

54

FeCl$_3$

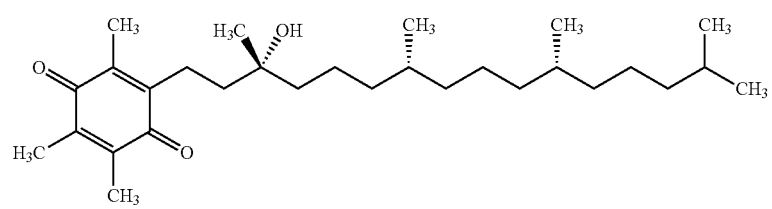

55

The starting material 4-hydroxy-2,3,6-trimethyl phenyl acetate, 51, is prepared as described in Weichet et al., Coll. Czech. Chem. Comm. 31:4598 (1966). Compound 52 is prepared and reacted with compound 51 and sulfuryl chloride as in Inoue et al., J. Org. Chem. Soc. 52:5495 (1987) to yield compound 53. Removal of the isopropyl-sulfur moiety with Raney nickel, followed by removal of the acetyl groups with lithium aluminum hydride, yields the hydroquinone compound 54 corresponding to Formula IVb where $R_{11}$, $R_{12}$, and $R_{13}$ are methyl. Oxidation of the hydroquinone compound 54 with iron (III) chloride (Shiraishi et al., J. Med. Chem. 32:2214-2221 (1989)) yields the quinone compound 55 corresponding to Formula III where $R_{11}$, $R_{12}$, and $R_{13}$ are methyl.

By using starting material of the form:

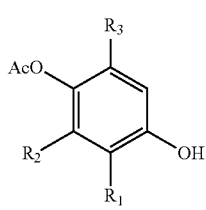

in place of 51, the entire range of compounds of Formulas I, Ia, Ib, II, IIa, IIb, III, IIIa, IIIb, IV, IVa, and IVb can be synthesized. (For the compounds of Formulas III, IIIa, IIIb, IV, IVa, and IVb, the synthesis would be completed after the Raney nickel and lithium aluminum hydride treatment, before the FeCl$_3$ oxidation.) The dihydroquinone starting material can be prepared by a variety of processes, e.g., those described in U.S. Pat. Nos. 3,909,376, 5,132,468, and 6,303,801, and in German Patent No. DE 3818696; the acetylated dihydroquinone precursor for the synthesis above can then be prepared as in Weichet et al., Coll. Czech. Chem. Comm. 31:4598 (1966).

An alternative method for synthesizing compounds of Formulas I, Ia, Ib, II, IIa, and IIb utilizes an epoxide opening as described in Hübscher et al., Helvetica Chimica Acta 73:1068-1083 (1990).

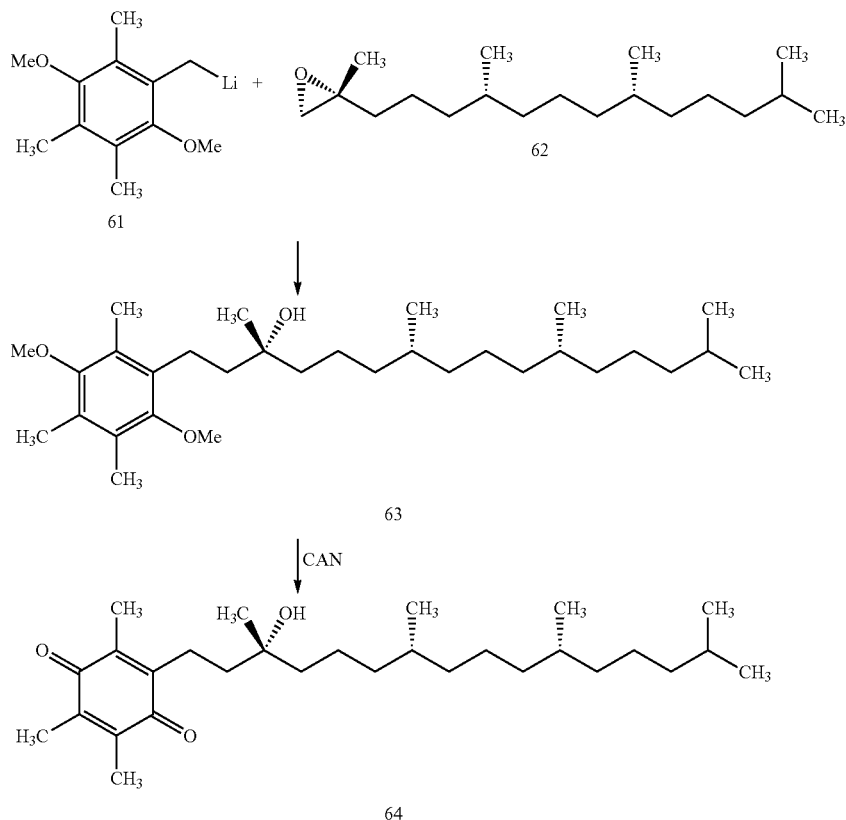

2,5-dimethoxy-3,4,6-trimethyl benzyllithium 61 is reacted with the epoxide compound 62 to yield 1,4-dimethoxybenzene derivative 63. Subsequent oxidation with ceric ammonium nitrate (CAN) yields the compound 64 corresponding to Formula IIb where $R_{11}$, $R_{12}$, and $R_{13}$ are methyl.

An additional method of synthesizing compounds of Formulas I, Ia, Ib, II, IIa, and IIb makes use of a Claisen rearrangement as follows, in a procedure adapted from Green et al., J. Chem. Soc. (C) 1422 (1966) and Zheng et al., J. Org. Chem. 64:156 (1999).

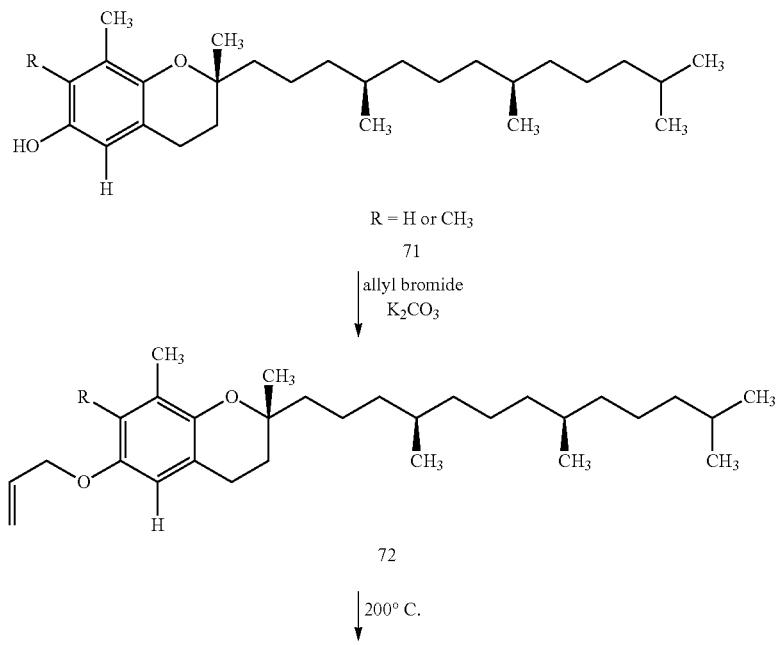

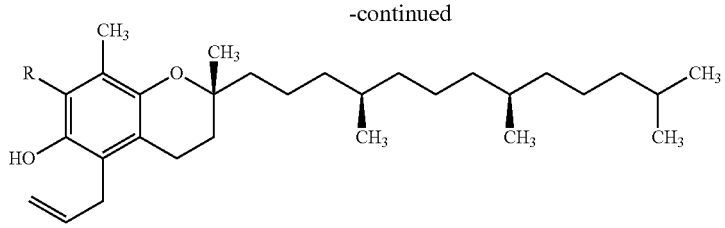

73

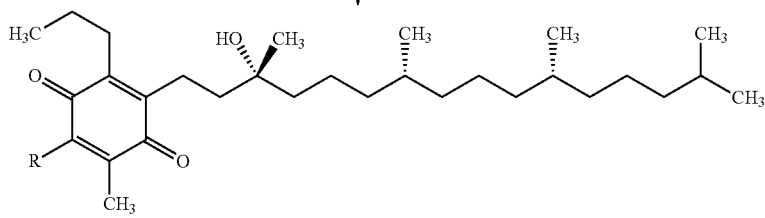

74

An allyl group is introduced onto 71 to yield 72, and then subjected to conditions that cause rearrangement to 73 (e.g., in the manner as described in Scheme 3 of Zheng et al., J. Org. Chem. 64:156 (1999)). Hydrogenation of 73 (e.g., with palladium on charcoal) then yields the propyl-substituted hydroquinone (not depicted) (e.g., for compounds of formulas III, IIIa, IIIb, IV, IVa, and IVb); subsequent oxidation with $FeCl_3$ yields the propyl-substituted quinone 74 (e.g., for compounds of formulas I, Ia, Ib, II, IIa, and IIb).

Another method of synthesizing the compounds of Formulas I, Ia, Ib, II, IIa, and IIb, as well as synthesizing compounds of Formulas V, Va, Vb, VI, VIa, and VIb utilizes an aldehyde condensation (Adelwöhrer et al., Tetrahedron 61:9070 (2005)) as follows.

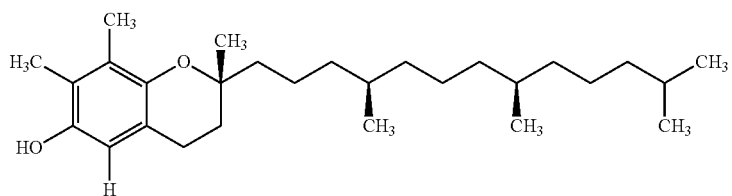

81

RCHO
$H_2SO_4$, AcOH
(R = alkyl)

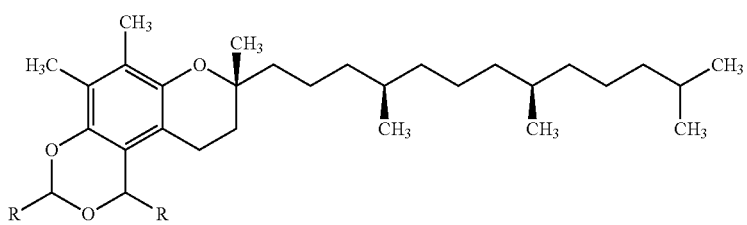

82

$H_2$, Pd/C
AcOH, $H_2SO_4$

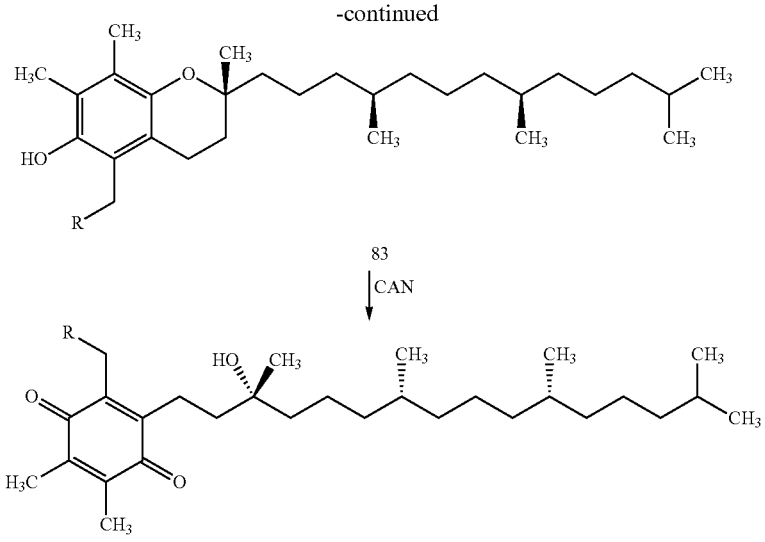

Starting with a γ-tocopherol compound 81, a fused dioxane-chroman compound 82 is formed. Hydrogenation with palladium on charcoal yields the chroman compound 83 (e.g., compounds of formulas V, Va, Vb, VI, VIa, and VIb), while ceric ammonium nitrate (CAN) oxidation then yields the quinone compounds (e.g., compounds of formulas I, Ia, Ib, II, IIa, and IIb).

A method of synthesizing compounds of the formula:

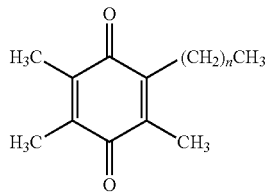

(95)

is as follows:

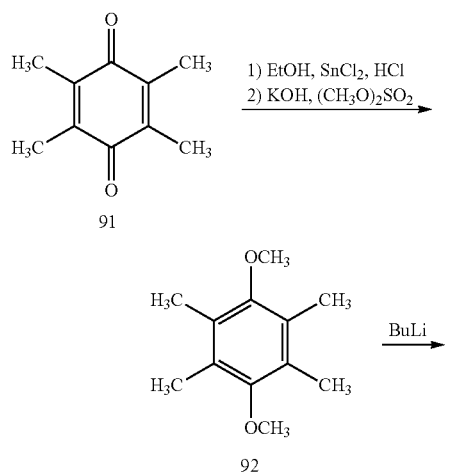

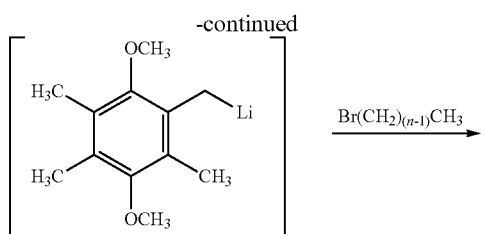

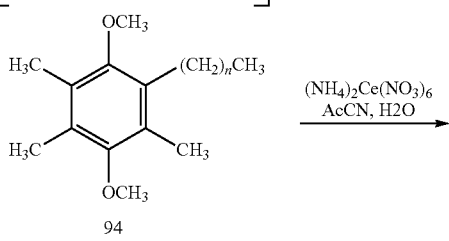

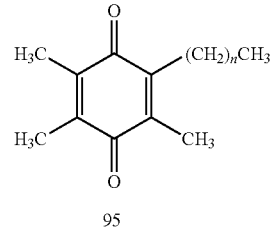

where the chemistry for conversion of duroquinone 91 into 3,6-dimethoxy-1,2,4,5-tetramethyl-1,4-cyclohexadiene 92 is described in Thomas et al., Journal of Organic Chemistry 51(22):4160 (1986); the chemistry for conversion of 3,6-dimethoxy-1,2,4,5-tetramethyl-1,4-cyclohexadiene 92 into the 3,6-dimethoxy-1-methylene lithium-2,4,5-trimethyl-1,4-cyclohexadiene 93 intermediate is described in Hübscher et al., Helvetica Chimica Acta 73(4):1068 (1990); and the chemistry for conversion of the 3,6-dimethoxy-1-alkyl-2,4,5-trimethyl-1,4-cyclohexadiene 94 into the 2-alkyl-3,5,6-trimethyl-1,4-benzoquinone 95 is described in Shiraishi et al., Journal of Medicinal Chemistry 32(9):2214 (1989). This synthesis can be easily modified to produce compounds of formula IIm:

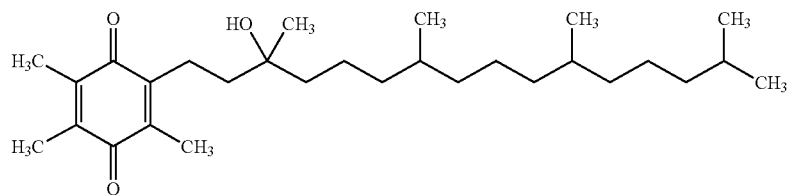 [SMILES: CC1=C(C)C(=O)C(CCC(C)(O)CCCC(C)CCCC(C)CCCC(C)C)=C(C)C1=O]

10 by using the following intermediate:

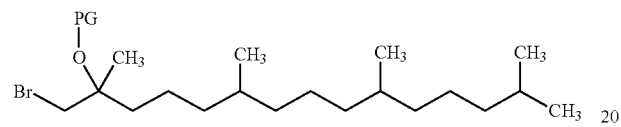

(99)

where PG indicates a protecting group, such as a methyl methoxymethyl (MOM) or methoxy ethoxymethyl (MEM) group. Other suitable protecting groups, for this and other reactions described herein, are detailed in the text by Theodora W. Greene and Peter G. M. Wuts, Protective Groups in Organic Synthesis, 3rd edition, Hoboken, N.J.: Wiley-Interscience, 1999.

Another method of making compounds of the formula 95 is as follows:

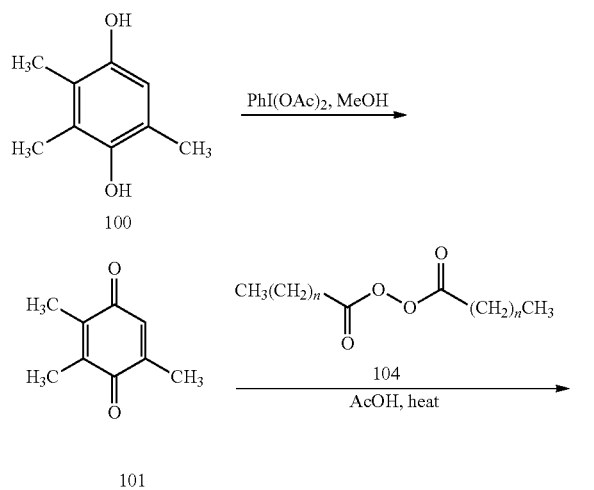

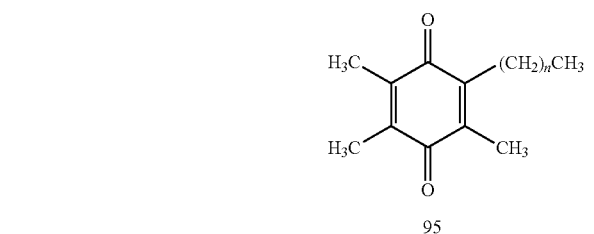

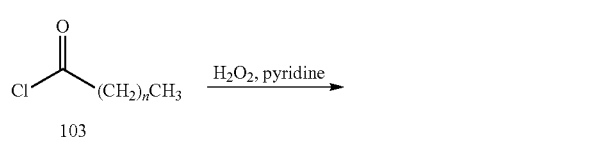

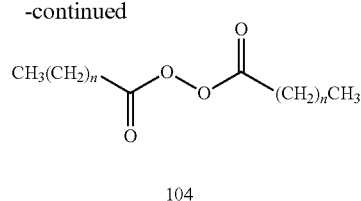

104 where the chemistry of converting 1,4-hydroxy-2,3,5-trimethylbenzene 100 into 2,3,5-trimethyl-1,4-benzoquinone 101 is described in Pelter et al., J. Chem. Soc., Perkin Trans. 1, (16), 1891 (1993), the chemistry of converting the benzoquinone compound 102 into the 2-alkyl-3,5,6-trimethyl-1,4-benzoquinone 95 is described in Fieser et al., Journal of the American Chemical Society 64(9):2060 (1942), and the chemistry of converting the alkanoyl chloride 103 into the dialkanoyl peroxide 104 is described in Silbert et al., Journal of the American Chemical Society 81(10):2364 (1959). The alkanoyl chloride 106

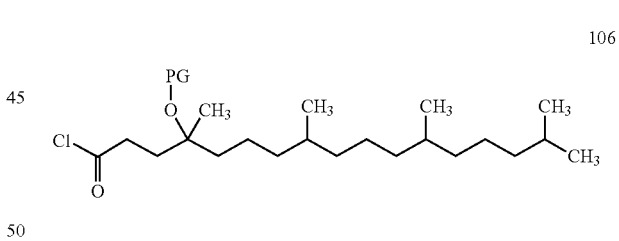

106 can be used to prepare compounds of the formula IIm via this route. Compounds of formula I and formula II can be prepared via this route by starting with the appropriate 1,4-dihydroxy-2,3,5-substituted-1,4-benzoquinone and using the intermediate 106.

Methods suitable for making compounds of the inventions with halogen substituents on the quinone ring are depicted as follows. (See Fujishima et al. Arch. Pharm. Pharm. Med. Chem. 329:27-34 (1996) for additional information.)

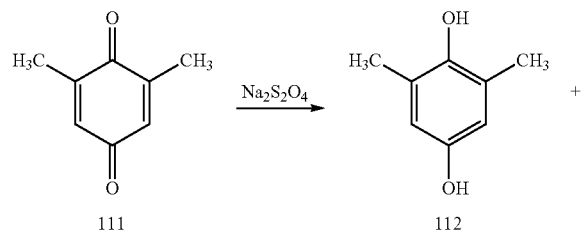
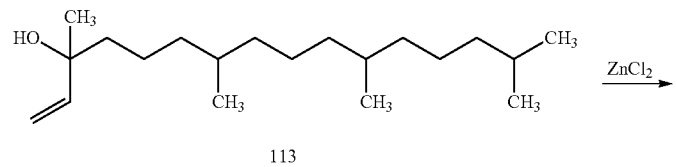
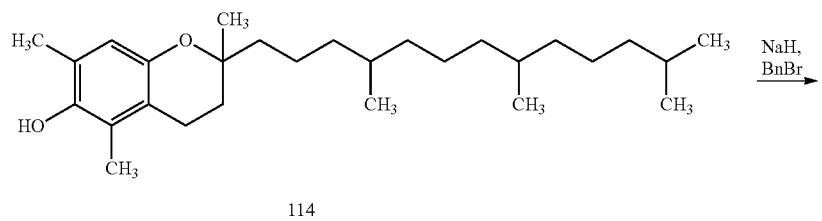
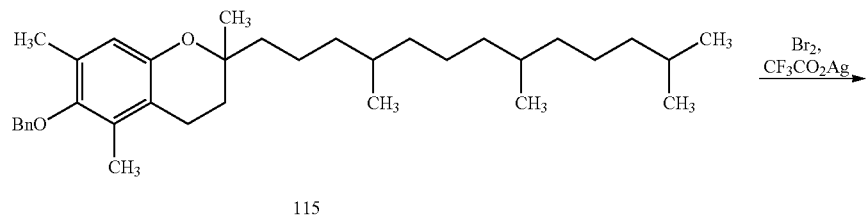
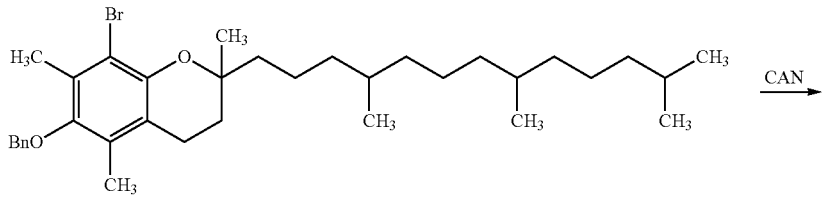
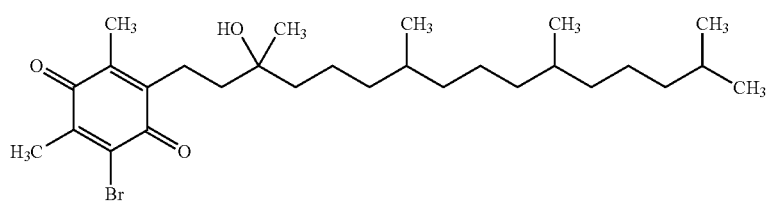

2,6-dimethylquinone 111 is reduced with sodium dithionite to the hydroquinone 112, which is then reacted with 3,7,11, 15-tetramethyl-3-hydroxy-1-hexadecene 113 and ZnCl₂ to form the 6-chromanol 114. Conversion to the protected intermediate 115 is followed by bromination with Br₂ and silver trifluoroacetate to form the bromide 116. Finally, 116 can be deprotected and oxidized with ceric ammonium nitrate (CAN) to yield 117.

Iodine can be introduced onto the quinone ring using a procedure as outlined in the following scheme (see Kumadaki, I. et al. Synthetic Communications 19:173-177 (1989) for more information).

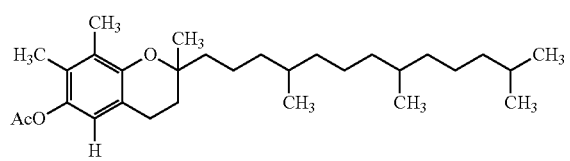

120

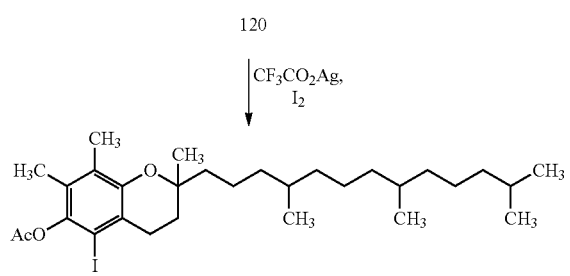

121

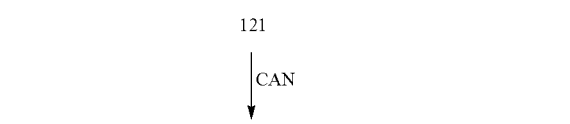

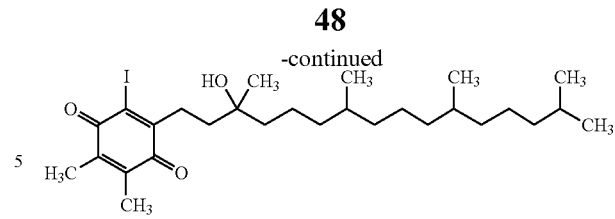

122

The protected chromanol 120 is treated with I₂ and silver trifluoroacetate to yield the iodinated derivative 121, followed by deprotection/oxidation with ceric ammonium nitrate to give 122.

A method suitable for synthesizing nitrile-containing compounds of formula I, formula II, formula III, formula IV, formula V, formula VI, formula VII, formula VIII, formula IX, formula X, formula XI, or formula XII (including all variations on the formulas) is depicted in the following scheme. The scheme illustrates the synthesis starting from α-tocopherol and ending in the cyano-substituted quinone, but can be readily generalized to the other compounds of the invention by using appropriate groups in place of the 2-methyl and 3-methyl groups and the appropriate tail group.

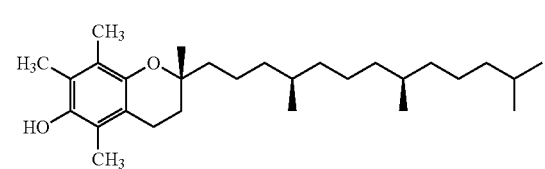

α-tocopherol
131

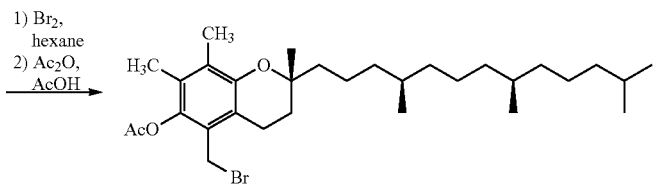

132

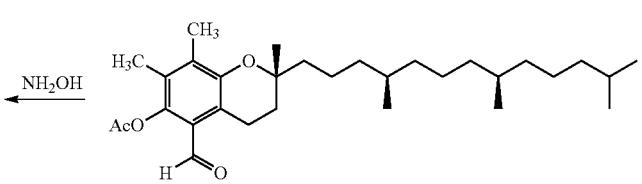

Mazzini, F. et al. Tetrahedron, 2005, 813-817.
133

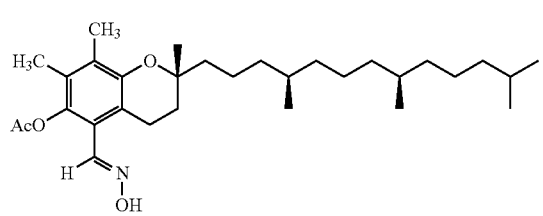

134

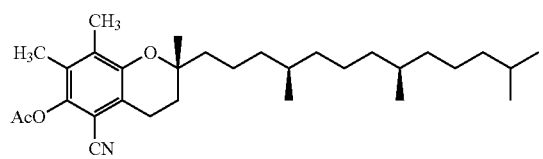 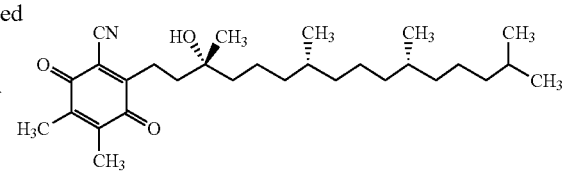

135 136

The synthesis from conversion of α-tocopherol 131 to the 5-bromomethyl derivative with acetate-protected 6-hydroxy group 132, followed by oxidation to the aldehyde intermediate 133 with anhydrous N-methylmorpholine-N-oxide (NMMO), is described in Mazzini et al., Tetrahedron 813-817 (2005). Hydroxylamine is then used to form an oxime 134, followed by dehydration of the oxime with acetic anhydride (see, e.g., the procedure described in Organic Syntheses, Coll. Vol. 3, p. 690 (1955); Vol. 20, p. 74 (1940)) to give 135. Removal of the acetate protection groups, and oxidation with ceric ammonium nitrate (CAN) yields 136.

Another method suitable for synthesizing nitrile-containing compounds of formula I, formula II, formula III, formula IV, formula V, formula VI, formula VII, formula VIII, formula IX, formula X, formula XI, or formula XII (including all variations on the formulas) is depicted in the following scheme, starting from intermediate 114 from one of the syntheses depicted above for making compounds of the inventions with halogen substituents on the quinone ring.

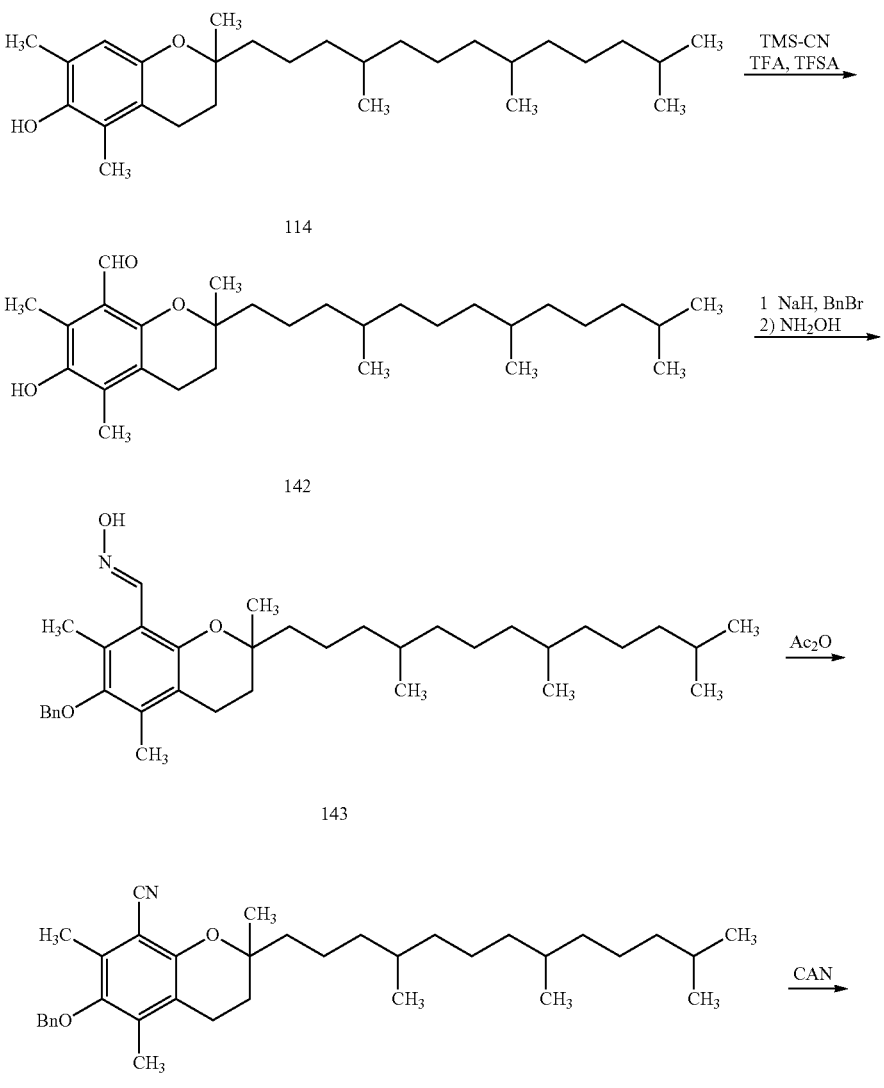

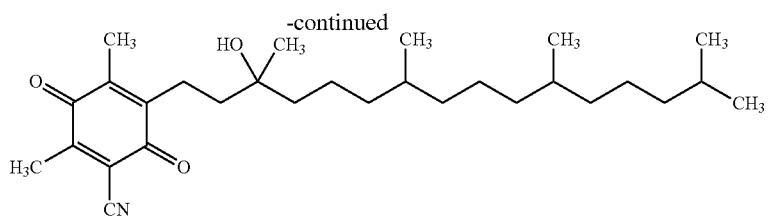

145

Compound 114 is treated with trimethylsilyl cyanide and trifluoromethane sulfonic acid in trifluoroacetic acid to introduce the formyl group, resulting in compound 142. The phenolic group is protected, and hydroxylamine is used to convert the aldehyde compound 142 into the oxime compound 143. Dehydration of the oxime to give the nitrile 144 can be followed by deprotection and oxidation to form 145; alternatively, 144 can be deprotected to give the 6-chromanol-type compounds. (See Fujishima et al. Arch. Pharm. Pharm. Med. Chem. 329:27-34 (1996) for additional information.)

The regioisomer 157

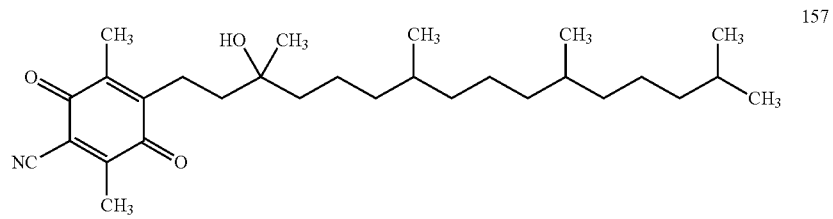 [SMILES: CC1=C(C#N)C(=O)C(C)=C(CCC(C)(O)CCCC(C)CCCC(C)CCCC(C)C)C1=O]

157 can be prepared by synthesizing the regioisomer 154

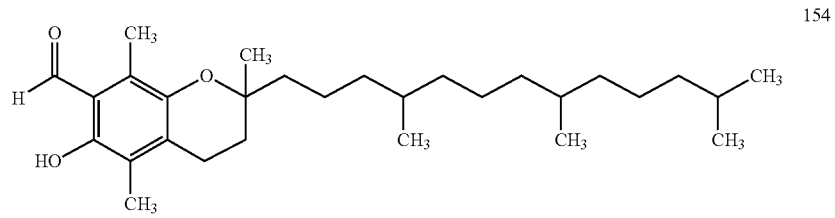 [SMILES: Cc1c(O)c(C=O)c(C)c2c1CCC(C)(CCCC(C)CCCC(C)CCCC(C)C)O2]

154 in a manner analogous to the synthesis of compound 9 described in Dean et al., Journal of the Chemical Society, Perkin Transactions 1: Organic and Bio-Organic Chemistry, (5) 1437-42 (1981), as outlined in the following scheme.

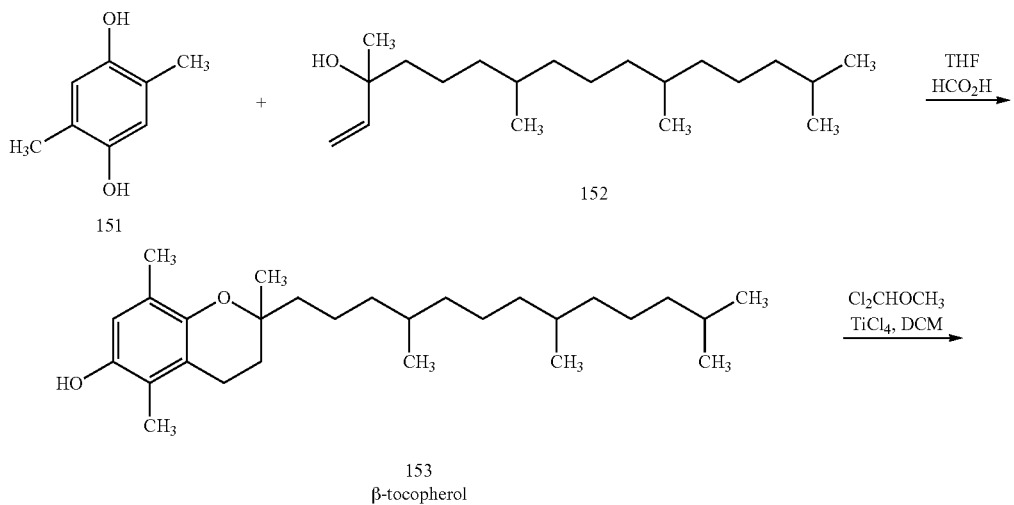

153
β-tocopherol

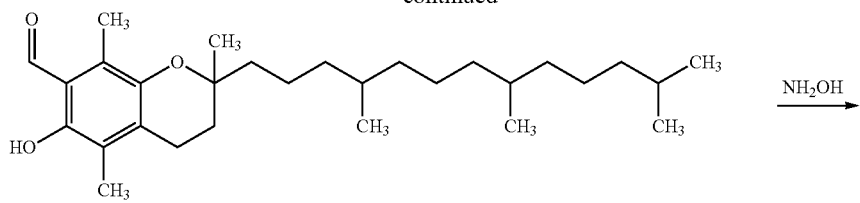
154
$\xrightarrow{NH_2OH}$
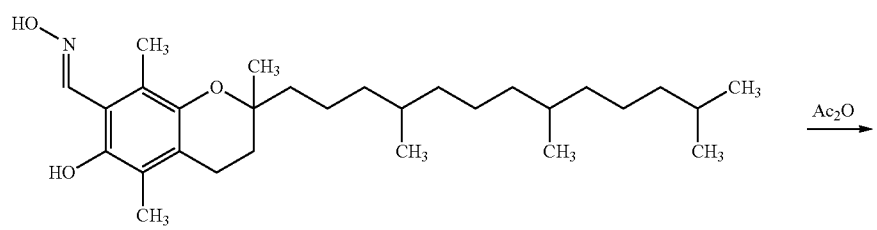
155
$\xrightarrow{Ac_2O}$
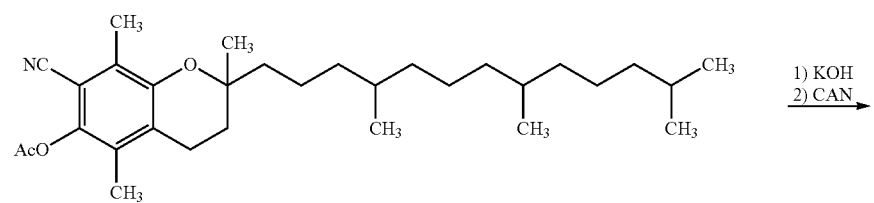
156
1) KOH
2) CAN
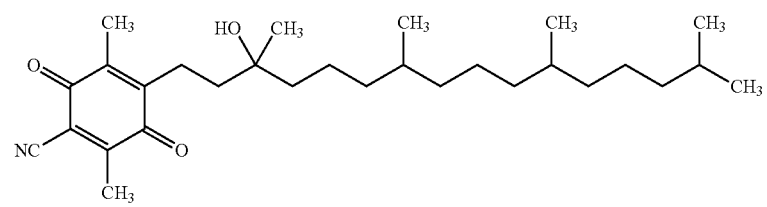
157

Synthesis of Compounds of Formula III and Formula IV

The compounds of formula III and of formula IV are similar to the compounds of formula I and formula II, except that the "head group" is a benzene-1,4-diol moiety instead of a 1,4-benzoquinone. That is, the head group of formulas III and IV is the reduced form of the head group of formulas I and II. Thus, compounds of formulas III and IV can be readily prepared by simple reduction of the compounds of formulas I and II. This reduction can be done chemically (e.g., with $Na_2S_2O_4$) or electrochemically, as is well known in the art.

Synthesis of Compounds of Formula V and Formula VI

The compounds of Formula V and Formula VI can be synthesized by the following procedure, as discussed in Omura, J. Org. Chem. 54:1987 (1989).

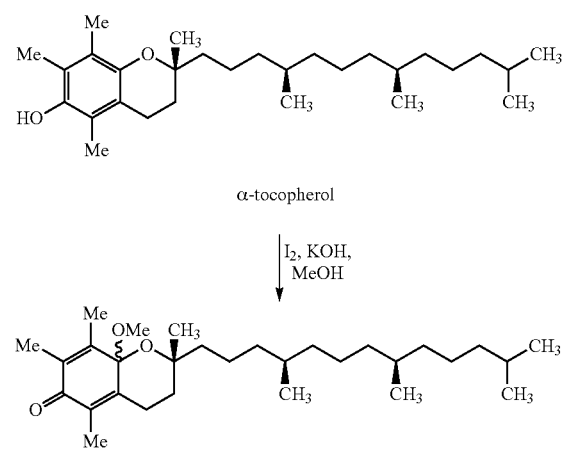

By using alcohols of the form $R_8OH$, other alkoxy groups can be introduced, in a manner analogous to the methoxy group introduction as illustrated. An alternative synthesis is described in Goodhue et al., Biochemistry 4:854 (1965).

The corresponding hydroxy compound ($R_8$=H for the compounds of general formula V and general formula VI) can be synthesized by the procedure described in Dürckheimer et al., J. Am. Chem. Soc. 86:4388 (1964), involving oxidation of alpha-tocopherol with tetrachloro-o-quinone in an acetonitrile/water mixture:

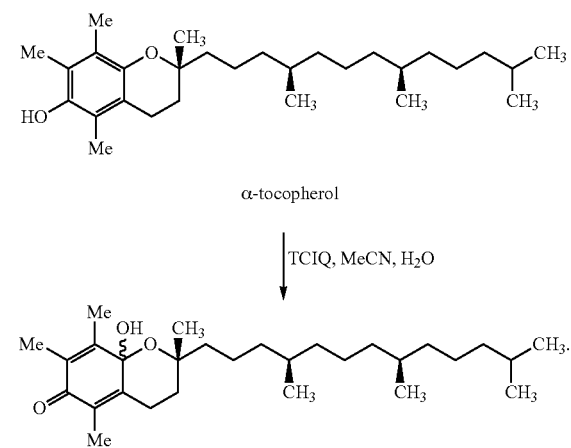

The compounds of formula V and formula VI can also be synthesized by treating the compounds of formula I or formula II with p-toluenesulfonic acid in benzene in the presence of $R_8OH$ ($R_8OH$ can be, e.g., methanol), as follows (adapted from Cohen et al., J. Org. Chem. 46:2445 (1981)).

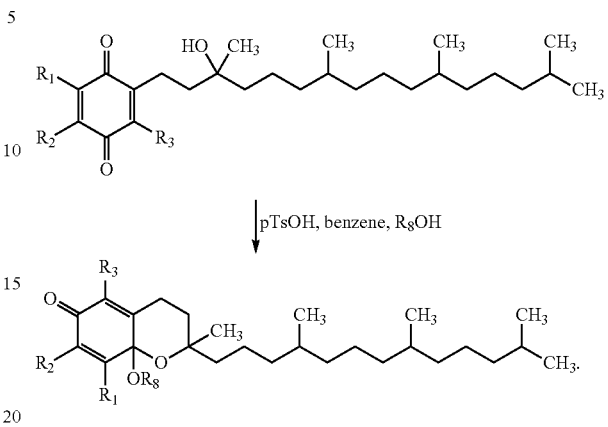

Compounds of Formula VII-i, Formula VIII-i, and Formula IX-i

Information pertaining to the compound of formula VII-i can be found in the following publications: US 2004/0116715; Storozhok et al., Biomeditsinskaya Khimiya (2003), 49(1), 96-104; Bertalan et al., Olaj, Szappan, Kozmetika (2000), 49(Kulonszam), 40-45; Dompert et al., Fette, Seifen, Anstrichmittel (1976), 78(3), 108-11; Berndorfer-Kraszner et al., Elelmezesi Ipar (1971), 25(11), 339-45; and Whittle et al., Biochemical Journal (1967), 103(3), 21C-22C.

Information pertaining to the compound of formula VIII-i can be found in the following publications: JP 58-193689; Mahmood et al., Phytochemistry (Elsevier) (1984), 23(8), 1725-7; Hughes et al., Journal of Biological Chemistry (1980), 255(24), 11802-6; Deuel et al., Journal of Biological Chemistry (1941), 139, 479-80; and Tishler et al., Journal of Biological Chemistry (1941), 139, 241-5. See Example 1 (Example 1A) below for a synthetic route to a mixture of stereoisomers of this compound.

Information pertaining to the compound of formula IX-i can be found in the following publications: JP 2003-137716 and JP 52-111576. See Example 1 (Example 1B) below for a synthetic route to a mixture of stereoisomers of this compound.

Interconvertibility of Quinone, Dihydroquinone Forms

The quinone and dihydroquinone forms of the compounds disclosed herein are readily interconverted with appropriate reagents. For example, the quinone form of a compound can be reduced to the dihydroquinone form with reducing agents such as sodium dithionite. The hydroquinone form can be oxidized to the quinone form with oxidizing agents such as ceric ammonium nitrate or ferric chloride. The quinone and hydroquinone forms are also readily converted electrochemically, as is well known in the art. See, e.g., Section 33.4 of Streitweiser & Heathcock, Introduction to Organic Chemistry, New York: Macmillan, 1976.

When the compounds of the invention are drawn as the quinone or hydroquinone form, that specific form is intended. However, when the quinone form is drawn and followed by the phrase "reduced counterpart thereof" or "reduced form" or the like, the structure and the subsequent phrase are intended to embrace both the quinone and hydroquinone. Similarly, when the hydroquinone form is drawn and followed by the phrase "oxidized counterpart thereof" or "oxidized form thereof" or the like, the structure and the subsequent phrase are intended to embrace both the hydroquinone and quinone.

Diseases Amenable to Treatment or Suppression with Compounds and Methods of the Invention A variety of diseases are believed to be caused or aggravated by mitochondrial disorders and impaired energy processing, and can be treated or suppressed using the compounds and methods of the invention. Such diseases include, but are not limited to, inherited mitochondrial diseases, such as Myoclonic Epilepsy with Ragged Red Fibers (MERRF), Mitochondrial Myopathy, Encephalopathy, Lactacidosis, Stroke (MELAS), Leber's Hereditary Optic Neuropathy (LHON, also referred to as Leber's Disease, Leber's Optic Atrophy (LOA), or Leber's Optic Neuropathy (LON)), Leigh Disease or Leigh Syndrome, Kearns-Sayre Syndrome (KSS), Friedreich's Ataxia (FA), other myopathies (including cardiomyopathy and encephalomyopathy), and renal tubular acidosis; neurodegenerative diseases, such as Parkinson's disease, Alzheimer's disease, amyotrophic lateral sclerosis (ALS, also known as Lou Gehrig's disease), motor neuron diseases; other neurological diseases such as epilepsy; genetic diseases such as Huntington's Disease (which is also a neurological disease); mood disorders such as schizophrenia and bipolar disorder; and certain age-associated diseases, particularly diseases for which CoQ10 has been proposed for treatment, such as macular degeneration, diabetes, and cancer.

Clinical Assessment of Mitochondrial Dysfunction and Efficacy of Therapy

Several readily measurable clinical markers are used to assess the metabolic state of patients with mitochondrial disorders. These markers can also be used as indicators of the efficacy of a given therapy, as the level of a marker is moved from the pathological value to the healthy value. These clinical markers include, but are not limited to, one or more of the previously discussed energy biomarkers, such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+H$^+$) or NADPH (NADPH+H$^+$) levels; NAD or NADP levels; ATP levels; anaerobic threshold; reduced coenzyme Q (CoQ$^{red}$) levels; oxidized coenzyme Q (CoQ$^{ox}$) levels; total coenzyme Q (CoQ$^{tot}$) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment of the invention, the level of one or more energy biomarkers in a patient suffering from a mitochondrial disease, such as Friedreich's ataxia, Leber's hereditary optic neuropathy, MELAS, or KSS, is improved to within two standard deviations of the average level in a healthy subject. In another embodiment of the invention, the level of one or more of these energy biomarkers in a patient suffering from a mitochondrial disease, such as Friedreich's ataxia, Leber's hereditary optic neuropathy, MELAS, or KSS is improved to within one standard deviation of the average level in a healthy subject. Exercise intolerance can also be used as an indicator of the efficacy of a given therapy, where an improvement in exercise tolerance (i.e., a decrease in exercise intolerance) indicates efficacy of a given therapy.

Several metabolic biomarkers have already been used to evaluate efficacy of CoQ10, and these metabolic biomarkers can be monitored as energy biomarkers for use in the methods of the current invention. Pyruvate, a product of the anaerobic metabolism of glucose, is removed by reduction to lactic acid in an anaerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7):695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)) and toxic mitochondrial myopathies (Chariot et al., Arthritis Rheum. 37(4): 583-6 (1994)). Changes in the redox state of liver mitochondria can be investigated by measuring the arterial ketone body ratio (acetoacetate/3-hydroxybutyrate: AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2):287-91 (1997); Honda et al., Leuk. Res. 24(6):461-8 (2000); Pilger et al., Free Radic. Res. 35(3):273-80 (2001); Kim et al. Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., Neurology 62(8):1297-302 (2004)). Phosphorous MRS (31P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242(7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V O2 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol.

51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic acid (lactate) levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of $NADH+H^+$, $NADPH+H^+$, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio). NAD, NADP, NADH and NADPH levels: Measurement of NAD, NADP, NADH ($NADH+H^+$) or NADPH ($NADPH+H^+$) can be measured by a variety of fluorescent, enzymatic, or electrochemical techniques, e.g., the electrochemical assay described in US 2005/0067303.

Oxygen consumption ($vO_2$ or VO2), carbon dioxide output ($vCO_2$ or VCO2), and respiratory quotient (VCO2/VO2): $vO_2$ is usually measured either while resting (resting $vO_2$) or at maximal exercise intensity ($vO_2$ max). Optimally, both values will be measured. However, for severely disabled patients, measurement of $vO_2$ max may be impractical. Measurement of both forms of $vO_2$ is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, reduced Cytochrome C, and ratio of oxidized Cytochrome C to reduced Cytochrome C: Cytochrome C parameters, such as oxidized cytochrome C levels (Cyt $C_{ox}$), reduced cytochrome C levels (Cyt $C_{red}$), and the ratio of oxidized cytochrome C/reduced cytochrome C ratio (Cyt $C_{ox}$/(Cyt $C_{red}$), can be measured by in vivo near infrared spectroscopy. See, e.g., Rolfe, P., "In vivo near-infrared spectroscopy," Annu. Rev. Biomed. Eng. 2:715-54 (2000) and Strangman et al., "Non-invasive neuroimaging using near-infrared light" Biol. Psychiatry 52:679-93 (2002).

Exercise tolerance/Exercise intolerance: Exercise intolerance is defined as "the reduced ability to perform activities that involve dynamic movement of large skeletal muscles because of symptoms of dyspnea or fatigue" (Piña et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q ($CoQ^{red}$) levels, oxidized coenzyme Q ($CoQ^{ox}$) levels, total coenzyme Q ($CoQ^{tot}$) levels, oxidized cytochrome C levels, reduced cytochrome C levels, oxidized cytochrome C/reduced cytochrome C ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to evaluate efficacy of the compounds and methods of the invention. (For the purposes of the invention, modulation, normalization, or enhancement of energy biomarkers includes modulation, normalization, or enhancement of anaerobic threshold.)

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods of the invention. RQ=respiratory quotient; BMR=basal metabolic rate; HR(CO)=heart rate (cardiac output); T=body temperature (preferably measured as core temperature); AT=anaerobic threshold; pH=blood pH (venous and/or arterial).

TABLE 1

| Site of Dysfunction | Biochemical Event | Measurable Energy Biomarker | Physical Effect |
| --- | --- | --- | --- |
| Respiratory Chain | ↑ NADH | Δ lactate, Δ lactate:pyruvate ratio; and Δ acetoacetate:β-hydroxy butyrate ratio | Metabolic dyscrasia & fatigue |

TABLE 1-continued

| Site of Dysfunction | Biochemical Event | Measurable Energy Biomarker | Physical Effect |
|---|---|---|---|
| Respiratory Chain | ↓ H$^+$ gradient | Δ ATP | Organ dependent dysfunction |
| Respiratory Chain | ↓ Electron flux | Δ VO$_2$, RQ, BMR, ΔT, AT, pH | Metabolic dyscrasia & fatigue |
| Mitochondria & cytosol | ↓ ATP, ↓ VO$_2$ | Δ Work, ΔHR (CO) | Exercise intolerance |
| Mitochondria & cytosol | ↓ ATP | Δ PCr | Exercise intolerance |
| Respiratory Chain | ↓ Cyt C$_{Ox/Red}$ | Δ λ ~700-900 nM (Near Infrared Spectroscopy) | Exercise intolerance |
| Intermediary metabolism | ↓ Catabolism | Δ C$^{14}$-Labeled substrates | Metabolic dyscrasia & fatigue |
| Respiratory Chain | ↓ Electron flux | Δ Mixed Venous VO$_2$ | Metabolic dyscrasia & fatigue |
| Mitochondria & cytosol | ↑ Oxidative stress | Δ Tocopherol & Tocotrienols, CoQ10, docosahexanoic acid | Uncertain |
| Mitochondria & cytosol | ↑ Oxidative stress | Δ Glutathione$_{red}$ | Uncertain |
| Mitochondria & cytosol | Nucleic acid oxidation | Δ8-hydroxy 2-deoxy guanosine | Uncertain |
| Mitochondria & cytosol | Lipid oxidation | ΔIsoprostane(s), eicasanoids | Uncertain |
| Cell membranes | Lipid oxidation | ΔEthane (breath) | Uncertain |
| Cell membranes | Lipid oxidation | ΔMalondialdehyde | Uncertain |

Treatment of a subject afflicted by a mitochondrial disease in accordance with the methods of the invention may result in the inducement of a reduction or alleviation of symptoms in the subject, e.g., to halt the further progression of the disorder.

Partial or complete suppression of the mitochondrial disease can result in a lessening of the severity of one or more of the symptoms that the subject would otherwise experience. For example, partial suppression of MELAS could result in reduction in the number of stroke-like or seizure episodes suffered.

Any one, or any combination of, the energy biomarkers described herein provide conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

Use of Compounds for Modulation of Energy Biomarkers

In addition to monitoring energy biomarkers to assess the status of treatment or suppression of mitochondrial diseases, the compounds of the invention can be used in subjects or patients to modulate one or more energy biomarkers. Modulation of energy biomarkers can be done to normalize energy biomarkers in a subject, or to enhance energy biomarkers in a subject.

Normalization of one or more energy biomarkers is defined as either restoring the level of one or more such energy biomarkers to normal or near-normal levels in a subject whose levels of one or more energy biomarkers show pathological differences from normal levels (i.e., levels in a healthy subject), or to change the levels of one or more energy biomarkers to alleviate pathological symptoms in a subject. Depending on the nature of the energy biomarker, such levels may show measured values either above or below a normal value. For example, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of energy biomarkers can involve restoring the level of energy biomarkers to within about at least two standard deviations of normal in a subject, more preferably to within about at least one standard deviation of normal in a subject, to within about at least one-half standard deviation of normal, or to within about at least one-quarter standard deviation of normal.

When an increase in an energy biomarker level is desired to normalize the one or more such energy biomarker, the level of the energy biomarker can be increased to within about at least two standard deviations of normal in a subject, more preferably increased to within about at least one standard deviation of normal in a subject, increased to within about at least one-half standard deviation of normal, or increased to within about at least one-quarter standard deviation of normal, by administration of one or more compounds according to the invention. Alternatively, the level of one or more of the energy biomarkers can be increased by about at least 10% above the subject's level of the respective one or more energy biomarkers before administration, by about at least 20% above the subject's level of the respective one or more energy biomarkers before administration, by about at least 30% above the subject's level of the respective one or more energy biomarkers before administration, by about at least 40% above the subject's level of the respective one or more energy biomarkers before administration, by about at least 50% above the subject's level of the respective one or more energy biomarkers before administration, by about at least 75% above the subject's level of the respective one or more energy biomarkers before administration, or by about at least 100% above the subject's level of the respective one or more energy biomarkers before administration.

When a decrease in a level of one or more energy biomarkers is desired to normalize the one or more energy biomarkers, the level of the one or more energy biomarkers can be decreased to a level within about at least two standard deviations of normal in a subject, more preferably decreased to within about at least one standard deviation of normal in a subject, decreased to within about at least one-half standard deviation of normal, or decreased to within about at least one-quarter standard deviation of normal, by administration of one or more compounds according to the invention. Alternatively, the level of the one or more energy biomarkers can be decreased by about at least 10% below the subject's level of the respective one or more energy biomarkers before administration, by about at least 20% below the subject's level of the respective one or more energy biomarkers before administration, by about at least 30% below the subject's level of the respective one or more energy biomarkers before administration, by about at least 40% below the subject's level of the respective one or more energy biomarkers before administration, by about at least 50% below the subject's level the respective one or more energy biomarkers before administration, by about at least 75% below the subject's level of the respective one or more energy biomarkers before administration, or by about at least 90% below the subject's level of the respective one or more energy biomarkers before administration.

Enhancement of the level of one or more energy biomarkers is defined as changing the extant levels of one or more energy biomarkers in a subject to a level which provides beneficial or desired effects for the subject. For example, a person undergoing strenuous effort or prolonged vigorous physical activity, such as mountain climbing, could benefit from increased ATP levels or decreased lactate levels. As described above, normalization of energy biomarkers may not achieve the optimum state for a subject with a mitochondrial disease, and such subjects can also benefit from enhancement of energy biomarkers. Examples of subjects who could benefit from enhanced levels of one or more energy biomarkers include, but are not limited to, subjects undergoing strenuous or prolonged physical activity, subjects with chronic energy problems, or subjects with chronic respiratory problems. Such subjects include, but are not limited to, pregnant females, particularly pregnant females in labor; neonates, particularly premature neonates; subjects exposed to extreme environments, such as hot environments (temperatures routinely exceeding about 85-86 degrees Fahrenheit or about 30 degrees Celsius for about 4 hours daily or more), cold environments (temperatures routinely below about 32 degrees Fahrenheit or about 0 degrees Celsius for about 4 hours daily or more), or environments with lower-than-average oxygen content, higher-than-average carbon dioxide content, or higher-than-average levels of air pollution (airline travelers, flight attendants, subjects at elevated altitudes, subjects living in cities with lower-than-average air quality, subjects working in enclosed environments where air quality is degraded); subjects with lung diseases or lower-than-average lung capacity, such as tubercular patients, lung cancer patients, emphysema patients, and cystic fibrosis-patients; subjects recovering from surgery or illness; elderly subjects, including elderly subjects experiencing decreased energy; subjects suffering from chronic fatigue, including chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

Accordingly, when an increase in a level of one or more energy biomarkers is beneficial to a subject, enhancement of the one or more energy biomarkers can involve increasing the level of the respective energy biomarker or energy biomarkers to about at least one-quarter standard deviation above normal, about at least one-half standard deviation above normal, about at least one standard deviation above normal, or about at least two standard deviations above normal. Alternatively, the level of the one or more energy biomarkers can be increased by about at least 10% above the subject's level of the respective one or more energy biomarkers before enhancement, by about at least 20% above the subject's level of the respective one or more energy biomarkers before enhancement, by about at least 30% above the subject's level of the respective one or more energy biomarkers before enhancement, by about at least 40% above the subject's level of the respective one or more energy biomarkers before enhancement, by about at least 50% above the subject's level of the respective one or more energy biomarkers before enhancement, by about at least 75% above the subject's level of the respective one or more energy biomarkers before enhancement, or by about at least 100% above the subject's level of the respective one or more energy biomarkers before enhancement.

When a decrease in a level of one or more energy biomarkers is desired to enhance one or more energy biomarkers, the level of the one or more energy biomarkers can be decreased by an amount of about at least one-quarter standard deviation of normal in a subject, decreased by about at least one-half standard deviation of normal in a subject, decreased by about at least one standard deviation of normal in a subject, or decreased by about at least two standard deviations of normal in a subject. Alternatively, the level of the one or more energy biomarkers can be decreased by about at least 10% below the subject's level of the respective one or more energy biomarkers before enhancement, by about at least 20% below the subject's level of the respective one or more energy biomarkers before enhancement, by about at least 30% below the subject's level of the respective one or more energy biomarkers before enhancement, by about at least 40% below the subject's level of the respective one or more energy biomarkers before enhancement, by about at least 50% below the subject's level of the respective one or more energy biomarkers before enhancement, by about at least 75% below the subject's level of the respective one or more energy biomarkers before enhancement, or by about at least 90% below the subject's level of the respective one or more energy biomarkers before enhancement.

Use of Compounds in Research Applications, Experimental Systems, and Assays

The compounds of the invention can also be used in research applications. For example, alpha-tocopherol quinone can be used in vitro, in vivo, or ex vivo experiments to modulate one or more energy biomarkers in an experimental system. Such experimental systems can be cell samples, tissue samples, cell components or mixtures of cell components, partial organs, whole organs, or organisms. Any one or more of the compounds of formula I, Ia, Ib, II, IIa, IIb, III, IIIa, IIIb, IV, IVa, IVb, V, Va, Vb, VI, VIa, VIb, VII-O, VII-R, VIII-O, VIII-R, IX-O, IX-R, X-O, X-R, XI-O, XI-R, XII-O, and/or XII-R can be used in experimental systems or research applications. Such research applications can include, but are not limited to, use as assay reagents, elucidation of biochemical pathways, or evaluation of the effects of other agents on the metabolic state of the experimental system in the presence/absence of one or more compounds of the invention.

Additionally, the compounds of the invention can be used in biochemical tests or assays. Such tests can include incubation of one or more compounds of the invention with a tissue or cell sample from a subject to evaluate a subject's potential response (or the response of a specific subset of subjects) to administration of said one or more compounds, or to determine which compound of the invention produces the optimum effect in a specific subject or subset of subjects. One such test or assay would involve 1) obtaining a cell sample or tissue sample from a subject in which modulation of one or more energy biomarkers can be assayed; 2) administering one or more compounds of the invention to the cell sample or tissue sample; and 3) determining the amount of modulation of the one or more energy biomarkers after administration of the one or more compounds, compared to the status of the energy biomarker prior to administration of the one or more compounds. Another such test or assay would involve 1) obtaining a cell sample or tissue sample from a subject in which modulation of one or more energy biomarkers can be assayed; 2) administering at least two compounds of the invention to the cell sample or tissue sample; 3) determining the amount of modulation of the one or more energy biomarkers after administration of the at least two compounds, compared to the status of the energy biomarker prior to administration of the at least compounds, and 4) selecting a compound for use in treatment, suppression, or modulation based on the amount of modulation determined in step 3).

Pharmaceutical Formulations

The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly (phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

The invention also provides articles of manufacture and kits containing materials useful for treating or suppressing mitochondrial diseases. The article of manufacture comprises a container with a label. Suitable containers include, for example, bottles, vials, and test tubes. The containers may be formed from a variety of materials such as glass or plastic. The container holds a composition having an active agent which is effective for treating or suppressing mitochondrial diseases. The active agent in the composition is one or more of the compounds of formulas I, Ia, Ib, II, IIa, II, III, IIIa, IIIb, IV, IVa, IVb, V, Va, Vb, VI, VIa, VIb, VII-O, VII-R, VIII-O, VIII-R, IX-O, IX-R, X-O, X-R, XI-O, XI-R, XII-O, and/or XII-R. The label on the container indicates that the composition is used for treating or suppressing mitochondrial diseases, and may also indicate directions for either in vivo or in vitro use, such as those described above.

The invention also provides kits comprising any one or more of the compounds of formulas I, Ia, Ib, II, IIa, IIb, III, IIIa, IIIb, IV, IVa, IVb, V, Va, Vb, VI, VIa, VIb, VII-O, VII-R, VIII-O, VIII-R, IX-O, IX-R, X-O, X-R, XI-O, XI-R, XII-O, and/or XII-R. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, to treat an individual with a mitochondrial disorder, or to suppress a mitochondrial disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are an effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds of the present invention may be administered in a single daily dose, or the total daily dosage may be administered in divided dosage of two, three or four times daily.

α-tocopherol quinone is a naturally-occurring substance, which is normally found in serum (Pollok et al., J. Chromatogr. A. 1056:257 (2004)) and mitochondrial membranes (Gregor et al., Biochem Pharmacol. 71:1589 (2006)). Accordingly, when α-tocopherol quinone is administered to treat or suppress mitochondrial diseases or to modulate energy biomarkers, it can be administered in an amount sufficient to raise serum levels, intracellular levels, or mitochondrial membrane levels of α-tocopherol quinone by at least about 10%, by at least about 25%, by at least about 50%, by at least about 75%, by at least about 100%, by at least about 150%, or by at least about 200% as compared to the level of α-tocopherol quinone prior to α-tocopherol quinone administration. Reduced α-tocopherol quinone also occurs naturally. Accordingly, when α-tocopherol quinone is administered to treat or suppress mitochondrial diseases or to modulate energy biomarkers, it can be administered in an amount sufficient to raise serum levels, intracellular levels, or mitochondrial membrane levels of its reduced counterpart, reduced α-tocopherol quinone, by at least about 10%, by at least about 25%, by at least about 50%, by at least about 75%, by at least about 100%, by at least about 150%, or by at least about 200% as compared to the level of reduced α-tocopherol quinone prior to α-tocopherol quinone administration. Alternatively, reduced α-tocopherol quinone can be administered instead of α-tocopherol quinone in order to treat or suppress mitochondrial diseases or to modulate energy biomarkers, and can be administered in an amount sufficient to raise serum levels, intracellular levels, or mitochondrial membrane levels of reduced α-tocopherol quinone by at least about 10%, by at least about 25%, by at least about 50%, by at least about 75%, by at least about 100%, by at least about 150%, or by at least about 200% as compared to the level of reduced α-tocopherol quinone prior to reduced α-tocopherol quinone administration While the compounds of the invention can be administered as the sole active pharmaceutical agent, they can also be used in combination with one or more other agents used in the treatment or suppression of disorders. Representative agents useful in combination with the compounds of the invention for the treatment or suppression of mitochondrial diseases include, but are not limited to, Coenzyme Q, vitamin E, idebenone, MitoQ, vitamins, and antioxidant compounds.

When additional active agents are used in combination with the compounds of the present invention, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

The invention will be further understood by the following nonlimiting examples.

EXAMPLES

Example 1

Synthesis of Compounds

Example 1A

Synthesis of mixture of stereoisomers of Compound VIII-i (R/S,R,R)-2,3,5-trimethyl-6-(3,7,11,15-tetramethyl-hexadecyl)-[1,4]benzoquinone

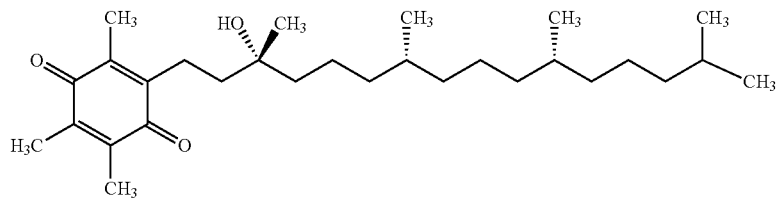

Ex-1A-1

1) POCl₃, pyr.
2) H₂, PtO₂

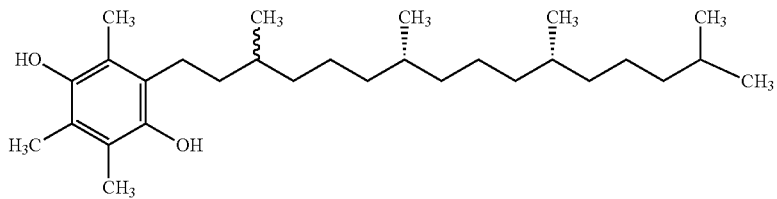

Ex-1A-2

O₂, SiO₂, DCM

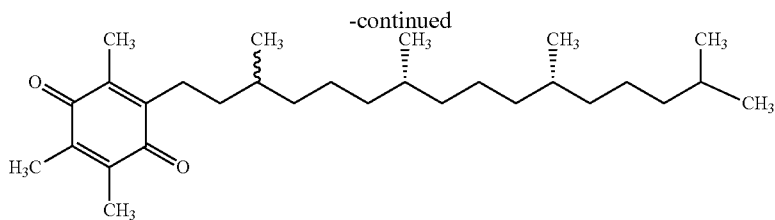

Ex-1A-3; VIII-i (mix. of stereoisomers)

Step 1: A 50 mL RBF was charged with (R,R,R)-2-(3-hydroxy-3,7,11,15-tetramethyl-hexadecyl)-3,5,6-trimethyl-[1,4]benzoquinone (Ex-1A-1) (2.0 g, 4.40 mmol) and pyridine (10 mL) and the reaction was cooled to 0 C. Neat POCl$_3$ (520 L, 5.60 mml) was added. The reaction was allowed to warm to RT and stirred for 16 h. The reaction was monitored by TLC (3:1 Heptane.:ETOAc). The reaction was diluted with saturated NH$_4$Cl (10 mL) and MTBE (10 mL) and then extracted with MTBE (3×10 mL). The combined MTBE layers were passed through a silica plug and then washed with 0.1HCl (3×10 mL). The MTBE layer was then concentrated by rotary evaporation to yield a yellow oil (1.95 g, 100%). The crude material, which was a mixture of alkene regioisomers and geometric isomers, was taken to the next step without further purification.

Step 2: A crude mixture of alkene regioisomers and geometric isomers (13.3 g, 31.0 mmol, prepared as described in step 1) was dissolved in EtOAc (100 mL) and hydrogenated using PtO$_2$ (250 mg) at 50 psi H$_2$. After 6 h, ~30% unsaturated material remained ($^1$H NMR). Additional PtO$_2$ (250 mg) was added and hydrogenation was continued for 16 h. The reaction mixture was filtered through celite, which was then rinsed with EtOAc (50 mL). The filtrate was concentrated by rotary evaporation to yield (R/S,R,R)-2,3,5-trimethyl-6-(3,7,11,15-tetramethyl-hexadecyl)-benzene-1,4-diol (Ex-1A-2) as a waxy white solid (12.7 g, 95%). $^1$H NMR (400 MHz, CDCl$_3$) δ (ppm): 4.36 (broad-s, 1H), 4.33 (broad-s, 1H), 2.70-2.54 (m, 2H), 2.20 (s, 3H), 2.18 (s, 6H), 1.57-1.04 (m, 24H), 1.00 (d, J=6.4 Hz, 3H), 0.89-0.86 (m, 12H).

Step 3: A solution of (R/S,R,R)-2,3,5-trimethyl-6-(3,7,11,15-tetramethyl-hexadecyl)-benzene-1,4-diol (Ex-1A-2) (10.2 g, 0.24 g) in DCM (100 mL) was allowed to stir in the presence of SiO$_2$ (500 mg) for 4 days exposed to air. The reaction mixture was then filtered and concentrated by rotary evaporation to yield an orange oil (10.0 g, 98%). A portion of the crude product (5.0 g) was purified using a Biotage automated chromatography instrument (eluted with DCM: Hept gradient) to yield pure (R/S,R,R)-2,3,5-trimethyl-6-(3,7,11,15-tetramethyl-hexadecyl)-[1,4]benzoquinone (Ex-1A-3, mixture of stereoisomers of compound VIII-i) (1.98 g, 40%). $^1$H NMR (400 MHz, CDCl$_3$) δ (ppm): 2.54-2.40 (m, 2H), 2.03 (s, 3H), 2.03 (s, 6H), 1.56-1.02 (m, 24H), 0.96 (d, J=6.5 Hz, 3H), 0.89-0.85 (m, 12H).

Example 1B

Synthesis of Compound IX-1,2,3,5-Trimethyl-6-(3,7,11,15-tetramethyl-hexadeca-2,6,10,14-tetraenyl)-[1,4]-benzoquinone

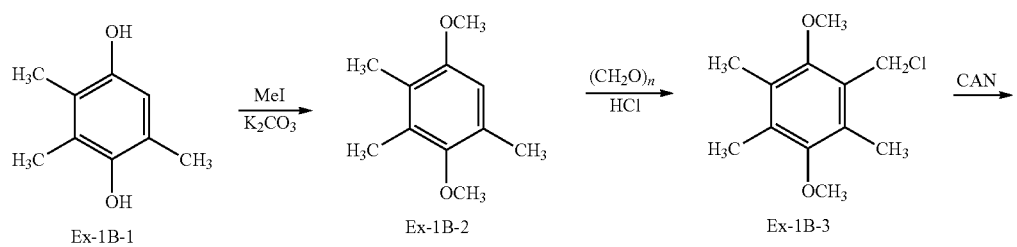

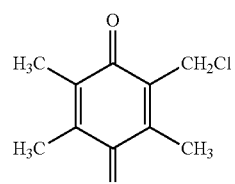

Ex-1B-4

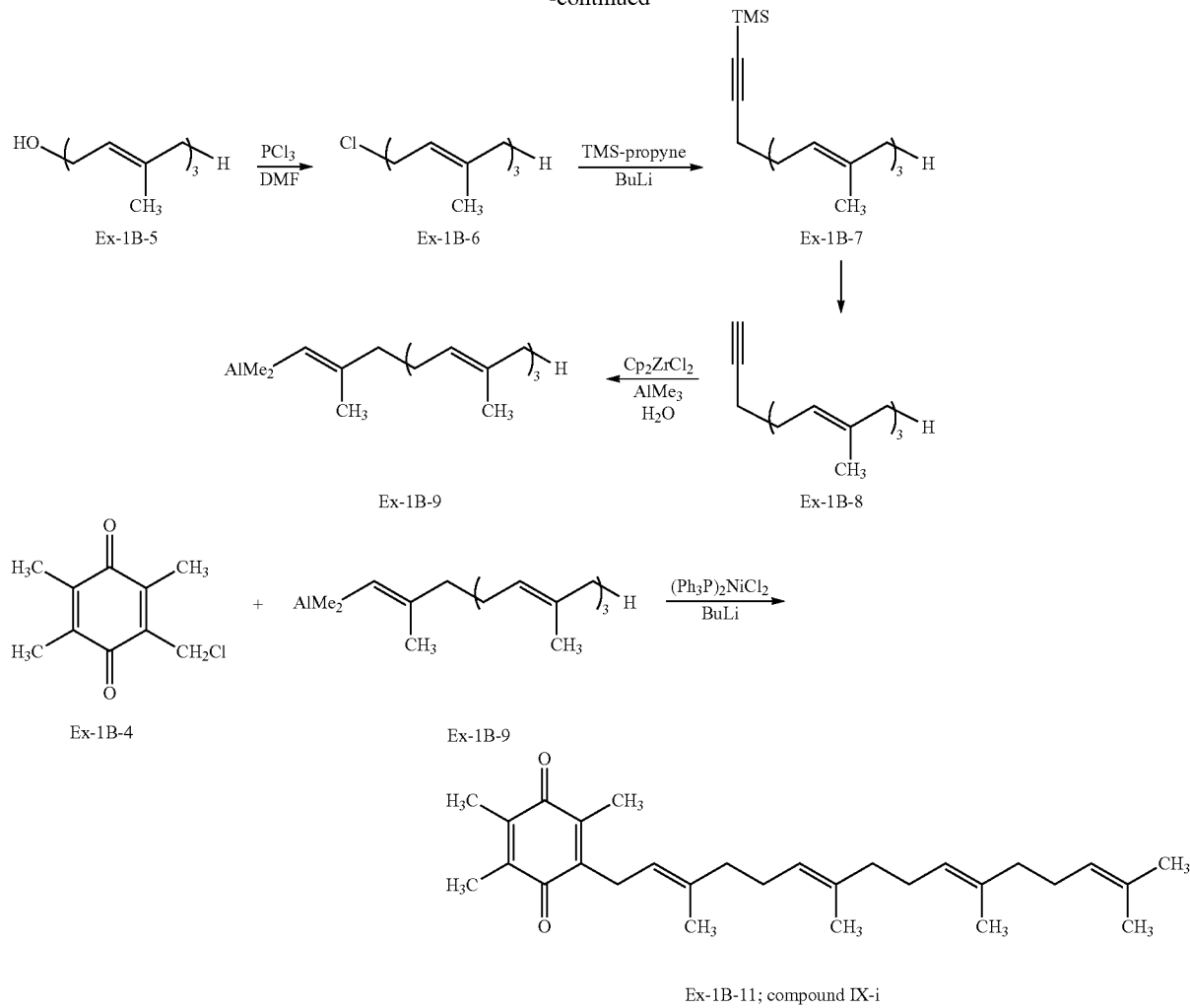

Ex-1B-11; compound IX-i

Step 1: A 2 L 3-N flask was charged with 2,3,5-trimethyl-benzene-1,4-diol (Ex-1B-1) (50 g, 0.33 mol) and MEK (750 mL) to yield an amber solution. Potassium carbonate (210 g, 1.64 mol) was charged to the solution. After 30 min at RT, MeI (81.2 mL, 1.31 mol) was added to the brown suspension. The reaction mixture was heated to 65° C. for 72 h. After cooling to RT, the reaction mixture was concentrated to dryness by rotary evaporation to give a white paste. The paste was washed with EtOAc (3×300 mL). The EtOAc extracts were combined and concentrated by rotary evaporation. The resulting yellow-brown oil was chromatographed (80:20/Heptanes:EtOAc) to yield 1,4-dimethoxy-2,3,5-trimethyl-benzene (Ex-1B-2) (47.2 g, 80%). $^1$H NMR (400 MHz, CDCl$_3$) δ (ppm): 6.55 (s, 1H), 3.80 (s, 3H), 3.68 (s, 3H), 2.30 (s, 3H), 2.22 (s, 3H), 2.14 (s, 3H).

Step 2: A flask was charged with 1,4-dimethoxy-2,3,5-trimethyl-benzene (Ex-1B-2) (47.2 g, 0.26 mol), glacial acetic acid (250 mL), and paraformaldehyde (39.3 g, 1.31 mol) to yield a yellow suspension. Anhydrous HCl gas was then slowly bubbled through the reaction mixture for 1.5 h producing a clear amber solution. The reaction mixture was then diluted with water (300 mL) and extracted with MTBE (3×300 mL). The combined MTBE layers were dried over Na$_2$SO$_4$, filtered and concentrated by rotary evaporation. Purification of the crude product by column chromatography (95:5/Heptanes:EtOAc) yielded 48.7 g of 1-chloromethyl-2,5-dimethoxy-3,4,6-trimethyl-benzene (Ex-1B-3) (81%). $^1$H NMR (400 MHz, CDCl$_3$) δ (ppm): 4.76 (s, 2H), 3.81 (s, 3H), 3.68 (s, 3H), 2.36 (s, 3H), 2.23 (s, 3H), 2.21 (s, 3H).

Step 3: A flask was charged with 1-chloromethyl-2,5-dimethoxy-3,4,6-trimethyl-benzene (Ex-1B-3) (6.37 g, 27.9 mmol) and ACN (10 mL) then cooled to 0° C. A solution of CAN (31.3 g, 57.1 mmol) in water (10 mL) was added to the flask. After 1 h the reaction mixture was extracted with MTBE (3×50 mL). The combined MTBE layers were then washed with water (50 mL), dried over MgSO$_4$, filtered and concentrated by rotary evaporation. Trituration of the crude product with MeOH yielded 4.49 g of 2-chloromethyl-3,5,6-trimethyl-[1,4]benzoquinone (Ex-1B-4) (81%) as a bright orange-yellow solid. $^1$H NMR (400 MHz, CDCl$_3$) δ (ppm): 4.77 (s, 2H), 2.17 (s, 3H), 2.07 (s, 3H), 2.06 (s, 3H).

Step 4: A 3-N 100 mL flask was charged with PCl$_3$ (2.8 mL, 31.6 mmol) and dry DMF (32 mL) then stirred at RT for 1 h. In a separate 50 mL flask, farnesol (Ex-1B-5) (10.0 g, 45.2 mmol) and DMF (10 mL) was charged. The PCl$_3$/DMF solution was then transferred to the farnesol, solution and the resulting dark orange solution was stirred for 1 h. The reaction was quenched by addition of solid NaHCO$_3$ (2.5 g, 63.2 mmol). The solvent was removed by high vacuum rotary evaporation to yield an oily orange residue. To the residue was added MTBE (40 mL) and water (40 mL). The aqueous phase was washed with MTBE (3×20 mL). The MTBE layers were combined, washed with brine (2×20 mL), dried over MgSO$_4$, filtered and finally concentrated by rotary evaporation to yield 1-chloro-3,7,11-trimethyl-dodeca-2,6,10-triene (Ex-1B-6) as a yellow oil (9.89 g, 92%). $^1$H NMR (400 MHz, CDCl$_3$) δ (ppm): 5.47 (broad-t, J=8.3 Hz, 1H), 5.15-5.07 (m, 2H), 4.12 (d, J=8.1 Hz, 2H), 2.18-1.95 (m, 8H), 1.75 (s, 3H), 1.70 (s, 3H), 1.62 (s, 6H).

Step 5: A 3-N 250 mL flask was inserted and charged with TMS-propyne (6.90 mL, 46.2 mmol) and THF (90 mL). The reaction was cooled to −40° C. after which time. BuLi (18.5 mL, 46.2 mmol) was added. After 45 min, the reaction was cooled further (−70° C.) and a precooled (−70° C.) solution of 1-chloro-3,7,11-trimethyl-dodeca-2,6,10-triene (Ex-1B-6) (8.9 g, 37.0 mmol) in THF (50 mL) was added over 10 min. After 1 h, the reaction was warmed to RT and quenched by addition of saturated NH$_4$Cl (20 mL) and MTBE (25 mL). The aqueous layer was separated and washed with MTBE (25 mL). The combined organic layers were then washed with brine, dried over MgSO$_4$, filtered and concentrated to yield a yellow liquid (10.3 g). The crude oil was further purified by column chromatography (99:1/Heptanes:MTBE) to provide trimethyl-(6,10,14-trimethyl-pentadeca-5,9,13-trien-1-ynyl)-silane (Ex-1B-7). $^1$H NMR (400 MHz, CDCl$_3$) δ (ppm): 5.22-5.16 (m, 1H), 5.16-5.08 (m, 2H), 2.27-2.22 (m, 4H), 2.15-1.94 (m, 8H), 1.70 (s, 3H), 1.65 (s, 3H), 1.62 (s, 6H), 0.17 (s, 9H).

Step 6: A 3-N 250 mL flask was charged with trimethyl-(6,10,14-trimethyl-pentadeca-5,9,13-trien-1-ynyl)-silane (Ex-1B-7) (19.38 g, 64.1 mmol) and NaOEt (42 mL of a 21% w/w solution, 112 mmol). The reaction mixture was stirred at 60° C. for 4 h. After cooling to RT, the reaction mixture was diluted with MTBE (100 mL) and water (100 mL) and then filtered to remove solid present at the phase interface. The aqueous layer was extracted with MTBE (3×100 mL). The combined MTBE layers were washed with brine (100 mL), dried over MgSO$_4$, filtered, and concentrated by rotary evaporation to yield 12.43 g of 6,10,14-trimethyl-pentadeca-5,9,13-trien-1-yne (Ex-1B-8) as a dark orange oil (96%). $^1$H NMR (400 MHz, CDCl$_3$) δ (ppm): 5.23-5.17 (m, 1H), 5.17-5.07 (m, 2H), 2.29-1.95 (m, 13H), 1.70 (s, 3H), 1.65 (s, 3H), 1.62 (s, 6H).

Step 7: A 3-N 250 mL flask equipped with a thermometer, a stirbar, and stopcock fitted vacuum adapter was evacuated, flame-dried, and flushed with N$_2$ (3×) via a single manifold Schlenk line. To the flask was then charged bis(cyclopentadienyl)zirconium dichloride (Cp$_2$ZrCl$_2$) (2.16 g, 7.4 mmol) and dry DCE (40 mL). The reaction mixture was cooled to −20° C. AlMe$_3$ (36.8 mL, 73.6 mmol) was added dropwise over 5 min to generate a yellow slurry. After 15 min. at −20° C., water (220 µL, 12.3 mmol) was added dropwise over 5 min. to yield a greenish-yellow solution. After stirring for 30 min. at −20° C., a solution of 6,10,14-trimethyl-pentadeca-5,9,13-trien-1-yne (Ex-1B-8) (6.0 g, 24.6 mmol) in dry DCE (20 mL) was added dropwise over 5 min. The reaction mixture became dark brown then amber in color. The reaction was allowed to warm to RT over 2 h. $^1$H NMR analysis of a DCl quenched aliquot revealed 95% deuterium incorporation. The solvent was removed in vacuo at RT. The resulting residue was washed with heptanes (2×40 mL) through a sintered glass frit into an inerted 250 mL 3-N flask equipped with a stirbar and stopcock fitted vacuum adapter. The reaction was allowed to stir overnight.

The solvent was removed in vacuo and replaced by addition of dry degassed THF (40 mL). A quenched aliquot of the reaction mixture revealed >92% deuterium incorporation by $^1$H NMR spectroscopy. A solution of 2-chloromethyl-3,5,6-trimethyl-[1,4]benzoquinone (Ex-1B-4) (3.0 g, 15.0 mmol) in dry degassed THF (20 mL) was added to the flask which was then cooled to 0° C. In a separate inerted 50 mL flask, (PPh$_3$)$_2$NiCl$_2$ (750 mg, 1.3 mmol) and dry degassed THF (20 mL) was charged. BuLi (1.4 mL, 2.6 mmol) was added to the brown Ni(II) suspension to generate a blood red solution. The solution was stirred for 5 min. then added to the vinylalane/quinone (Ex-1B-9/Ex-1B-4) solution. The amber solution became blue gray in color. After 5 min, the reaction was complete by $^1$H NMR analysis of a quenched aliquot.

The reaction was quenched by very slow addition of 1 M HCl (great caution must be used in this procedure, as it is extremely exothermic) such that the temperature did not exceed 15° C. The reaction mixture was diluted with MTBE (20 mL). The resulting suspension was filtered. The aqueous layer of the filtrate was washed with MTBE (3×25 mL). The combined MTBE layers were dried over MgSO$_4$, filtered, and concentrated by rotary evaporation to yield an amber oil (12 g). Purification of the crude oil by column chromatography (heptane to 1:2/heptane:DCM) yielded pure 2,3,5-trimethyl-6-(3,7,11,15-tetramethyl-hexadeca-2,6,10,14-tetraenyl)-[1,4]benzoquinone (Ex-1B-11, or Compound IX-i) (5.25 g, 83%, >96% a/a by HPLC). $^1$H NMR (400 MHz, CDCl$_3$) δ (ppm): 5.11-5.05 (m, 3H), 4.98-4.95 (m, 1H), 3.21 (d, J=6.9 Hz, 2H), 2.10-1.94 (m, 21H), 1.76 (s, 3H), 1.69 (s, 3H), 1.61 (s, 3H), 1.60 (s, 3H), 1.59 (s, 3H).

Example 1C (R,R,R)-2-butyl-3-(3-hydroxy-3,7,11,15-tetramethyl-hexadecyl)-5,6-dimethyl-[1,4]benzoquinone

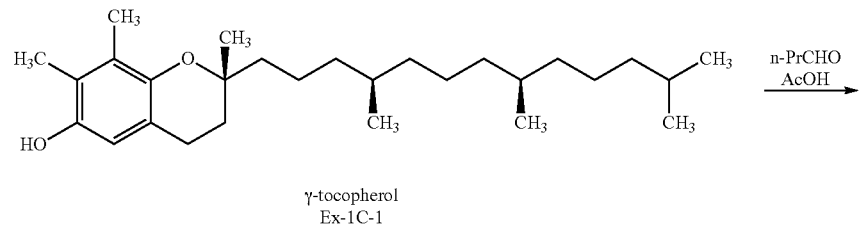

γ-tocopherol
Ex-1C-1

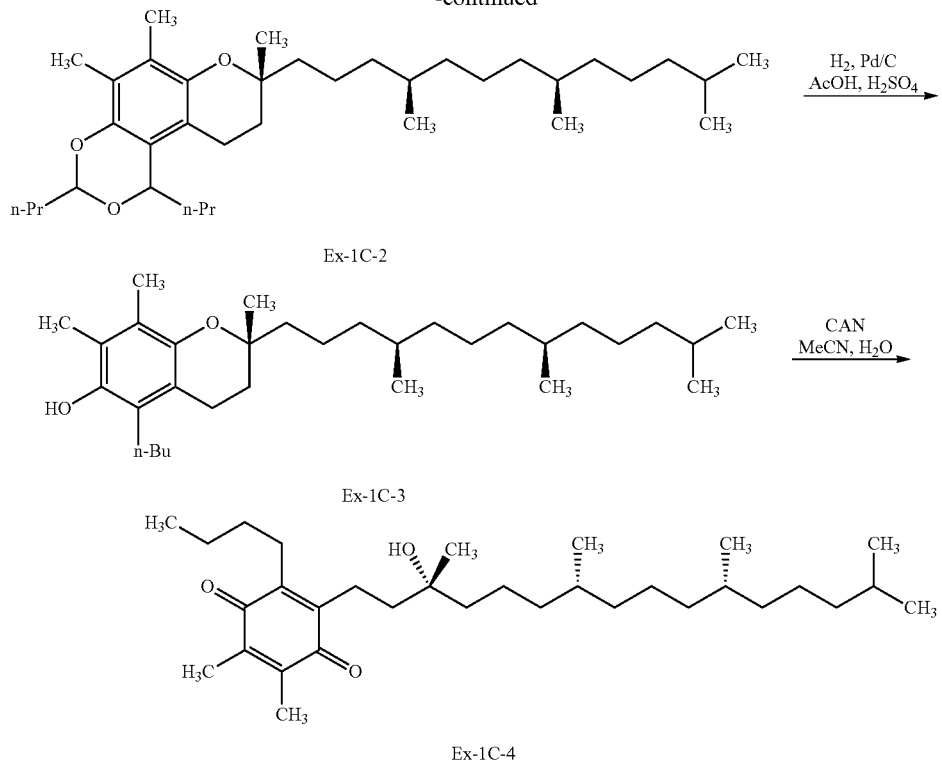

Ex-1C-2

Ex-1C-3

Ex-1C-4

Step 1: A 25 mL RBF was charged with butyraldehyde (155 mg, 2.16 mmol), AcOH (2 mL) and H₂SO₄ (1 drop). To the flask was then added a solution of (+)-γ-tocopherol (Ex-1C-1) (300 mg, 0.72 mmol) in AcOH (3 mL) dropwise over 2 h via syringe pump. The reaction was then stirred for 16 h and monitored by TLC (9:1 Hept:EtOAc). The reaction was then diluted with water (15 mL) and extracted with DCM (3×20 mL). The combined organic layers were washed with water (3×15 mL), dried over Na₂SO₄, filtered and concentrated by rotary evaporation to yield 7,9,10-trimethyl-2,4-dipropyl-7-(4,8,12-trimethyl-tridecyl)-4,5,6,7-tetrahydro-1,3,8-trioxa-phenanthrene (Ex-1C-2) as a brownish oil (425 mg, >100%), which was used without further purification.

Step 2: A solution of 7,9,10-trimethyl-2,4-dipropyl-7-(4,8,12-trimethyl-tridecyl)-4,5,6,7-tetrahydro-1,3,8-trioxa-phenanthrene (Ex-1C-2) (180 mg of crude material form above) in AcOH (10 mL) and conc. H₂SO₄ (10 drops) was hydrogenated (H₂, 50 psi, RT) with 5% Pd/C (20 mg of 50% w/w wet) at RT for 16 h. The reaction mixture was then filtered through celite. The celite was rinsed with DCM (2×2 mL). The DCM layer was concentrated by rotary evaporation to yield a light brown oil. The oil was dissolved in DCM (15 mL) and passed through a silica plug. The DCM was concentrated by rotary evaporation to yield (R,R,R)-5-butyl-2,7,8-trimethyl-2-(4,8,12-trimethyl-tridecyl)-chroman-6-ol (Ex-1C-3) as a cloudy yellow oil (165 mg, >100%), which was used directly without further purification.

Step 3: A 50 mL RBF flask was charged with (R,R,R)-5-butyl-2,7,8-trimethyl-2-(4,8,12-trimethyl-tridecyl)-chroman-6-ol (Ex-1C-3) (120 mg, 0.25 mmol) and ACN (25 mL), then cooled to 0° C. A solution of CAN (268 mg, 0.49 mmol) in water (1 mL) was added dropwise over 1 min to the reaction resulting in a bright orange solution. After 10 min, the reaction was deemed complete (TLC-9:1 hept: EtOAc). The reaction was diluted with DCM (10 mL) and water (10 mL). The aqueous layer was washed with DCM (10 mL). The DCM layers were washed with brine (5 mL), passed through a silica plug and concentrated by rotary evaporation to yield (R,R,R)-2-butyl-3-(3-hydroxy-3,7,11,15-tetramethyl-hexadecyl)-5,6-dimethyl-[1,4]benzoquinone (Ex-1C-4) as an orange oil (105 mg, 85%). ¹H NMR (400 MHz, CDCl₃) δ (ppm): 2.56-2.52 (m, 2H), 2.47 (broad-t, J=6.9 Hz, 2H), 2.02 (s, 6H), 1.55-1.02 (m, 28 μl), 0.95 (broad-t, J=5.6 Hz, 3H), 0.89-0.85 (m, 15H).

Example 1D (R,R,R)-2-(3-hydroxy-3,7,11,15-tetramethyl-hexadecyl)-5,6-dimethyl-3-propyl-[1,4]benzoquinone

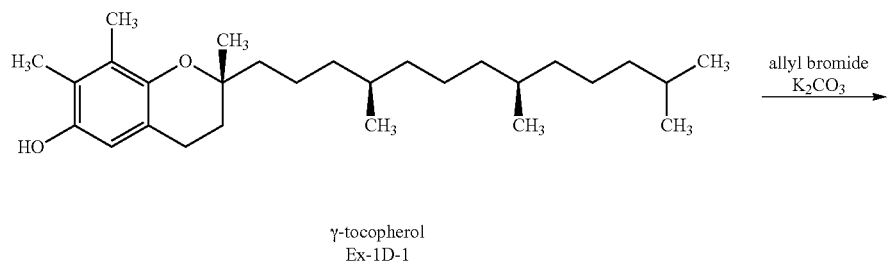

γ-tocopherol
Ex-1D-1

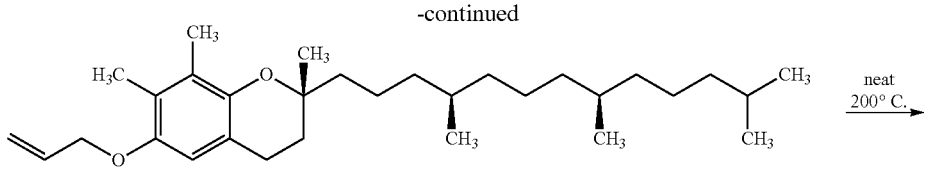

Ex-1D-2

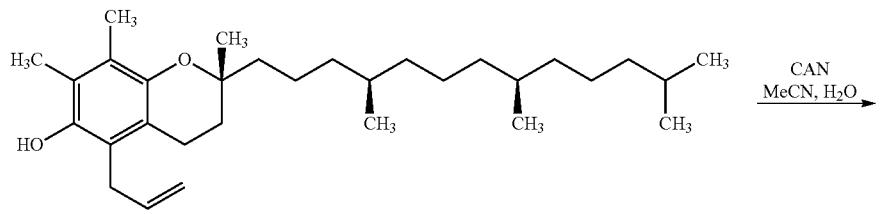

Ex-1D-3

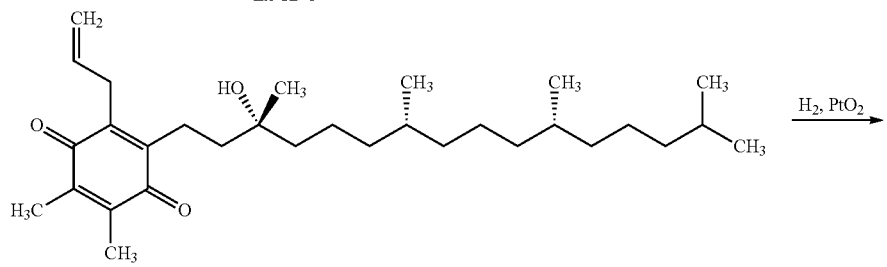

Ex-1D-4

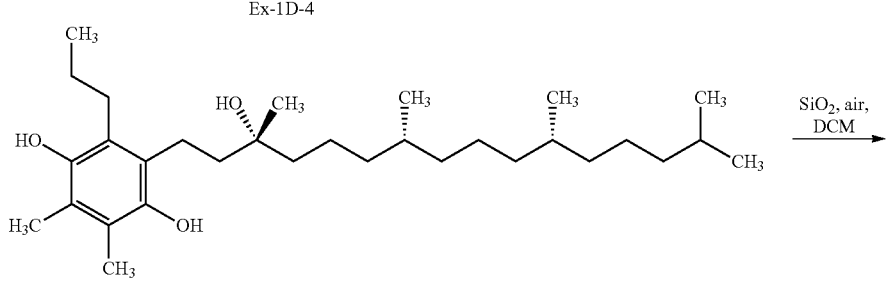

Ex-1D-5

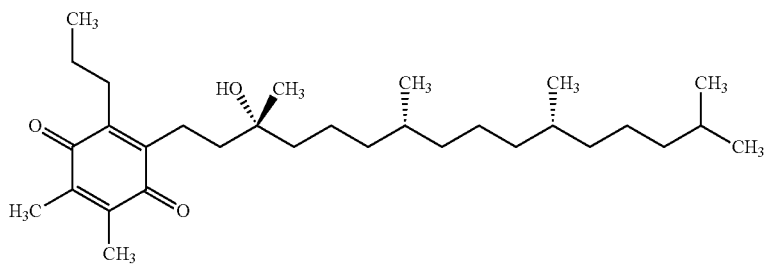

Ex-1D-6

Step 1: (+)-γ-tocopherol (Ex-1D-1) (300 mg, 0.72 mmol), K₂CO₃ (199 mg, 1.44 mmol), allyl bromide (182 µL, 1.44 mmol) and acetone (8 mL) were charged to a 50 mL RBF. The reaction was heated to reflux for 20 h after which time it was deemed complete by TLC (1:5 EtOAc:Hept). The reaction was diluted with water (10 mL). The aqueous layer was separated and washed with DCM (3×10 mL). The combined DCM layers were dried over Na₂SO₄, filtered and concentrated by rotary evaporation to yield a pale yellow oil. The oil was flashed through a silica plug (1:1: DCM: Heptane). After concentration of the eluent, (R,R,R)-6-allyloxy-2,7,8-trimethyl-2-(4,8,12-trimethyl-tridecyl)-chroman (Ex-1D-2) was obtained as a clear, colorless oil (334 mg, >100%), which was used without further purification.

Step 2: (R,R,R)-6-allyloxy-2,7,8-trimethyl-2-(4,8,12-trimethyl-tridecyl)-chroman (Ex-1D-2) (0.33 g, 0.72 mmol) was heated to 200° C. for 1 h after which time the reaction was deemed complete (TLC). The reaction was then cooled to RT and purified by flash chromatography (1:1 DCM: Heptane) to yield rearranged product (R,R,R)-5-allyl-2,7,8- trimethyl-2-(4,8,12-trimethyl-tridecyl)-chroman-6-ol (Ex-1D-3) (112 mg, 34%), which was used without further purification.

Step 3: A 50 mL RBF flask was charged with (R,R,R)-5-allyl-2,7,8-trimethyl-2-(4,8,12-trimethyl-tridecyl)-chroman-6-ol (Ex-1D-3) (120 mg, 0.26 mmol) and ACN (20 mL), then cooled to 0° C. A solution of CAN (285 mg, 0.52 mmol) in water (1 mL) was added dropwise over 1 min to the reaction resulting in a bright orange solution. After 15 min, the reaction was deemed complete (TLC-9:1 hept:EtOAc). The reaction was diluted with MTBE (10 mL) and water (10 mL). The aqueous layer was washed with MTBE (3×10 mL). The combined; MTBE layers were washed with brine (5 mL), dried over MgSO$_4$, filtered and concentrated by rotary evaporation to yield an orange oil. The oil was dissolved in DCM (10 mL) and passed through a silica plug. The DCM eluent was concentrated by rotary evaporation to yield (R,R,R)-2-allyl-3-(3-hydroxy-3,7,11,15-tetramethyl-hexadecyl)-5,6-dimethyl-[1,4]benzoquinone (Ex-1D-4) as an orange oil (100 mg, 80%). $^1$H NMR (400 MHz, CDCl$_3$) δ (ppm): 5.83 (ddt, 1H), 5.10-5.05 (m, 2H), 3.29 (d, J=6.2 Hz, 2H), 2.59-2.45 (m, 2H), 2.04 (s, 6H), 1.56-1.00 (m, 24H), 1.25 (s, 3H), 0.89-0.85 (m, 12H).

Step 4: (R,R,R)-2-allyl-3-(3-hydroxy-3,7,11,15-tetramethyl-hexadecyl)-5,6-dimethyl-[1,4]benzoquinone (Ex-1D-4) (50 mg, 0.1 mmol) was hydrogenated using PtO$_2$ (5 mg) at 50 psi for 2 h in a solution of EtOAc (5 mL). The suspension was filtered through celite, which was rinsed with DCM (2×2 mL). The pale yellow solution was concentrated b rotary evaporation to yield a pale yellow oil (Ex-1D-5). The oil was dissolved in DCM (5 mL) and stirred with silica (~20 mg) for 5 days. The bright yellow suspension was filtered through a cotton plug and concentrated by rotary evaporation to yield (R,R,R)-2-(3-hydroxy-3,7,11,15-tetramethyl-hexadecyl)-5,6-dimethyl-3-propyl-[1,4]benzoquinone (Ex-1D-6) as a bright yellow oil (38 mg, 76%). $^1$H NMR (400 MHz, CDCl$_3$) δ (ppm): 2.57-2.52 (m, 2H), 2.48-2.44 (m, 2H), 2.02 (s, 6H), 1.57-1.04 (m, 26H), 0.99 (t, J=7.4 Hz, 3H), 0.89-0.85 (m, 15H).

Example 1E (R,R,R)-3-(3-hydroxy-3,7,11,15-tetramethyl-hexadecyl)-5-methyl-2-propyl-[1,4]benzoquinone

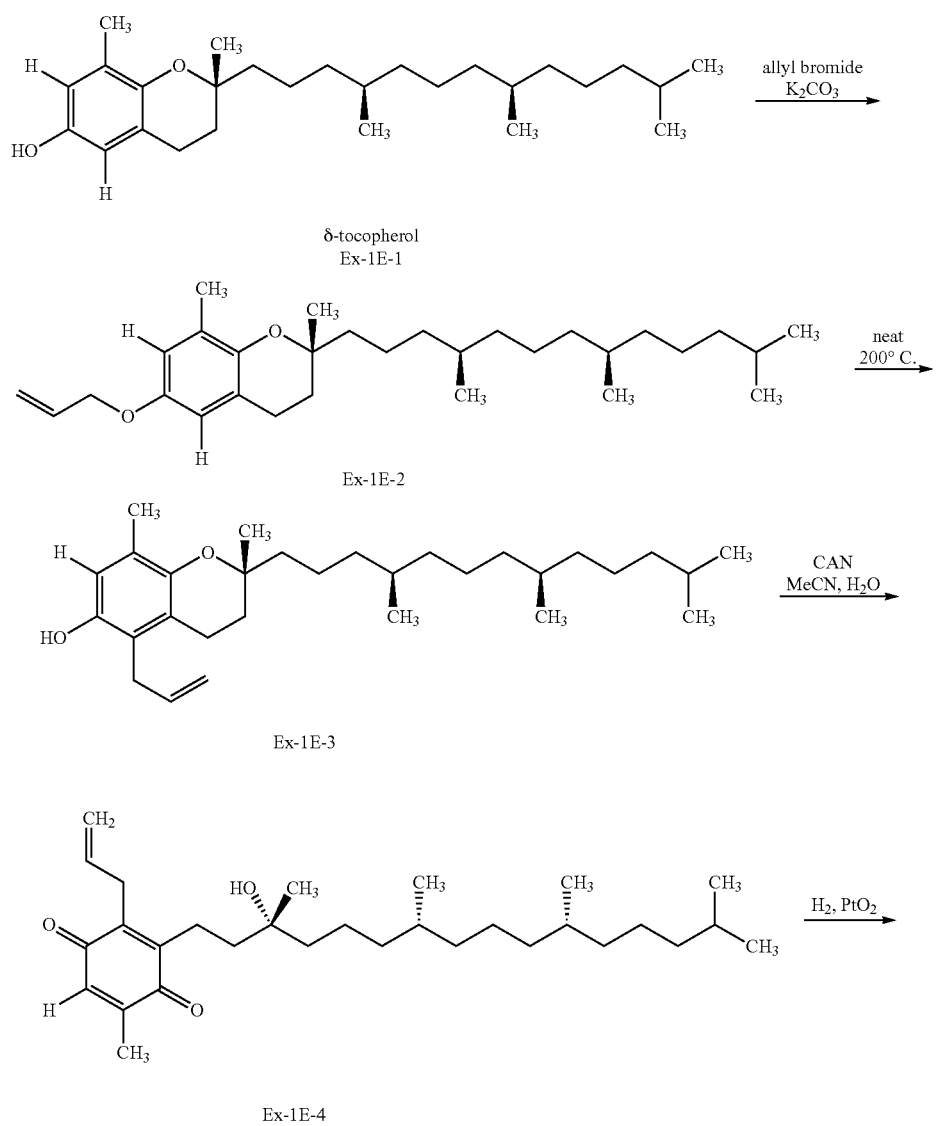

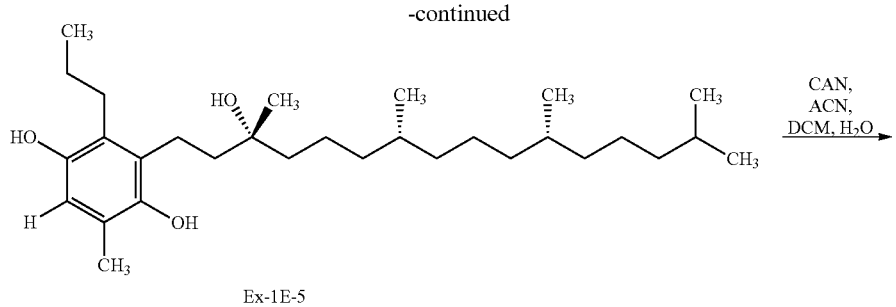

Ex-1E-5

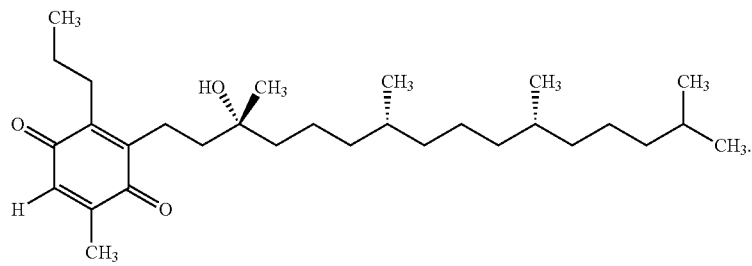

Ex-1E-6

Step 1: (+)-δ-tocopherol (Ex-1E-1) (1.04 g, 2.58 mmol), K₂CO₃ (715 mg, 5.17 mmol), allyl bromide (450 µL, 5.17 mmol) and acetone (10 mL) were charged to a 50 mL RBF. The reaction was heated to reflux for 16 h after which time it was deemed complete by TLC (1:5 EtOAc:Hept). The reaction was diluted with water (10 mL) and DCM (10 mL). The aqueous layer was separated and washed with DCM (3×10 mL). The combined DCM layers were dried over MgSO₄, filtered and concentrated by rotary evaporation to yield a pale yellow liquid (1.09 g). The liquid wash flashed through a silica plug (1:1: DCM:hept). After concentration of the eluent, (R,R,R)-6-allyloxy-2,8-dimethyl-2-(4,8,12-trimethyl-tridecyl)-chroman (Ex-1E-2) was obtained as a clear, colorless oil (0.97 g, 85%).

Step 2: (R,R,R)-6-allyloxy-2,8-dimethyl-2-(4,8,12-trimethyl-tridecyl)-chroman (Ex-1E-2) (0.97 g, 2.19 mmol) was heated to 200° C. for 3 h after which time the reaction was deemed complete (¹H NMR-4:1 mixture of isomers). The reaction was then cooled to RT to yield (R,R,R)-5-allyl-2,8-dimethyl-2-(4,8,12-trimethyl-tridecyl)-chroman-6-ol (Ex-1E-3) as a brown oil (0.97 g, 100%), which was carried on to the next step without further purification.

Step 3: A 50 mL RBF flask was charged with (R,R,R)-5-allyl-2,8-dimethyl-2-(4,8,12-trimethyl-tridecyl)-chroman-6-ol (Ex-1E-3) (280 mg, 0.63 mmol) and ACN (14 mL), then cooled to 0° C. A solution of CAN (710 mg, 1.30 mml) in water (2 mL) was added dropwise over 1 min to the reaction resulting in a bright orange solution. After 15 min, the reaction was deemed complete (TLC-5:1 hept:EtOAc). The reaction was extracted with MTBE (3×15 mL). The combined MTBE layers were dried over Na₂SO₄, filtered and concentrated by rotary evaporation to yield (R,R,R)-2-allyl-3-(3-hydroxy-3,7,11,15-tetramethyl-hexadecyl)-5-methyl-[1,4]benzoquinone (Ex-1E-4) as an orange oil (270 mg, 96%). ¹H NMR (400 MHz, CDCl₃) δ (ppm): 6.59 (d, J=1.4 Hz, 1H), 5.82 (ddt, 1H), 5.10-5.06 (m, 2H), 3.27 (d, J=6.2 Hz, 2H), 2.60-2.56 (m, 2H), 2.06 (s, 6H), 1.59-1.04 (m, 21H), 0.89-0.85 (m, 15H).

Step 4: (R,R,R)-2-allyl-3-(3-hydroxy-3,7,11,15-tetramethyl-hexadecyl)-5-methyl-[1,4]benzoquinone (Ex-1E-4) (115 mg, 0.25 mmol) was hydrogenated using PtO₂ (6 mg) at 50 psi for 3 h in a solution of EtOAc (7 mL). The suspension was filtered through silica, which was rinsed with EtOAc (40 mL). The solution was concentrated by rotary evaporation to yield (R,R,R)-3-(3-hydroxy-3,7,11,15-tetramethyl-hexadecyl)-5-methyl-2-propyl-benzene-1,4-diol (Ex-1E-5) as a clear, colorless oil (110 mg, 96%), which was carried on to the next step without further purification.

Step 5: A 50 mL RBF flask was charged with (R,R,R)-3-(3-hydroxy-3,7,11,15-tetramethyl-hexadecyl)-5-methyl-2-propyl-benzene-1,4-diol (Ex-1E-5) (110 mg, 0.24 mmol), ACN (15 mL) and DCM (2 mL), then cooled to 0° C. A solution of CAN (269 mg, 0.49 mmol) in water (1 mL) was added dropwise over 1 min to the reaction resulting in a bright orange solution. The reaction was stirred for 15 min then was diluted with water (5 mL). The aqueous layer was washed with DCM (3×30 mL). The combined DCM layers were dried over Na₂SO₄, filtered and concentrated by rotary evaporation to yield an orange oil. The oil was purified by column chromatography (gradient-hept to 20:1 hept.:EtOAc) to yield (R,R,R)-3-(3-hydroxy-3,7,11,15-tetramethyl-hexadecyl)-5-methyl-2-propyl-[1,4]benzoquinone (Ex-1E-6) as an orange oil (50 mg, 44%). ¹H NMR (400 MHz, CDCl₃) δ (ppm): 6.56 (s, 1H), 2.58-2.54 (m, 2H), 2.45 (t, J=7.9 Hz, 2H), 2.04 (s, 3H), 1.55-1.04 (m, 26H), 1.00 (t, J=7.4 Hz, 3H), 0.89-0.85 (m, 15H).

Example 1F
(R,R,R)-2-(3-hydroxy-3,7,11,15-tetramethyl-hexadecyl)-3-isobutyl-5,6-dimethyl-[1,4]benzoquinone
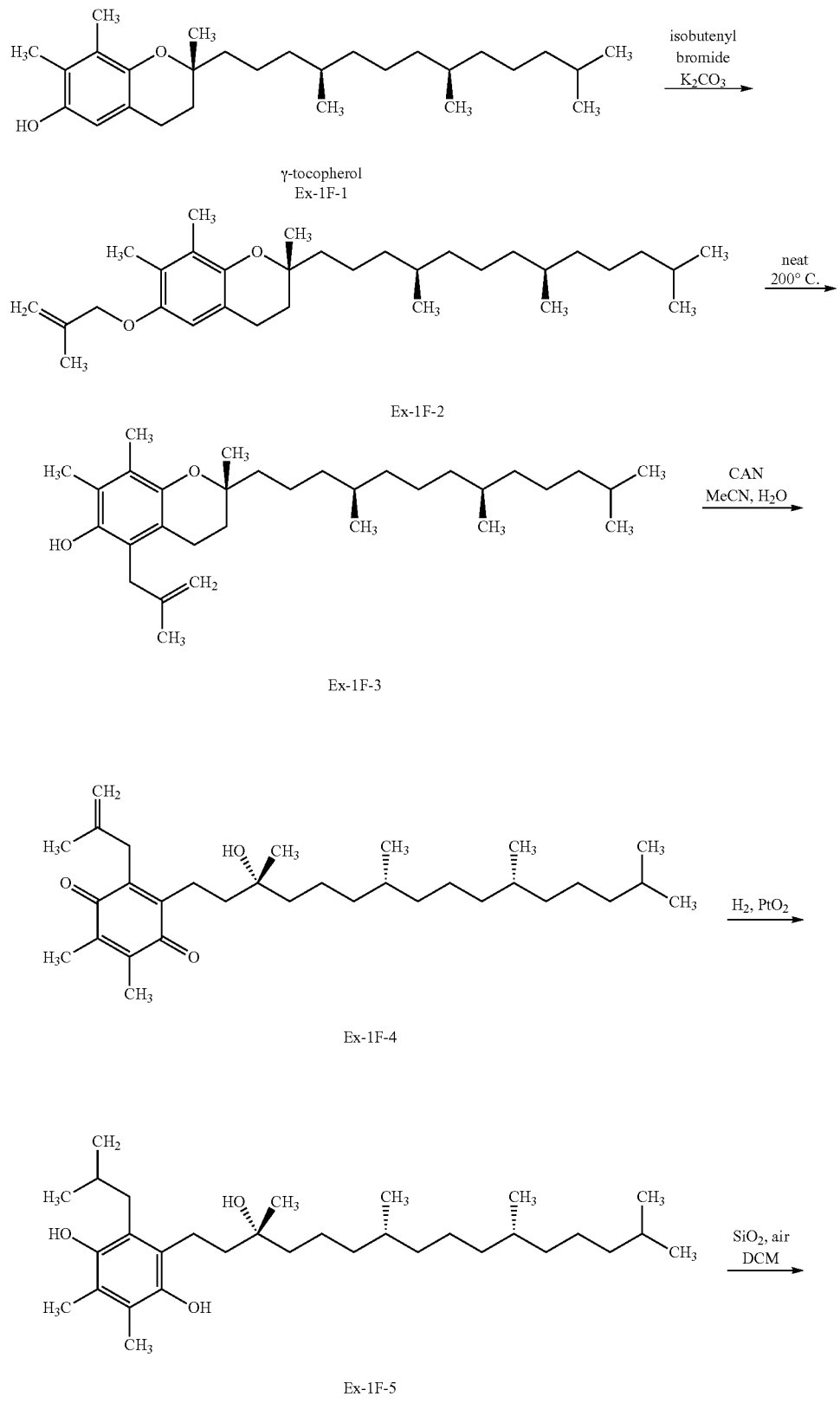

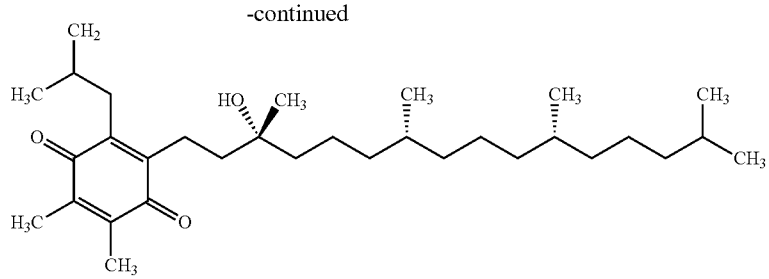

Ex-1F-6

Step 1: (+)-γ-tocopherol (Ex-1F-1) (300 mg, 0.72 mmol), K₂CO₃ (199 mg, 1.44 mmol), 3-chloro-2-methyl propene (450 μL, 5.17 mmol), NaI (10 mg) and acetone (8 mL) were charged to a 50 mL RBF. The reaction was heated to reflux for 20 h after which time it was deemed complete by TLC (1:9 EtOAc:Hept). The reaction was diluted with water (15 mL) and DCM (10 mL). The aqueous layer was separated and washed with DCM (3×10 mL). The combined DCM layers were dried over Na₂SO₄, filtered and concentrated by rotary evaporation to yield (R,R,R)-2,7,8-trimethyl-6-(2-methyl-allyloxy)-2-(4,8,12-trimethyl-tridecyl)-chroman as a pale yellow liquid (Ex-1F-2) (324 mg, 95%). The isolated product was used without any further purification.

Step 2: (R,R,R)-2,7,8-trimethyl-6-(2-methyl-allyloxy)-2-(4,8,12-trimethyl-tridecyl)-chroman (Ex-1F-2) (325 mg, 0.691 mmol) was heated to 200° C. for 4.5 h after which time the reaction was deemed complete (TLC-10:1 Heptane: EtOAc). The reaction was then cooled to RT to yield (R,R,R,)-2,7,8-trimethyl-5-(2-methyl-allyl)-2-(4,8,12-trimethyl-tridecyl)-chroman-6-ol (Ex-1F-3) (302 mg, 93%), which was taken to the next step without further purification.

Step 3: A 50 mL RBF flask was charged with crude (R,R,R,)-2,7,8-trimethyl-5-(2-methyl-allyl)-2-(4,8,12-trimethyl-tridecyl)-chroman-6-ol (Ex-1F-3) (150 mg, 0.32 mmol) and ACN (20 mL), then cooled to 0° C. A solution of CAN (362 mg, 0.66 mmol) in water (1 mL) was added dropwise over 1 min to the reaction resulting in a bright orange solution. After 15 min, the reaction was deemed complete (TLC-9:1 hept:EtOAc). The reaction was diluted with DCM (10 mL) and water (5 mL). The aqueous layer was washed with DCM (10 mL). The DCM layers were washed with brine (5 mL), dried over MgSO₄, filtered and concentrated by rotary evaporation to yield an orange oil. The oil was dissolved in DCM (10 mL) and passed through a silica plug. The DCM eluent was concentrated by rotary evaporation to yield (R,R,R,)-2-(3-hydroxy-3,7,11,15-tetramethyl-hexadecyl)-5,6-dimethyl-3-(2-methyl-allyl)-[1,4] benzoquinone (Ex-1F-4) as an orange oil (100 mg, 61%). ¹H NMR δ (ppm): 4.78 (s, 1H), 4.54 (s, 1H), 3.22 (s, 2H), 2.55-2.51 (m, 2H), 2.04 (s, 6H), 1.55-1.04 (m, 30H), 0.89-0.85 (m, 12H).

Step 4: (R,R,R,)-2-(3-hydroxy-3,7,11,15-tetramethyl-hexadecyl)-5,6-dimethyl-3-(2-methyl-allyl)-[1,4]benzoquinone (Ex-1F-4) (50 mg, 0.10 mmol) was hydrogenated using PtO₂ (5 mg) at 50 psi for 3 h in a solution of EtOAc (5 mL). The suspension was filtered through celite, which was rinsed with EtOAc (5 mL). The solution was concentrated by rotary evaporation to yield a clear, colorless oil (Ex-1F-5) (40 mg). The oil was dissolved in CDCl₃ (1 mL) and stirred with silica (~20 mg) for 5 days. The bright yellow suspension was filtered through a cotton plug and concentrated by rotary evaporation to yield (R,R,R)-2-(3-hydroxy-3,7,11,15-tetramethyl-hexadecyl)-3-isobutyl-5,6-dimethyl-[1,4]benzoquinone (Ex-1F-6) as a bright yellow oil (38 mg, 76%).

¹H NMR δ (ppm): 2.58-2.53 (m, 2H), 2.40 (d, J=7.2 Hz, 2H), 2.02 (s, 6H), 1.84 (sept, J=6.9 Hz, 1H) 1.56-1.03 (m, 27H), 0.93 (d, J=6.6 Hz, 6H), 0.90-0.84 (m, 12H).

Example 2

Initial Screen for Effective Redox Compounds

An initial screen was performed to identify compounds effective for the amelioration of redox disorders. Test samples, 4 reference compounds (idebenone, decylubiquinone, Trolox and α-tocopherol acetate), and solvent controls were tested for their ability to rescue FRDA fibroblasts stressed by addition of L-buthionine-(S,R)-sulfoximine (BSO), as described in Jauslin et al., Hum. Mol. Genet. 11(24):3055 (2002), Jauslin et al., FASEB J. 17:1972-4 (2003), and International Patent Application WO 2004/003565. Human dermal fibroblasts from Friedreich's Ataxia patients have been shown to be hypersensitive to inhibition of the de novo synthesis of glutathione (GSH) with L-buthionine-(S,R)-sulfoximine (BSO), a specific inhibitor of GSH synthetase (Jauslin et al., Hum. Mol. Genet. 11(24): 3055 (2002)). This specific BSO-mediated cell death can be prevented by administration of antioxidants or molecules involved in the antioxidant pathway, such as α-tocopherol, short chain quinones, selenium, or small molecule glutathione peroxidase mimetics. However, antioxidants differ in their potency, i.e. the concentration at which they are able to rescue BSO-stressed FRDA fibroblasts. With this assay $EC_{50}$ concentrations of the test compounds were determined and compared to known reference antioxidants.

MEM (a medium enriched in amino acids and vitamins, catalog no. 1-31F24-I) and Medium 199 (M199, catalog no. 1-21F224) with Earle's Balanced Salts, without phenol red, were purchased from Bioconcept. Fetal Calf Serum was obtained from PAA Laboratories. Basic fibroblast growth factor and epidermal growth factor were purchased from PeproTech. Penicillin-streptomycin-glutamine mix, L-buthionine (S,R)-sulfoximine, (+)-α-tocopherol acetate, decylubiquinone, and insulin from bovine pancreas were purchased from Sigma. Trolox (6-hydroxy-2,5,7,8-tetramethylchromane-2-carboxylic acid) was obtained from Fluka. Idebenone was obtained from Chemo Iberica. Calcein AM was purchased from Molecular Probes. Cell culture medium was made by combining 125 ml M199 EBS, 50 ml Fetal Calf Serum, 100 U/ml penicillin, 100 μg/ml streptomycin, 2 mM glutamine, 10 μg/ml insulin, 10 ng/ml EGF, and 10 ng/ml bFGF; MEM EBS was added to make the volume up to 500 ml. A 10 mM BSO solution was prepared by dissolving 444 mg BSO in 200 ml of medium with subsequent filter-sterilization. During the course of the experiments, this solution was stored at +4° C. The cells were obtained from the Coriell Cell Repositories (Camden, N.J.; repository number GM04078) and grown in 10 cm tissue culture plates. Every third day, they were split at a 1:3 ratio.

The test samples were supplied in 1.5 ml glass vials. The compounds were diluted with DMSO, ethanol or PBS to result in a 5 mM stock solution. Once dissolved, they were stored at −20° C. Reference antioxidants (idebenone, decylubiquinone, α-tocopherol acetate and trolox) were dissolved in DMSO.

Test samples were screened according to the following protocol: A culture with FRDA fibroblasts was started from a 1 ml vial with approximately 500,000 cells stored in liquid nitrogen. Cells were propagated in 10 cm cell culture dishes by splitting every third day in a ratio of 1:3 until nine plates were available. Once confluent, fibroblasts were harvested. For 54 micro titer plates (96 well-MTP) a total of 14.3 million cells (passage eight) were re-suspended in 480 ml medium, corresponding to 100 µl medium with 3,000 cells/well. The remaining cells were distributed in 10 cm cell culture plates (500,000 cells/plate) for propagation. The plates were incubated overnight at 37° C. in a atmosphere with 95% humidity and 5% $CO_2$ to allow attachment of the cells to the culture plate.

MTP medium (243 µl) was added to a well of the microtiter plate. The test compounds were unfrozen, and 7.5 µl of a 5 mM stock solution was dissolved in the well containing 243 µl medium, resulting in a 150 µM master solution. Serial dilutions from the master solution were made. The period between the single dilution steps was kept as short as possible (generally less than 1 second).

Plates were kept overnight in the cell culture incubator. The next day, 10 µl of a 10 mM BSO solution were added to the wells, resulting in a 1 mM final BSO concentration. Forty-eight hours later, three plates were examined under a phase-contrast microscope to verify that the cells in the 0% control (wells E1-H1) were clearly dead. The medium from all plates was discarded, and the remaining liquid was removed by gently tapping the plate inversed onto a paper towel.

100 µl of PBS containing 1.2 µM Calcein AM were then added to each well. The plates were incubated for 50-70 minutes at room temperature. After that time the PBS was discarded, the plate gently tapped on a paper towel and fluorescence (excitation/emission wavelengths of 485 nm and 525 nm, respectively) was read on a Gemini fluorescence reader. Data was imported into Microsoft Excel (EXCEL is a registered trademark of Microsoft Corporation for a spreadsheet program) and used to calculate the $EC_{50}$ concentration for each compound.

The compounds were tested three times, i.e., the experiment was performed three times, the passage number of the cells increasing by one with every repetition.

The solvents (DMSO, ethanol, PBS) neither had a detrimental effect on the viability of non-BSO treated cells nor did they have a beneficial influence on BSO-treated fibroblasts even at the highest concentration tested (1%). None of the compounds showed auto-fluorescence. The viability of non-BSO treated fibroblasts was set as 100%, and the viability of the BSO- and compound-treated cells was calculated as relative to this value.

The following table summarizes the EC50 for alpha-tocopherol quinone and the four control compounds.

| Compound | $EC_{50}$ [µM] | | | | |
|---|---|---|---|---|---|
| | Value 1 | Value 2 | Value 3 | Average | Stdev |
| α-tocopherol quinone | 0.000001 | 0.000003 | 2E−07 | 1.40E−06 | 1.44E−06 |
| decylubiquinone | 0.05 | 0.035 | 0.03 | 0.038 | 0.010 |
| α-tocopherol acetate | 0.4 | 0.15 | 0.35 | 0.30 | 0.13 |
| idebenone | 1.5 | 1 | 1 | 1.2 | 0.3 |
| Trolox | 9 | 9 | 8 | 8.7 | 0.6 |

Example 3

Screening Compounds of the Invention

Compounds of the invention are tested using the screen as described in Example 2 for their ability to rescue human dermal fibroblasts from FRDA patients from oxidative stress. This data is used to estimate their potential as disease treatments.

Example 4

Administration of Compounds of the Invention

A compound of the invention, such as alpha-tocopherol quinone, is presented in a capsule containing 300 mg of compound in a pharmaceutically acceptable carrier. A capsule is taken orally, once a day, preferably during breakfast or lunch. In case of very young children, the capsule is broken and its contents mixed with food.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of treating a mitochondrial disorder, comprising administering to a subject in need thereof a composition comprising a therapeutically effective amount of one or more compounds selected from the group consisting of the following formulas:

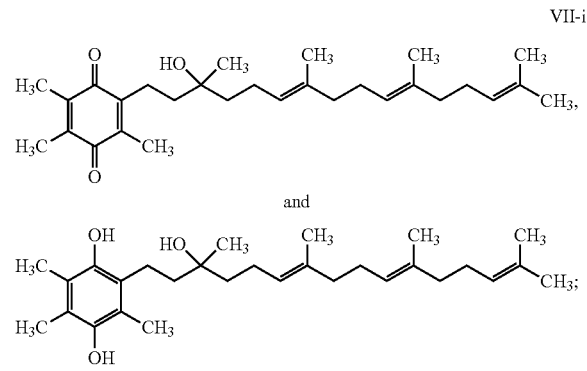

and all stereoisomers, or mixtures of stereoisomers thereof, wherein the one or more compounds are the sole active pharmaceutical agent or agents present in a therapeutically effective amount in the composition, and wherein the mitochondrial disorder is selected from the group consisting of an inherited mitochondrial disease; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Syndrome; Kearns-Sayre Syndrome (KSS); and Friedreich's Ataxia (FA).

2. The method of claim 1, wherein the mitochondrial disorder is Leber's Hereditary Optic Neuropathy (LHON).

3. The method of claim 1, wherein the mitochondrial disorder is Leigh Syndrome.

4. The method of claim 1, wherein the one or more compounds is:

VII-i or a stereoisomer, or mixture of stereoisomers thereof.

5. The method of claim 4, wherein the mitochondrial disorder is an inherited mitochondrial disease.

6. The method of claim 4, wherein the mitochondrial disorder is Leber's Hereditary Optic Neuropathy (LHON).

7. The method of claim 4, wherein the mitochondrial disorder is Leigh Syndrome.

8. The method of claim 4, wherein the mitochondrial disorder is Myoclonic Epilepsy with Ragged Red Fibers (MERRF).

9. The method of claim 4, wherein the mitochondrial disorder is Mitochondrial Myopathy, Encephalopathy, Lactacidosis, Stroke (MELAS).

10. The method of claim 4, wherein the mitochondrial disorder is Kearns-Sayre Syndrome (KSS).

11. The method of claim 4, wherein the mitochondrial disorder is Friedreich's Ataxia (FA).

12. The method of claim 1, wherein the one or more compounds is:

or a stereoisomer, or mixture of stereoisomers thereof.

13. The method of claim 12, wherein the mitochondrial disorder is an inherited mitochondrial disease.

14. The method of claim 12, wherein the mitochondrial disorder is Leber's Hereditary Optic Neuropathy (LHON).

15. The method of claim 12, wherein the mitochondrial disorder is Leigh Syndrome.

16. The method of claim 12, wherein the mitochondrial disorder is Myoclonic Epilepsy with Ragged Red Fibers (MERRF).

17. The method of claim 12, wherein the mitochondrial disorder is Mitochondrial Myopathy, Encephalopathy, Lactacidosis, Stroke (MELAS).

18. The method of claim 12, wherein the mitochondrial disorder is Kearns-Sayre Syndrome (KSS).

19. The method of claim 12, wherein the mitochondrial disorder is Friedreich's Ataxia (FA).

20. A method of treating epilepsy caused by a mitochondrial disorder, comprising administering to a subject in need thereof a composition comprising a therapeutically effective amount of one or more compounds selected from the group consisting of the following formulas:

VII-i and and all stereoisomers, or mixtures of stereoisomers thereof, wherein the one or more compounds are the sole active pharmaceutical agent or agents present in a therapeutically effective amount in the composition.

21. The method of claim 20, wherein the one or more compounds is:

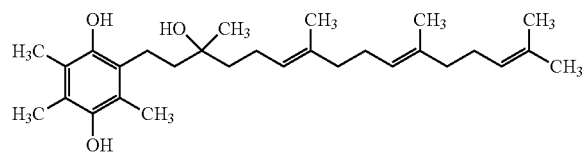 [SMILES: CC(C)=CCC/C(C)=C/CC/C(C)=C/CCC(C)(O)CCc1c(C)c(O)c(C)c(C)c1O]

or a stereoisomer, or mixture of stereoisomers thereof.

22. The method of claim 1, wherein the composition comprises a pharmaceutically acceptable carrier, vehicle, or excipient.

23. The method of claim 4, wherein the composition comprises a pharmaceutically acceptable carrier, vehicle, or excipient.

24. The method of claim 12, wherein the composition comprises a pharmaceutically acceptable carrier, vehicle, or excipient.

25. A method of treating a mitochondrial disorder, comprising administering to a subject in need thereof a therapeutically effective amount of one or more compounds selected from the group consisting of the following formulas:

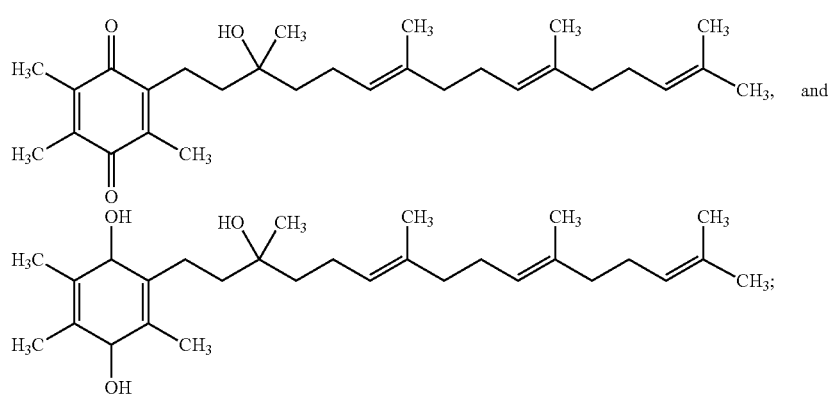

and all stereoisomers, or mixtures of stereoisomers thereof, and wherein the mitochondrial disorder is selected from the group consisting of an inherited mitochondrial disease; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Syndrome; Kearns-Sayre Syndrome (KSS); and Friedreich's Ataxia (FA).

26. The method of claim 25, wherein the one or more compounds is:

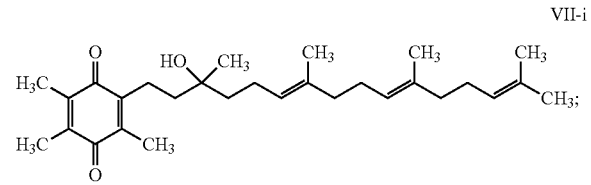 [SMILES: CC(C)=CCC/C(C)=C/CC/C(C)=C/CCC(C)(O)CCC1=C(C)C(=O)C(C)=C(C)C1=O]

or a stereoisomer, or mixture of stereoisomers thereof.

27. The method of claim 26, wherein the mitochondrial disorder is an inherited mitochondrial disease.

28. The method of claim 26, wherein the mitochondrial disorder is Myoclonic Epilepsy with Ragged Red Fibers (MERRF).

29. The method of claim 26, wherein the mitochondrial disorder is Mitochondrial Myopathy, Encephalopathy, Lactacidosis, Stroke (MELAS).

30. The method of claim 26, wherein the mitochondrial disorder is Leber's Hereditary Optic Neuropathy (LHON).

31. The method of claim 26, wherein the mitochondrial disorder is Leigh Syndrome.

32. The method of claim 26, wherein the mitochondrial disorder is Kearns-Sayre Syndrome (KSS).

33. The method of claim 26, wherein the mitochondrial disorder is Friedreich's Ataxia (FA).

34. The method of claim 26, wherein the method comprises administering to the subject a pharmaceutical composition comprising the one or more compounds and a pharmaceutically acceptable carrier, vehicle, or excipient.

35. The method of claim 25, wherein the one or more compounds is:

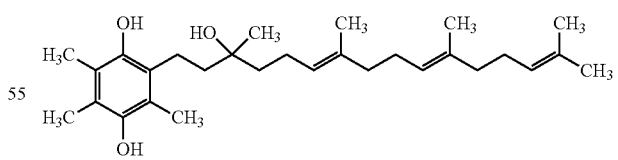

or a stereoisomer, or mixture of stereoisomers thereof.

36. The method of claim 35, wherein the mitochondrial disorder is an inherited mitochondrial disease.

37. The method of claim 35, wherein the mitochondrial disorder is Myoclonic Epilepsy with Ragged Red Fibers (MERRF).

38. The method of claim 35, wherein the mitochondrial disorder is Mitochondrial Myopathy, Encephalopathy, Lactacidosis, Stroke (MELAS).

39. The method of claim 35, wherein the mitochondrial disorder is Leber's Hereditary Optic Neuropathy (LHON).

40. The method of claim 35, wherein the mitochondrial disorder is Leigh Syndrome.

41. The method of claim 35, wherein the mitochondrial disorder is Kearns-Sayre Syndrome (KSS).

42. The method of claim 35, wherein the mitochondrial disorder is Friedreich's Ataxia (FA).

43. The method of claim 35, wherein the method comprises administering to the subject a pharmaceutical composition comprising the one or more compounds and a pharmaceutically acceptable carrier, vehicle, or excipient.

44. The method of claim 4, wherein the total daily dosage of the one or more compounds that are administered to the subject is about 1 mg to about 100 mg/kg.

45. The method of claim 26, wherein the total daily dosage of the one or more compounds that are administered to the subject is about 1 mg to about 100 mg/kg.

46. The method of claim 4, wherein the one or more compounds are the sole active pharmaceutical agent or agents in the composition.

47. The method of claim 12, wherein the one or more compounds are the sole active pharmaceutical agent or agents in the composition.

48. The method of claim 4, wherein the method consists of administering the composition to the subject.

49. The method of claim 12, wherein the method consists of administering the composition to the subject.

50. A method treating a mitochondrial disorder, comprising administering to a subject in need thereof a composition comprising a therapeutically effective amount of one or more compounds selected from the group consisting of the following formulas:

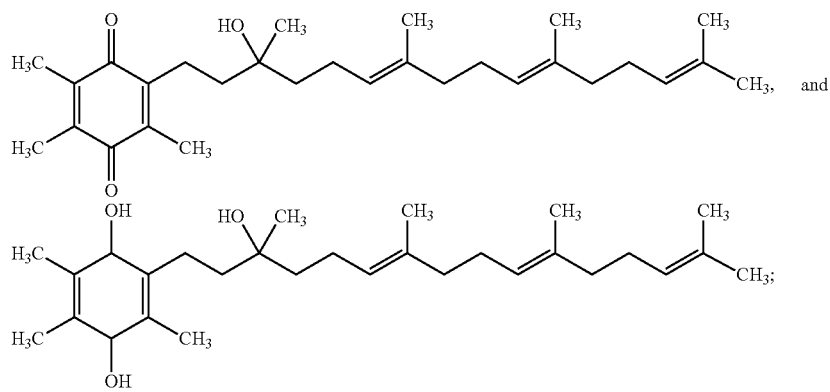

and all stereoisomers, or mixtures of stereoisomers thereof, wherein the one or more compounds are the sole active pharmaceutical agent or agents used to treat the disorder; and wherein the mitochondrial disorder is selected from the group consisting of an inherited mitochondrial disease; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Syndrome; Kearns-Sayre Syndrome (KSS); and Friedreich's Ataxia (FA).

51. The method of claim 50, wherein the one or more compounds is:

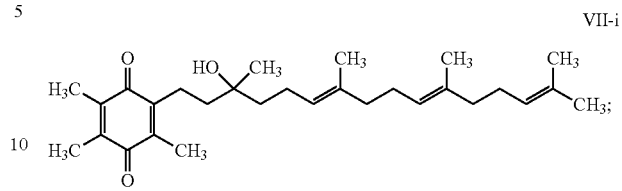

or a stereoisomer, or mixture of stereoisomers thereof.

52. The method of claim 51, wherein the mitochondrial disorder is an inherited mitochondrial disease.

53. The method of claim 51, wherein the mitochondrial disorder is Myoclonic Epilepsy with Ragged Red Fibers (MERRF).

54. The method of claim 51, wherein the mitochondrial disorder is Mitochondrial Myopathy, Encephalopathy, Lactacidosis, Stroke (MELAS).

55. The method of claim 51, wherein the mitochondrial disorder is Leber's Hereditary Optic Neuropathy (LHON).

56. The method of claim 51, wherein the mitochondrial disorder is Leigh Syndrome.

57. The method of claim 51, wherein the mitochondrial disorder is Kearns-Sayre Syndrome (KSS).

58. The method of claim 51, wherein the mitochondrial disorder is Friedreich's Ataxia (FA).

59. The method of claim 4, wherein the one or more compounds is:

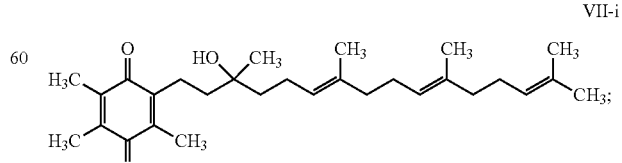

or an enantiomer thereof.

60. The method of claim 26, wherein the one or more compounds is:
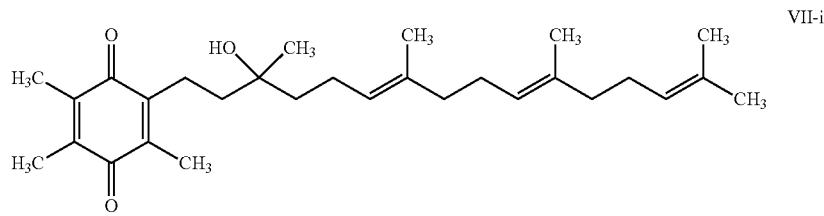 [SMILES: CC(C)=CCC/C(C)=C/CC/C(C)=C/CCC(C)(O)CCC1=C(C)C(=O)C(C)=C(C)C1=O]
or an enantiomer thereof.
61. The method of claim 46, wherein the one or more compounds is:
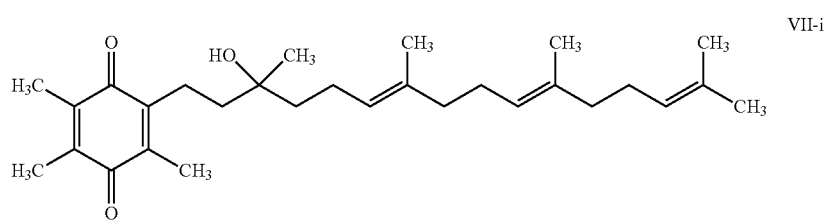 [SMILES: CC(C)=CCC/C(C)=C/CC/C(C)=C/CCC(C)(O)CCC1=C(C)C(=O)C(C)=C(C)C1=O]
or an enantiomer thereof.
62. The method of claim 48, wherein the one or more compounds is:
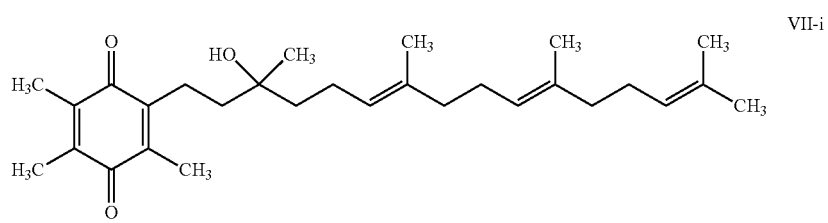 [SMILES: CC(C)=CCC/C(C)=C/CC/C(C)=C/CCC(C)(O)CCC1=C(C)C(=O)C(C)=C(C)C1=O]
or an enantiomer thereof.
63. The method of claim 51, wherein the one or more compounds is:
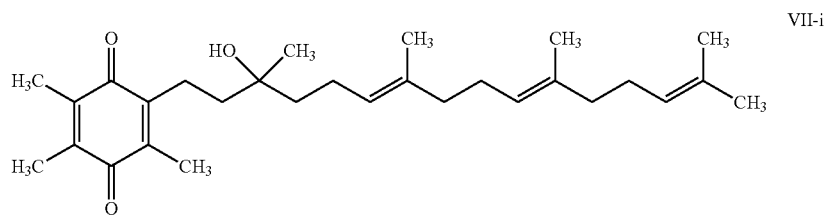 [SMILES: CC(C)=CCC/C(C)=C/CC/C(C)=C/CCC(C)(O)CCC1=C(C)C(=O)C(C)=C(C)C1=O]
or an enantiomer thereof.

64. The method of claim 20, wherein the one or more compounds is:

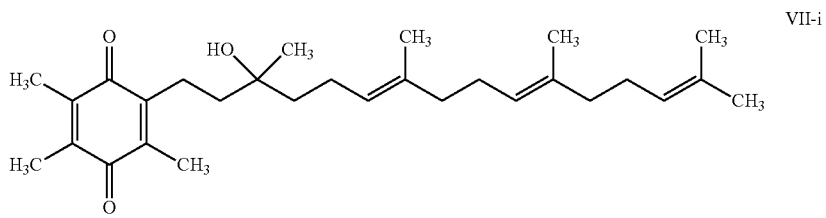 [SMILES: CC(C)=CCC/C(C)=C/CC/C(C)=C/CCC(C)(O)CCC1=C(C)C(=O)C(C)=C(C)C1=O]

VII-i or a stereoisomer, or mixture of stereoisomers thereof.

65. The method of claim 20, wherein the composition comprises a pharmaceutically acceptable carrier, vehicle, or excipient.

66. The method of claim 64, wherein the composition comprises a pharmaceutically acceptable carrier, vehicle, or excipient.

67. The method of claim 21, wherein the composition comprises a pharmaceutically acceptable carrier, vehicle, or excipient.

68. The method of claim 64, wherein the one or more compounds is:

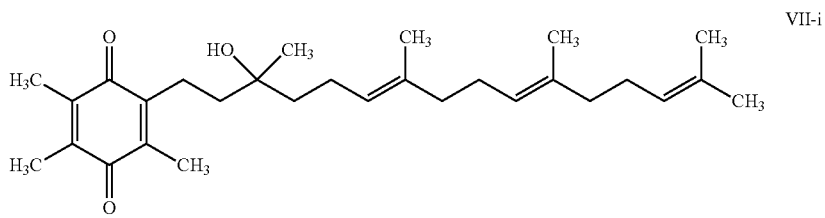 [SMILES: CC(C)=CCC/C(C)=C/CC/C(C)=C/CCC(C)(O)CCC1=C(C)C(=O)C(C)=C(C)C1=O]

VII-i or an enantiomer thereof.

69. A method of treating epilepsy caused by a mitochondrial disorder, comprising administering to a subject in need thereof a composition comprising a therapeutically effective amount of one or more compounds selected from the group consisting of the following formulas:

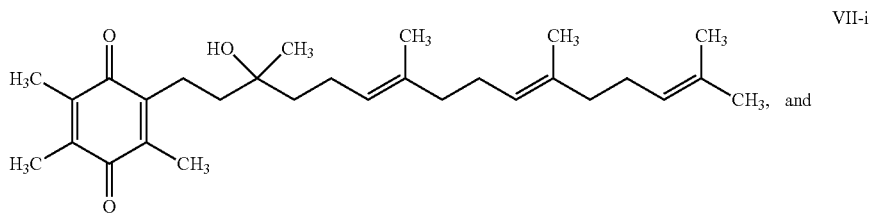

VII-i and

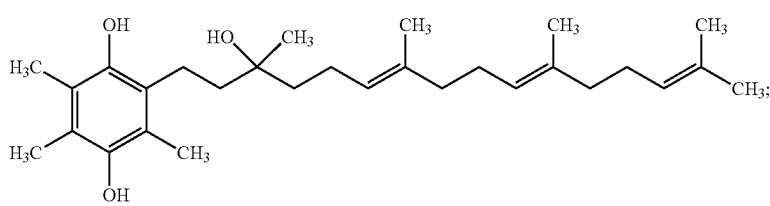

and all stereoisomers, or mixtures of stereoisomers thereof.

70. The method of claim 69, wherein the one or more compounds is:

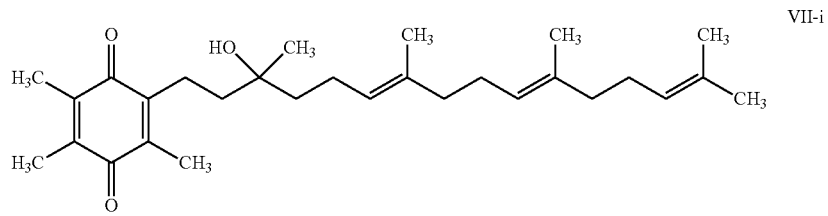 [SMILES: CC(C)=CCC/C(C)=C/CC/C(C)=C/CCC(C)(O)CCC1=C(C)C(=O)C(C)=C(C)C1=O]

or a stereoisomer, or mixture of stereoisomers thereof.

71. The method of claim 70, wherein the composition comprises a pharmaceutically acceptable carrier, vehicle, or excipient.

72. The method of claim 70, wherein the one or more compounds is:

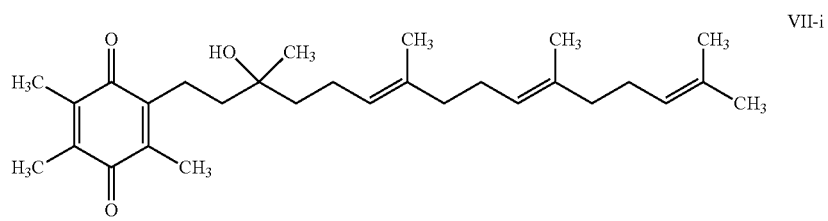 [SMILES: CC(C)=CCC/C(C)=C/CC/C(C)=C/CCC(C)(O)CCC1=C(C)C(=O)C(C)=C(C)C1=O]

or an enantiomer thereof.

73. The method of claim 69, wherein the one or more compounds is:

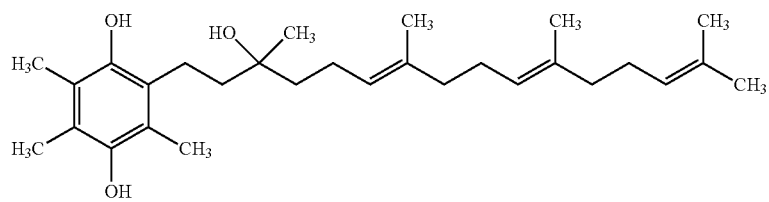 [SMILES: CC(C)=CCC/C(C)=C/CC/C(C)=C/CCC(C)(O)CCc1c(C)c(O)c(C)c(C)c1O]

or a stereoisomer, or mixture of stereoisomers thereof.

74. The method of claim 73, wherein the composition comprises a pharmaceutically acceptable carrier, vehicle, or excipient.

75. The method of claim 64, wherein the total daily dosage of the one or more compounds that are administered to the subject is about 1 mg to about 100 mg/kg.

76. The method of claim 70, wherein the total daily dosage of the one or more compounds that are administered to the subject is about 1 mg to about 100 mg/kg.

77. The method of claim 64, wherein the one or more compounds are the sole active pharmaceutical agent or agents in the composition.

78. The method of claim 77, wherein the one or more compounds is:

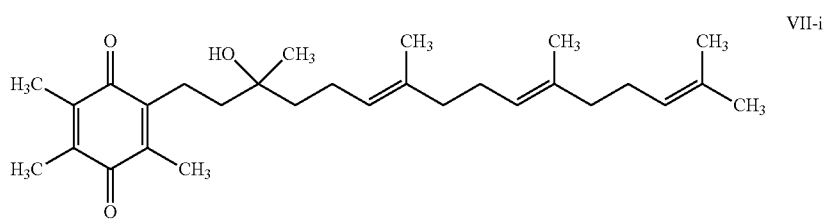 [SMILES: CC(C)=CCC/C(C)=C/CC/C(C)=C/CCC(C)(O)CCC1=C(C)C(=O)C(C)=C(C)C1=O]

or an enantiomer thereof.

79. The method of claim 21, wherein the one or more compounds are the sole active pharmaceutical agent or agents in the composition.

80. The method of claim 64, wherein the method consists of administering the composition to the subject.

81. The method of claim 80, wherein the one or more compounds is:

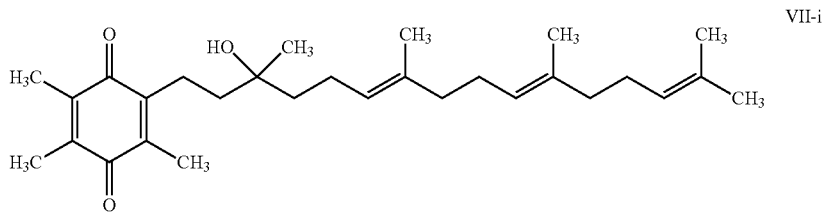 [SMILES: CC(C)=CCC/C(C)=C/CC/C(C)=C/CCC(C)(O)CCC1=C(C)C(=O)C(C)=C(C)C1=O]
VII-i or an enantiomer thereof.

82. The method of claim 21, wherein the method consists of administering the composition to the subject.

83. A method of treating epilepsy caused by a mitochondrial disorder, comprising administering to a subject in need thereof a composition comprising a therapeutically effective amount of one or more compounds selected from the group consisting of the following formulas:

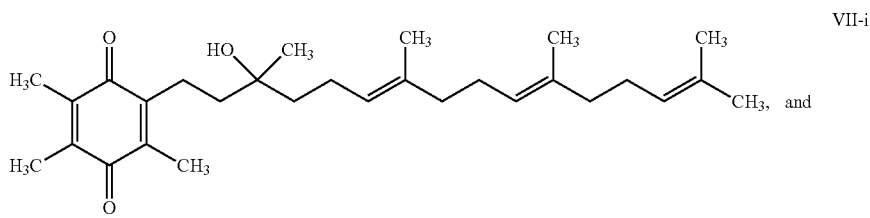
VII-i and

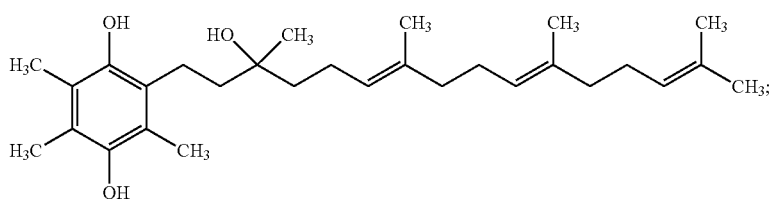

and all stereoisomers, or mixtures of stereoisomers thereof, wherein the one or more compounds are the sole active pharmaceutical agent or agents used to treat the disorder.

84. The method of claim 83, wherein the one or more compounds is:

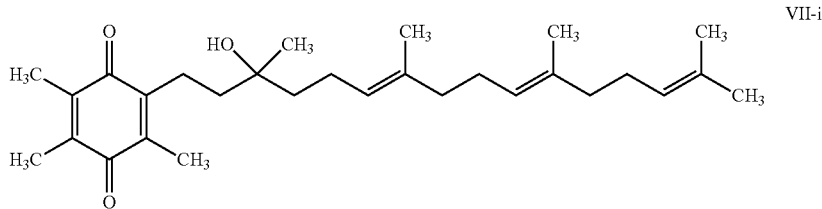 [SMILES: CC(C)=CCC/C(C)=C/CC/C(C)=C/CCC(C)(O)CCC1=C(C)C(=O)C(C)=C(C)C1=O]
VII-i or a stereoisomer, or mixture of stereoisomers thereof.

85. The method of claim 84, wherein the one or more compounds is:
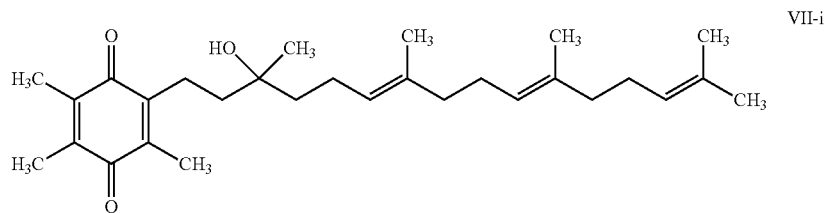 [SMILES: CC(C)=CCC/C(C)=C/CC/C(C)=C/CCC(C)(O)CCC1=C(C)C(=O)C(C)=C(C)C1=O]
VII-i
or an enantiomer thereof.
* * * * *

UNITED STATES PATENT AND TRADEMARK OFFICE
CERTIFICATE OF CORRECTION

PATENT NO. : 11,021,424 B2  
APPLICATION NO. : 12/777179  
DATED : June 1, 2021  
INVENTOR(S) : Guy M. Miller and Sidney M. Hecht Page 1 of 1

It is certified that error appears in the above-identified patent and that said Letters Patent is hereby corrected as shown below:

In the Claims

In Claim 50, at Column 95, Line 29, cancel the text:
"A method treating"

And insert the following:
--A method of treating--

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*